(12) United States Patent
D'Alessio, II et al.

(10) Patent No.: US 8,377,069 B2
(45) Date of Patent: Feb. 19, 2013

(54) UNICONDYLAR KNEE CUTTING GUIDE

(75) Inventors: Jerry D'Alessio, II, Belleville, NJ (US); Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1303 days.

(21) Appl. No.: 11/504,420

(22) Filed: Aug. 15, 2006

(65) Prior Publication Data
US 2008/0015606 A1   Jan. 17, 2008

Related U.S. Application Data

(63) Continuation of application No. 11/471,931, filed on Jun. 21, 2006, now Pat. No. 7,678,115.

(51) Int. Cl.
*A61F 5/00* (2006.01)

(52) U.S. Cl. .............. 606/88; 606/86 R; 606/87

(58) Field of Classification Search .......... 606/86 R, 606/87, 88, 89, 96
See application file for complete search history.

(56) References Cited

U.S. PATENT DOCUMENTS

| | | | |
|---|---|---|---|
| 4,421,112 A | 12/1983 | Mains et al. | |
| 4,467,801 A | 8/1984 | Whiteside | |
| 4,502,483 A | 3/1985 | Lacey | |
| 4,509,511 A | 4/1985 | Neufeld | |
| 4,524,766 A | 6/1985 | Petersen | |
| 4,567,886 A | 2/1986 | Petersen | |
| 4,574,794 A | 3/1986 | Cooke et al. | |
| 4,703,751 A | 11/1987 | Pohl | |
| 4,718,413 A | 1/1988 | Johnson | |
| 4,773,407 A | 9/1988 | Petersen | |
| 4,787,383 A | 11/1988 | Kenna | |
| 4,841,975 A | 6/1989 | Woolson | |
| 4,926,847 A | 5/1990 | Luckman | |
| 5,098,436 A | 3/1992 | Ferrante et al. | |
| 5,100,409 A | 3/1992 | Coates et al. | |
| 5,122,144 A | 6/1992 | Bert et al. | |
| 5,171,244 A | 12/1992 | Caspari et al. | |
| 5,193,672 A * | 3/1993 | Long | 206/45.2 |
| 5,228,459 A | 7/1993 | Caspari et al. | |
| 5,234,433 A | 8/1993 | Bert et al. | |
| 5,263,498 A | 11/1993 | Caspari et al. | |
| 5,282,866 A * | 2/1994 | Cohen et al. | 623/20.34 |

(Continued)

FOREIGN PATENT DOCUMENTS
EP     327387     8/1989

OTHER PUBLICATIONS

Preservation Uni-Compartmental Knee, Surgical Technique, DePuy, (date not known).

(Continued)

*Primary Examiner* — Kevin T Truong
*Assistant Examiner* — Christian Sevilla
(74) *Attorney, Agent, or Firm* — Lerner, David, Littenberg, Krumholz & Mentlik, LLP

(57) ABSTRACT

A system for forming keel openings in tibial bone includes a plurality of templates having different sizes, each template having a top surface, a bottom surface and a central opening extending between the top and bottom surfaces. The system includes a bone cutting instrument for forming the keel openings and a guide having a leading end that is adapted to be coupled with the templates so that the leading end of the guide is aligned with the central openings in the templates. The guide includes a plurality of slots extending toward the leading end thereof for guiding advancement of the bone cutting instrument through the central openings in the templates. Each slot is associated for use with one of the differently sized templates.

20 Claims, 49 Drawing Sheets

U.S. PATENT DOCUMENTS

| | | | |
|---|---|---|---|
| 5,304,181 A | | 4/1994 | Caspari et al. |
| 5,356,414 A | * | 10/1994 | Cohen et al. ............... 606/88 |
| 5,364,402 A | | 11/1994 | Mumme et al. |
| 5,395,376 A | | 3/1995 | Caspari et al. |
| 5,423,822 A | | 6/1995 | Hershberger et al. |
| 5,486,180 A | | 1/1996 | Dietz et al. |
| 5,514,139 A | | 5/1996 | Goldstein et al. |
| 5,520,695 A | | 5/1996 | Luckman |
| 5,597,379 A | | 1/1997 | Haines et al. |
| 5,634,927 A | * | 6/1997 | Houston et al. ............. 606/96 |
| 5,643,272 A | | 7/1997 | Haines et al. |
| 5,649,929 A | | 7/1997 | Callaway |
| 5,662,656 A | | 9/1997 | White |
| 5,688,279 A | | 11/1997 | McNulty et al. |
| 5,690,636 A | * | 11/1997 | Wildgoose et al. ............ 606/88 |
| 5,709,689 A | | 1/1998 | Ferrante et al. |
| 5,741,266 A | * | 4/1998 | Moran et al. ............... 606/96 |
| 5,769,855 A | | 6/1998 | Bertin et al. |
| 5,810,827 A | | 9/1998 | Haines et al. |
| 5,871,541 A | | 2/1999 | Gerber |
| 5,885,296 A | | 3/1999 | Masini |
| 5,911,723 A | | 6/1999 | Ashby et al. |
| 5,944,722 A | | 8/1999 | Masini |
| 5,947,973 A | | 9/1999 | Masini |
| 5,957,926 A | | 9/1999 | Masini |
| 5,961,523 A | | 10/1999 | Masini |
| 6,024,746 A | | 2/2000 | Katz |
| 6,056,754 A | | 5/2000 | Haines et al. |
| 6,059,831 A | | 5/2000 | Braslow et al. |
| 6,077,269 A | | 6/2000 | Masini |
| 6,077,270 A | | 6/2000 | Katz |
| 6,159,216 A | * | 12/2000 | Burkinshaw et al. ............ 606/88 |
| 6,187,010 B1 | | 2/2001 | Masini |
| 6,258,095 B1 | | 7/2001 | Lombardo et al. |
| 6,355,045 B1 | * | 3/2002 | Gundlapalli et al. ............ 606/88 |
| 6,503,254 B2 | | 1/2003 | Masini |
| 6,554,838 B2 | * | 4/2003 | McGovern et al. ............. 606/87 |
| 6,575,980 B1 | | 6/2003 | Robie et al. |
| 6,673,077 B1 | * | 1/2004 | Katz ........................ 606/88 |
| 6,702,821 B2 | | 3/2004 | Bonutti |
| 6,758,850 B2 | | 7/2004 | Smith et al. |
| 6,770,078 B2 | | 8/2004 | Bonutti |
| 7,060,074 B2 | | 6/2006 | Rosa et al. |
| 7,104,996 B2 | | 9/2006 | Bonutti |
| 7,442,196 B2 | | 10/2008 | Fisher et al. |
| 2001/0001121 A1 | | 5/2001 | Lombardo et al. |
| 2002/0029038 A1 | | 3/2002 | Haines |
| 2002/0183760 A1 | | 12/2002 | McGovern et al. |
| 2002/0198528 A1 | | 12/2002 | Engh et al. |
| 2003/0009171 A1 | * | 1/2003 | Tornier ..................... 606/96 |
| 2003/0018338 A1 | | 1/2003 | Axelson et al. |
| 2003/0093079 A1 | | 5/2003 | Masini |
| 2003/0100906 A1 | | 5/2003 | Rosa et al. |
| 2003/0100907 A1 | | 5/2003 | Rosa et al. |
| 2003/0130665 A1 | | 7/2003 | Pinczewski et al. |
| 2003/0153923 A1 | | 8/2003 | Pinczewski et al. |
| 2003/0171757 A1 | | 9/2003 | Coon et al. |
| 2003/0225413 A1 | | 12/2003 | Sanford et al. |
| 2004/0036189 A1 | | 2/2004 | Ensign et al. |
| 2004/0153086 A1 | | 8/2004 | Sanford |
| 2004/0153087 A1 | | 8/2004 | Sanford et al. |
| 2004/0153162 A1 | | 8/2004 | Sanford et al. |
| 2004/0249385 A1 | | 12/2004 | Faoro |
| 2004/0249386 A1 | | 12/2004 | Faoro |
| 2004/0249387 A1 | | 12/2004 | Faoro |
| 2005/0020941 A1 | | 1/2005 | Tarabichi |
| 2005/0113840 A1 | | 5/2005 | Metzger et al. |
| 2005/0154471 A1 | | 7/2005 | Aram et al. |
| 2005/0234461 A1 | | 10/2005 | Burdulis et al. |
| 2006/0015120 A1 | | 1/2006 | Richard et al. |
| 2006/0116772 A1 | * | 6/2006 | Haidukewych ............ 623/20.34 |

OTHER PUBLICATIONS

Intramedullary Surgical Approach, MIS Minimally Invasive Solution, The Uni-Compartmental Knee Minimally Invasive Surgical Technique, Zimmer, 2002.

EIUS, Surgical Technique, The Minimally Invasive Uni Knee System, Stryker Howmedica Osteonics, 2002.

Advance Unicompartmental Knee System, Surgical Technique, Wright Medical Technology, Inc., 2003.

Accuris, Redefining the Uni Knee, Accurately, Minimally Invasive Unicompartmental Knee System, Surgical Technique, Smith & Nephew Orthopeadics, 2003.

Vanguard M Series, Minimally Invasive Unicompartmental Knee System, Minimally Invasive Surgical Technique, Biomet Orthopedics, Inc., 2002.

EUIS, Surgical Technique, Minimally Invasive Uni Knee System, Stryker Orthopeadics, 2004.

* cited by examiner

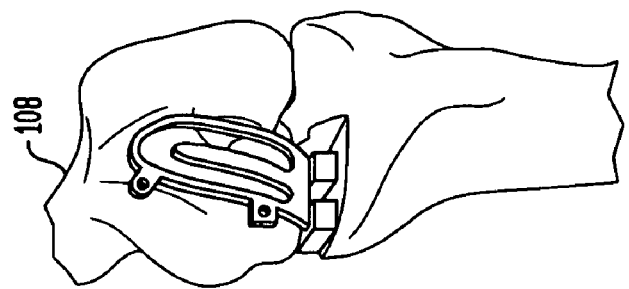
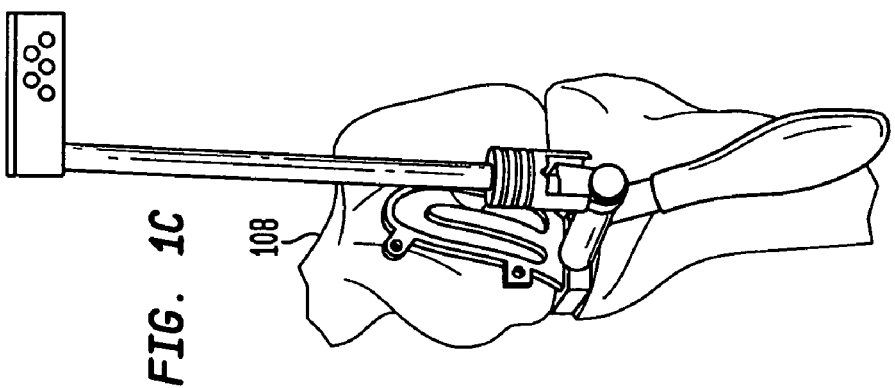
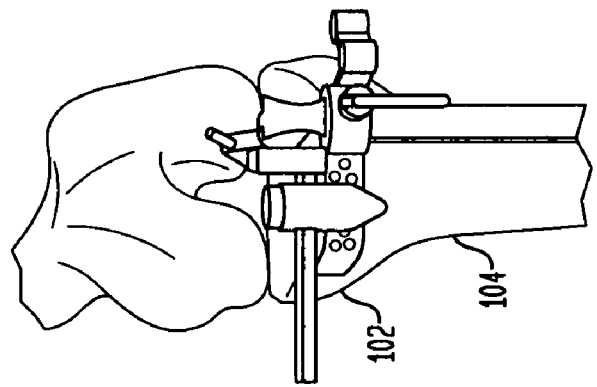
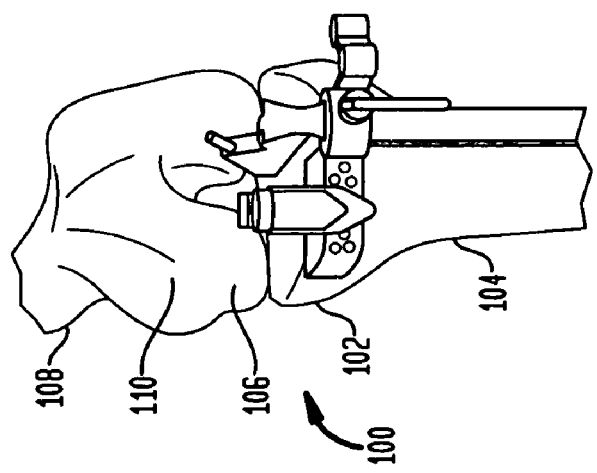

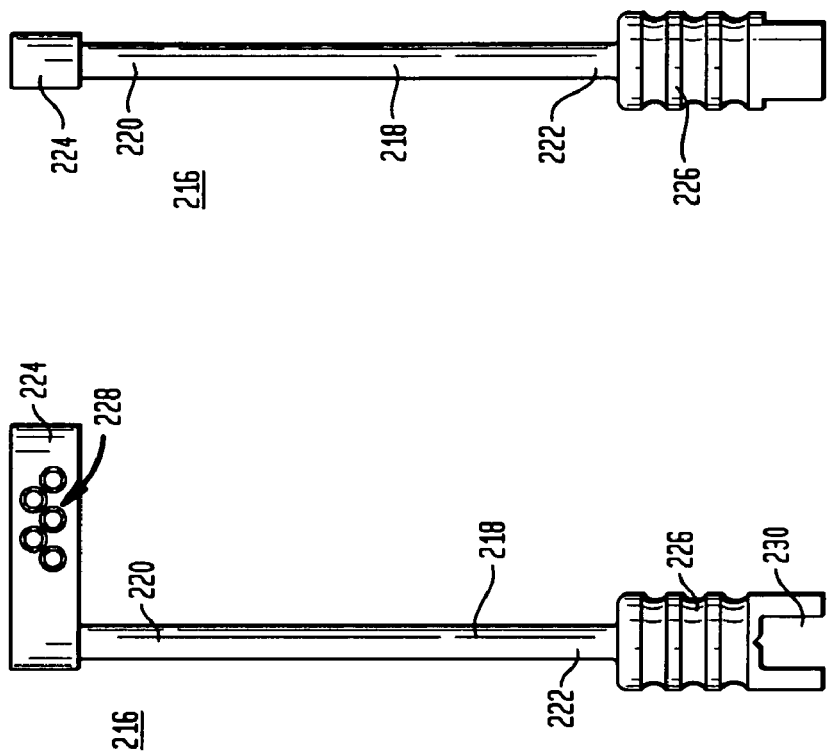

FIG. 12A
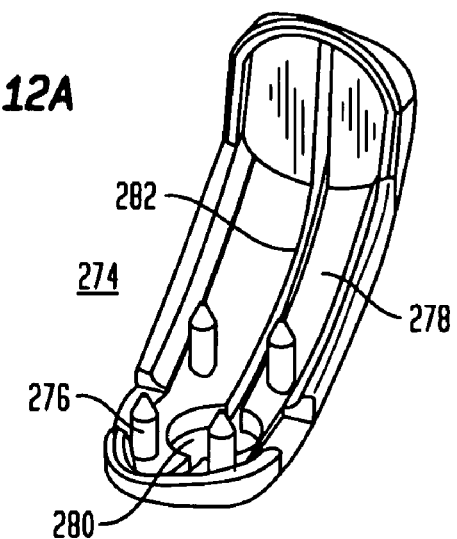
FIG. 12C
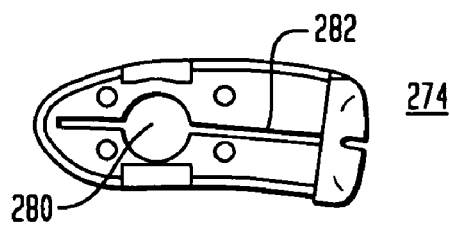
FIG. 12E  FIG. 12B  FIG. 12F
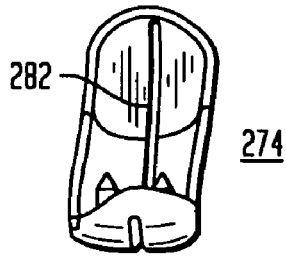 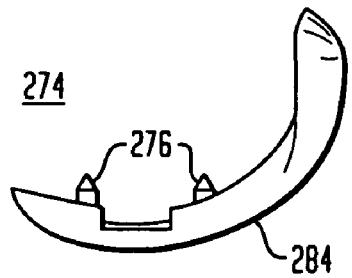 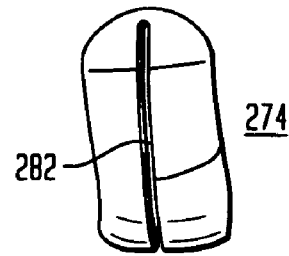
FIG. 12D
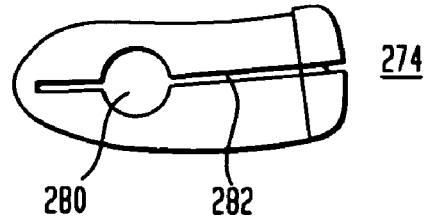

FIG. 14A
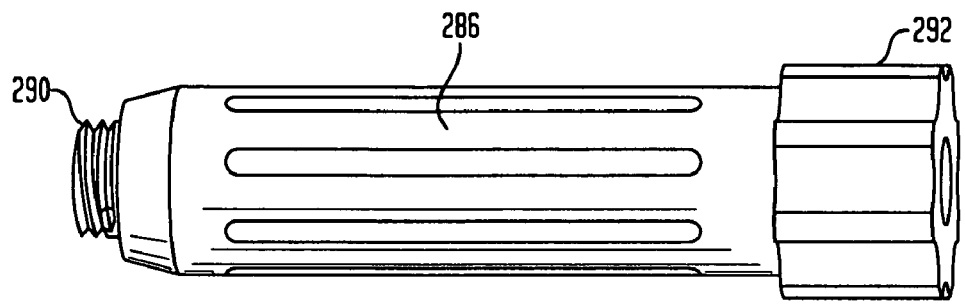
FIG. 14D   FIG. 14B
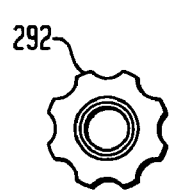 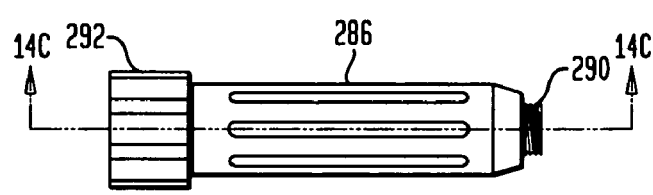
FIG. 14E
FIG. 14C
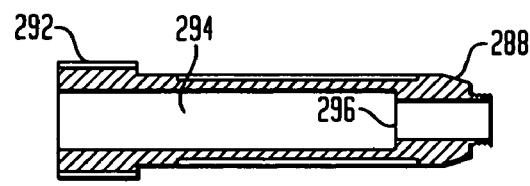

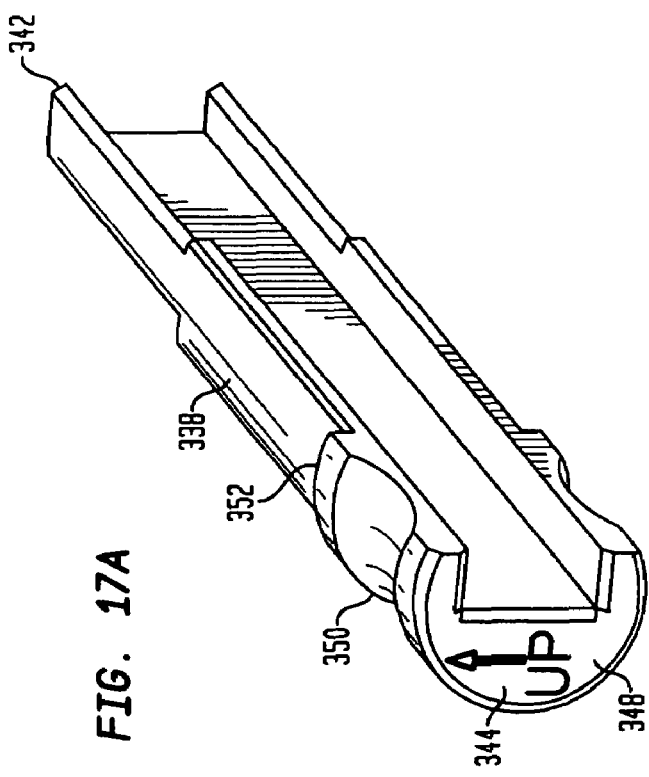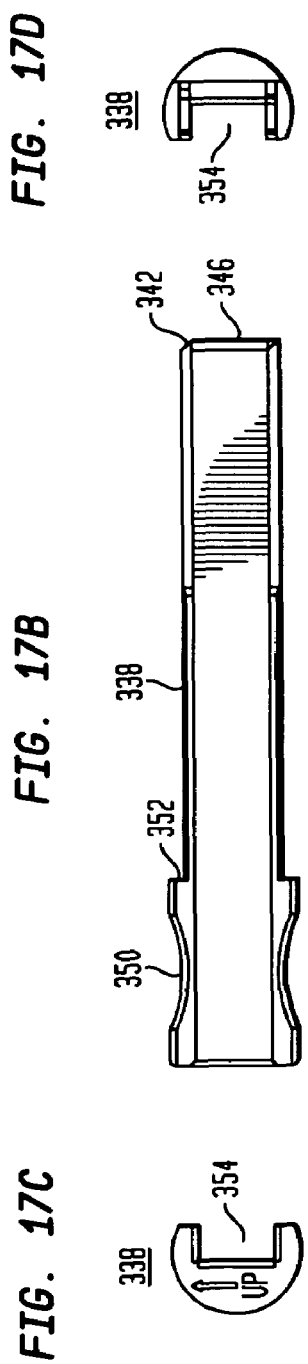

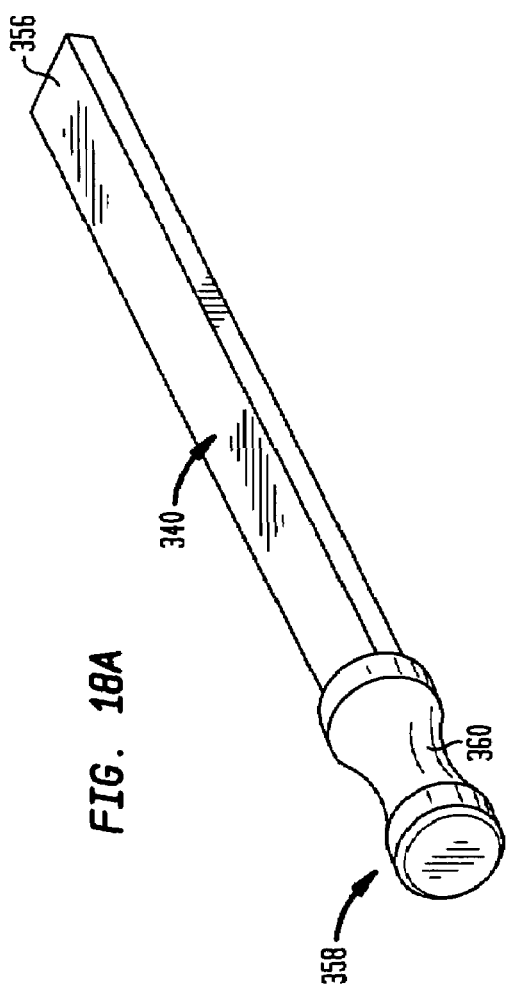
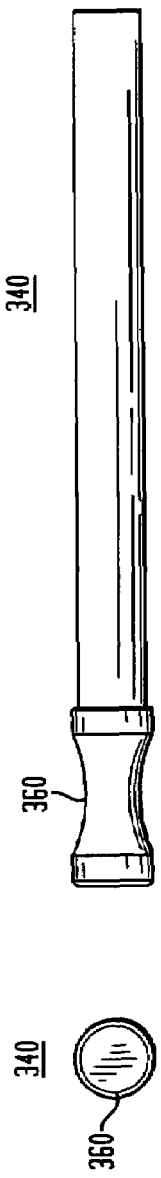
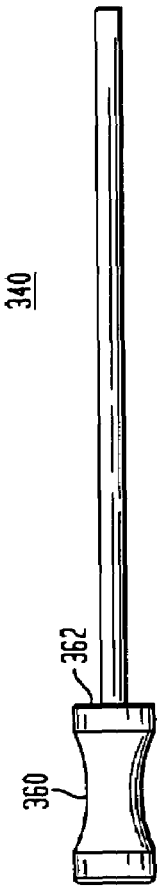
FIG. 18A
FIG. 18B
FIG. 18C
FIG. 18D

FIG. 65

GAP BALANCING TABLE

|  | FLEXION | | |
|---|---|---|---|
|  | TIGHT 4 mm | GOOD 6 mm | LOOSE 8 mm |
| EXTENSION TIGHT 4 mm | N/A | < POSTERIOR CONDYLE | << POSTERIOR CONDYLE |
| GOOD 6 mm | > POSTERIOR CONDYLE | N/A | < POSTERIOR CONDYLE |
| LOOSE 8 mm | >> POSTERIOR CONDYLE | > POSTERIOR CONDYLE | N/A |

UNICONDYLAR KNEE CUTTING GUIDE

CROSS REFERENCE TO RELATED APPLICATIONS

The present application is a continuation of U.S. patent application Ser. No. 11/471,931, filed Jun. 21, 2006, the disclosure of which is hereby incorporated by reference herein.

BACKGROUND OF THE INVENTION

The present invention generally relates to implants and more specifically relates to method and apparatus for preparing bone for receiving an implant.

The use of prosthetic implants to replace damaged natural joints, or portions of such joints, in the body has become widespread as medical and technological advances have joined to provide improved materials and configurations for prosthetic implants and innovative procedures for implanting these devices. The basic objective of such devices and procedures is to provide a repaired joint of maximum effectiveness, with a minimal intrusion into the body. Component parts of these prosthetic implants are utilized to replace portions of a natural joint which have become damaged, either through injury or disease, and it is usually necessary to remove portions of the natural joint beyond merely the damaged portions in order to enable stable and secure fixation of the component parts to the natural bone. In addition, access to damaged joints is limited and the necessity for reaching the areas to be worked upon can affect the extent of intrusion required to complete an effective implant.

Improved methods for implanting a prosthetic device are disclosed in commonly assigned U.S. Pat. No. 6,554,838, the disclosure of which is hereby incorporated by reference herein. In certain preferred embodiments of the '838 patent, a method for preparing a seating surface for an implant includes positioning a guide on bone, the guide having a guide slot following a path geometrically similar to the peripheral boundary of the seating surface, inserting a cutting device through the guide slot at any selected location along the path of the guide slot, and translating the cutting device along the guide slot to cut an outline groove in the bone coincident with the peripheral boundary of the seating surface. The guide is removed from the bone, and portions of the bone lying within the area delineated by the outline groove are removed to establish the seating surface. The methods disclosed in the '838 patent provide numerous advantages including minimizing the amount of natural bone that must be removed and attaining accuracy in the delineation of the area, depth and contour configuration of the prepared surfaces of the bone that will receive the implant In spite of the above advances, there remains a need for improved methods and apparatus for preparing bone for receiving implants and implanting the prosthetic devices.

SUMMARY OF THE INVENTION

In certain preferred embodiments of the present invention, a method of preparing a knee joint for receiving a unicondylar knee implant includes preparing a first seating surface at a proximal end of a tibia such as by resecting the proximal end of the tibia. The method desirably includes providing a combination bur template and spacer block. The bur template and spacer block are preferably integrally connected together. In certain preferred embodiments, the bur template and the spacer block are permanently connected together. The bur template and the spacer block desirably form a single, rigid element. The bur template preferably has an upper end, a lower end and a curved surface extending between the upper and lower ends thereof that is adapted to conform to a femoral condyle of a femur and the spacer block extends from the lower end of the bur template and has top and bottom surfaces.

The method desirably includes flexing the knee joint so that the prepared first seating surface at the proximal end of the tibia opposes a posterior region of the femur. The combination bur template and spacer block may be inserted into the knee joint so that the top surface of the spacer block engages the posterior region of the femur and the bottom surface of the spacer block engages the first seating surface at the proximal end of the tibia. While the spacer block is maintained between the femur and the tibia, the knee joint is extended until the curved surface of the bur template engages the femoral condyle of the femur. The bur template may be anchored to the femur, such as by using pins. The bur template is preferably used for guiding burring of the femoral condyle for preparing a second seating surface on the femur. After burring the femoral condyle of the femur, the posterior region of the femur is desirably resected.

The method may also include determining a distance between the first seating surface on the tibia and the posterior region of the femur, and selecting one of a plurality of combination bur template and spacer blocks for inserting into the knee joint. The spacer block of the selected bur template preferably has a thickness that matches the determined distance between the first seating surface on the tibia and the posterior region of said femur. In certain preferred embodiments, the thickness of the spacer block preferably corresponds to the thickness of a prostehtic device placed in the gap between the first seating surface on the tibia and the posterior region of the femur. The combination bur template and spacer block desirably includes an alignment feature. In certain preferred embodiments, the alignment feature is formed at a trailing end of the spacer block.

The method may also include inserting an alignment rail of a posterior resection guide locator into the alignment feature formed in the trailing end of the spacer block. The posterior resection guide locator desirably includes at least one pin opening that overlies the alignment rail. When the alignment rail is inserted into the alignment feature formed in the spacer block, the at least one pin opening of the posterior resection guide locator is preferably aligned with an opening of the bur template. A pin may be inserted through the at least one pin opening, through the opening in the bur template and anchored in the femur. In other preferred embodiments, two or more pins are inserted through two or more respective pin openings in the posterior resection guide locator.

The method may also include disengaging the posterior resection guide locator from engagement with the combination bur template and spacer guide and sliding a posterior resection guide over said at least one pin in said femur.

In other preferred embodiments of the present invention, a method of preparing seating surfaces in a knee joint for receiving a unicondylar knee implant includes preparing a first seating surface for receiving a tibial component at a proximal end of a tibia, flexing the knee joint so that the first seating surface opposes a posterior region of the femoral condyle, and providing a combination bur template and spacer block. The bur template preferably has a curved surface extending between upper and lower ends thereof and the spacer block desirably extends from the lower end of the bur template. The spacer block is preferably inserted into the knee joint so that the spacer block engages the posterior region of the femoral condyle and the first seating surface on the tibia.

While the spacer block is maintained between the femur and the tibia, the knee joint is desirably extended until the curved surface of the bur template engages a distal region of the femoral condyle.

The method may include using the bur template to guide burring of the distal region of the femoral condyle for preparing a second seating surface for receiving a femoral component. After the second seating surface has been prepared, one or more alignment pins may be anchored in the femoral bone at the second seating surface. The one or more alignment pins anchored in the femoral bone may be used for aligning a posterior resection guide with the posterior region of the femoral condyle. The posterior resection guide preferably has a slot for guiding a cutting instrument. The posterior resection guide is desirably used for resecting the posterior section of the femur.

In other preferred embodiments of the present invention, a kit for preparing a knee joint for receiving a unicondylar knee implant includes a combination bur template and spacer block having a bur template with an upper end, a lower end and a curved inner surface extending between the upper and lower ends thereof, and a spacer block extending from the lower end of said template. The spacer block may have a top surface, a bottom surface, a leading end for insertion into a knee joint and a trailing end spaced from the leading end and adjacent the lower end of the bur template. The trailing end of the spacer block preferably includes an opening with an alignment feature that extends from the trailing end of the spacer block toward the leading end of the spacer block.

The kit may also include a posterior resection guide locator having an alignment rail insertible into the opening at the trailing end of the spacer block. The alignment rail is preferably adapted to mesh with the alignment feature in the opening of the spacer block. In certain preferred embodiments, the alignment rail has an elongated projection and the alignment feature in the spacer block has an elongated groove that receives the elongated projection. In other preferred embodiments, the alignment rail may have an elongated groove and the alignment feature in the spacer block may have an elongated projection that fits into the groove.

The posterior resection guide locator preferably includes an alignment pin guide overlying the alignment rail. The alignment pin guide desirably includes at least one pin opening extending therethrough.

The bur template preferably includes a guide rail extending around an outer perimeter thereof and a central opening surrounded by the guide rail. The at least one pin opening of the alignment guide is preferably aligned with the central opening when the alignment rail is inserted into the opening of the spacer block. An alignment pin is insertible into the at least one pin opening of the alignment guide.

The kit may also include a posterior resection guide having an upper end, a lower end having an elongated opening for receiving a cutting tool and a pin opening between the upper and lower ends. The pin opening of the posterior resection guide is desirably slidable over the alignment pin. The pin opening may include a first set of pin openings and a second set of pin openings that is closer to the upper end of the posterior resection guide than the first set of pin openings. The pin opening may also include a third set of pin openings that is closer to the lower end of the posterior resection guide than the first set of pin openings. As will be described in more detail below, the different sets of pin openings may be used for adjusting the amount of bone resected from the posterior region of the femoral condyle.

These and other preferred embodiments of the present invention will be described in more detail below.

BRIEF DESCRIPTION OF THE DRAWINGS

FIGS. 1A-1J show a method of preparing a knee to receive a unicondylar knee implant, in accordance with certain preferred embodiments of the present invention.

FIGS. 8A-8E show an alignment tower, in accordance with preferred embodiments of the present invention.

FIGS. 12A-12F show a femoral trial cutting guide, in accordance with certain preferred embodiments of the present invention.

FIGS. 14A-14E show the handle of FIG. 13A.

FIGS. 17A-17D show a chisel for use with the punch tower shown in FIGS. 15A-15D.

FIGS. 18A-18D show a tamp for use with the punch tower shown in FIGS. 15A-15D.

FIG. 65 shows a gap balancing table, in accordance with certain preferred embodiments of the present invention.

DETAILED DESCRIPTION

Figure 1E:
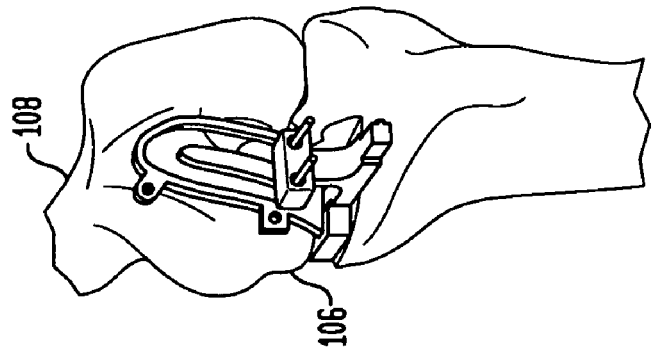

FIGS. 1A-1J show a method of preparing a knee for receiving an implant, in accordance with certain preferred embodiments of the present invention. In particular preferred embodiments, the method is used for preparing a knee to receive a knee implant such as a unicondylar knee implant. Referring to FIG. 1A, a knee joint 100 is located between a proximal end 102 of a tibia 104 and a distal end 106 of a femur 108. The distal end 106 of the femur 108 includes a distal condyle 110, which is the curved surface on a bone where it forms a joint with another bone. The femur 108 also has a posterior region of the femoral condyle.

Figure 1F:
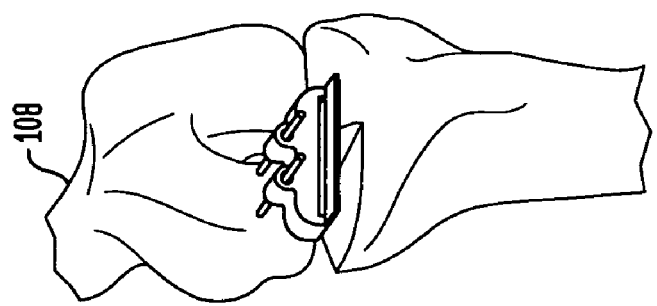
Figure 1G:
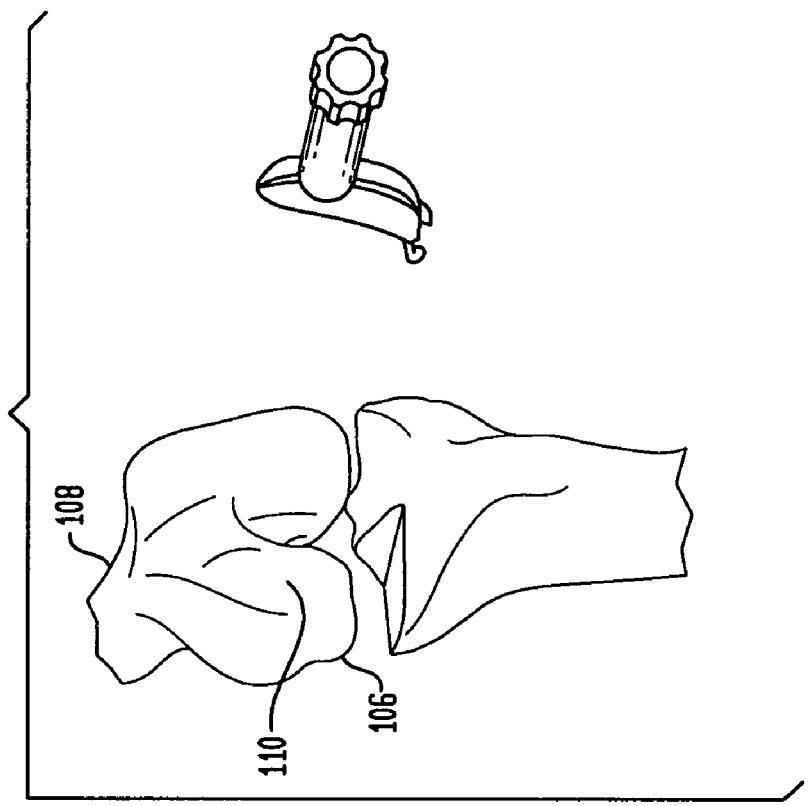
Figure 1H:
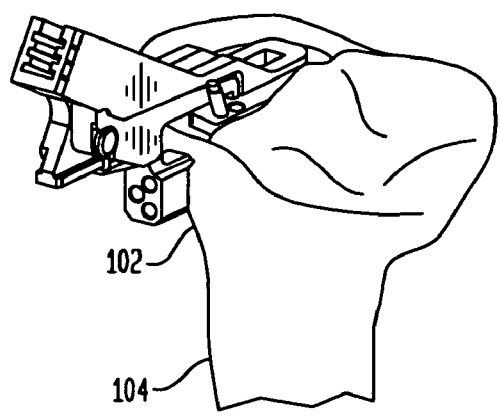
Figure 1I:
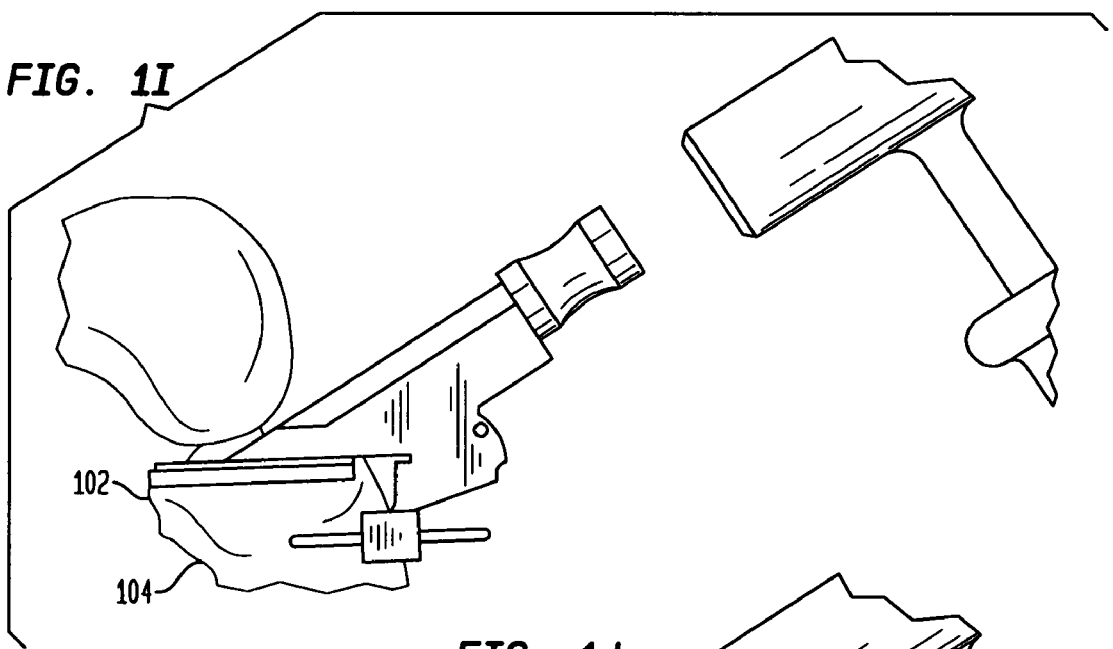
Figure 1J:
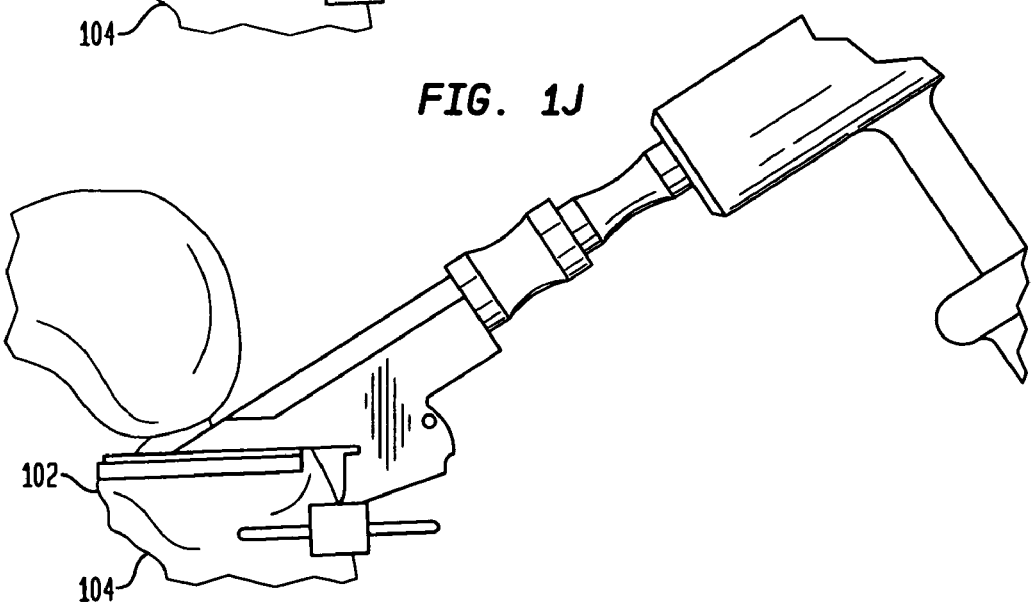

In FIG. 1A, a tibial resection is performed on the proximal end 102 of the tibia 104. FIG. 1B shows a sagittal resection being performed on the proximal end 102 of the tibia 104. FIG. 1C shows the positioning and alignment of a combination bur template and spacer block in a knee joint. The combination bur template and spacer block includes a spacer block that is inserted into the knee joint between the femur and the tibia and the bur template that guides burring of the condyle at the distal end of the femur. The bur template and spacer block is aligned with femur 108 using an alignment flag, as will be described in more detail below. FIG. 1D shows the bur template/spacer block after it has been positioned in a knee joint. The bur template includes a rail that surrounds a central opening. The rail preferably guides movement of a burring instrument after the burring instrument is passed through the central opening of the bur template. FIG. 1E shows a posterior resection guide locator assembled with the combination bur template and spacer guide and alignment pins extending through pin openings in the posterior resection guide locator. FIG. 1F shows the alignment pins shown in FIG. 1E being used to align a posterior resection guide for performing a posterior resection of the femur 108. FIG. 1G shows a femoral trial cutting guide used for forming post and fin openings on the condyle 110 located at the distal end 106 of the femur 108. FIGS. 1H-1J show a method of forming a keel opening at the proximal end 102 of the tibia 104.

Figure 2:
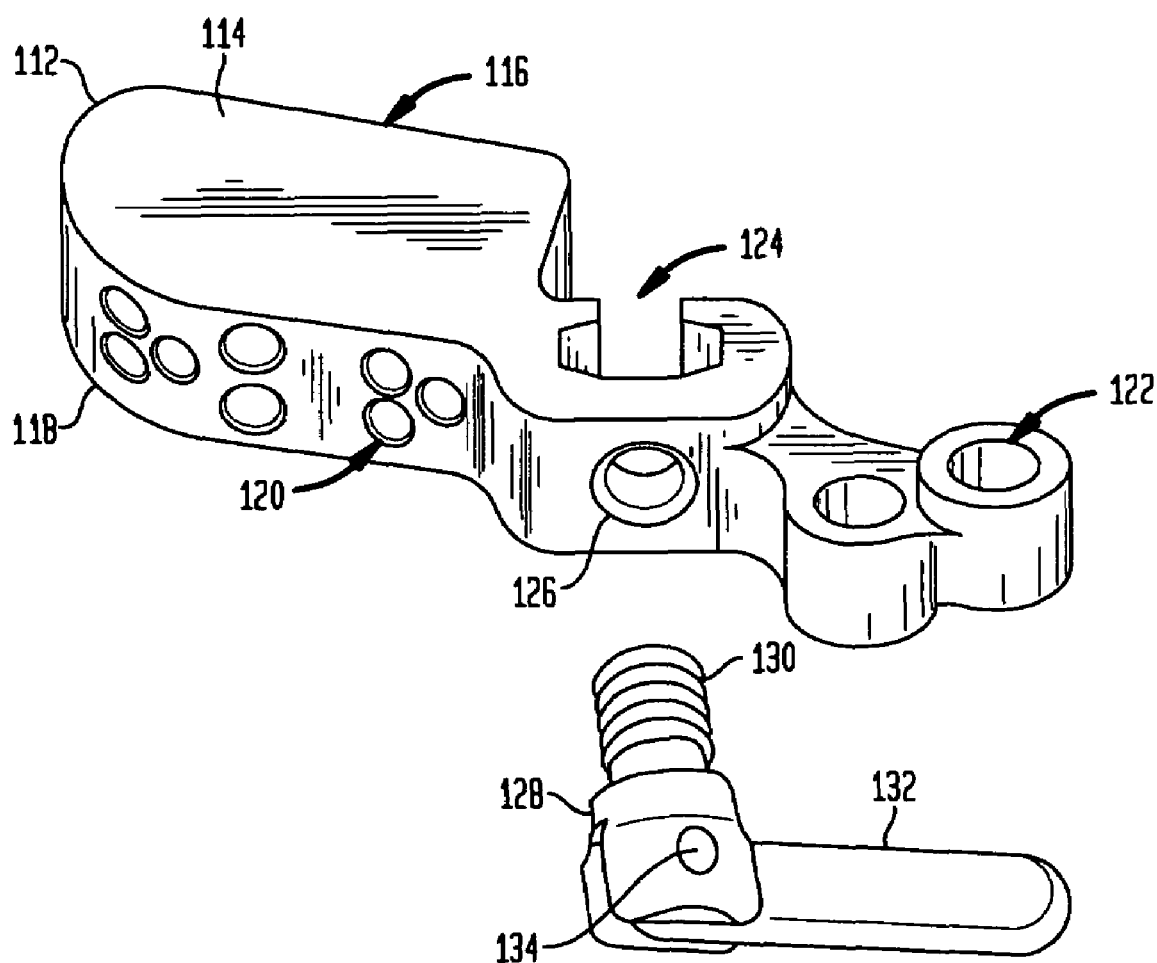
FIG. 2 shows a tibial resection block and a locking element securable thereto, in accordance with certain preferred embodiments of the present invention.

Referring to FIG. 2, in certain preferred embodiments of the present invention, a system for preparing a knee joint for receiving a unicondylar knee implant includes a tibial resection block 112 having a top surface 114, an inner contoured surface 116 that is preferably shaped to fit against the proximal end of a tibia and an outer contoured surface 118 that is adapted to fit easily within an incision. The tibial resection block 112 has a universal design so that it may be used on the left or right side of the knee, thereby minimizing the number of parts that are required. The tibial resection block is preferably used to perform a tibial resection at a proximal end of a tibia. The tibial resection block desirably includes one or more holes 120 that may receive fasteners such as pins for securing the tibial resection block to bone. One or more of the holes 120 may be adapted to secure a tool thereto, as will be described in more detail below. The tibial resection block also preferably includes one or more openings 122 adapted to secure a navigation tracker for properly aligning the tibial resection block relative to the proximal end of a tibia.

The tibial resection block 112 also preferably includes a C-shaped opening 124 engagable with an elongated element such as a rod. After the rod is coupled with the C-shaped opening 124, the tibial resection block is designed to slide along the rod for adjusting the location of the tibial resection block relative to the proximal end of the tibia. The tibial resection block 112 may also include a threaded opening 126 aligned with the C-shaped opening 124. A tightening screw 128 has threads 130 that are preferably received within the threaded opening 126. The tightening screw 128 also includes a lever 132 that may pivot about a pivot point 134 for enabling greater leverage to be applied to the tightening screw. The pivotable lever also preferably allows the screw 128 and the lever 132 to remain below the resection surface.

Figure 3A:
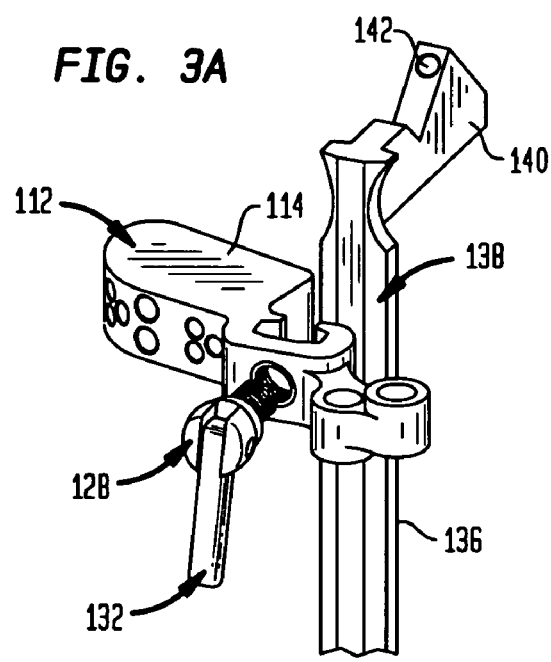
FIGS. 3A-3D show the tibial resection block of FIG. 2 secured to a rod, in accordance with certain preferred embodiments of the present invention.
Figure 3B:
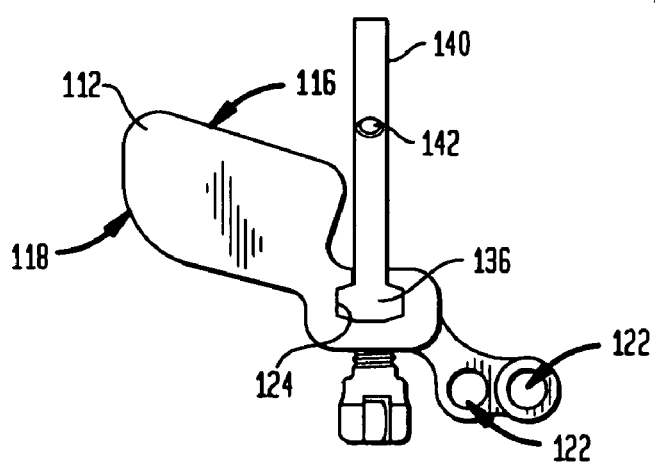

Referring to FIGS. 3A-3D, the tibial resection block 112 is securable to a rod 136 having a proximal end 138 and a lower end (not shown). The lower end of the rod may be connected to an ankle clamp for stabilizing the rod. Referring to FIG. 3B, the rod 136 is preferably secured within the C-shaped opening 124 of the tibial resection block 112, with the inner contoured surface 116 facing the tibia and the outer contoured surface 118 facing away from the tibia. The proximal end 138 of the rod 136 includes a flange 140 having a pin opening 142 for anchoring the rod to the proximal end of a tibia so as to further enhance the stability of the rod 136 and the tibial resection block 112. The tibial resection block 112 also desirably includes one or more navigation tracker openings 122 for properly aligning the tibial resection block with the surface to be resected.

Figure 3C:
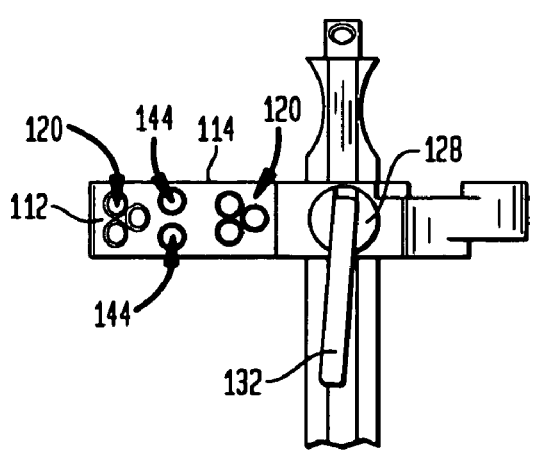
Figure 3D:
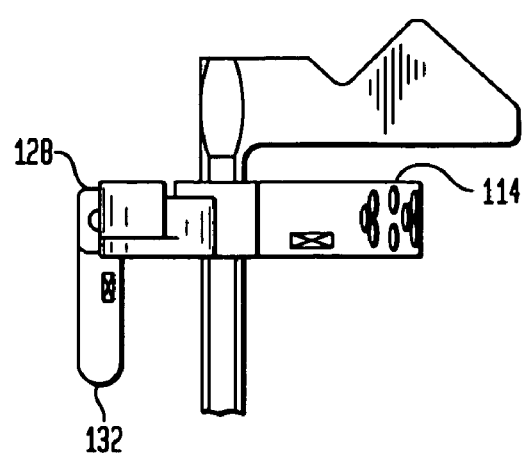

Referring to FIGS. 3A, 3C and 3D, after the top surface 114 of the tibial resection block 112 is positioned at a correct height relative to the proximal end of the tibia, the lever 132 may be grasped for tightening the tightening screw 128 so as to lock the position of the tibial resection block relative to the rod 136.

Referring to FIG. 3C, in order to more firmly secure the position of the tibial resection block 112 relative to the proximal end of the tibia, one or more securing elements such as pins may be passed through the outer openings 120. The central openings 144 may be used for alignment pins or for securing tools to the tibial resection block, such as securing a stylus to the tibial resection block.

Figure 4:
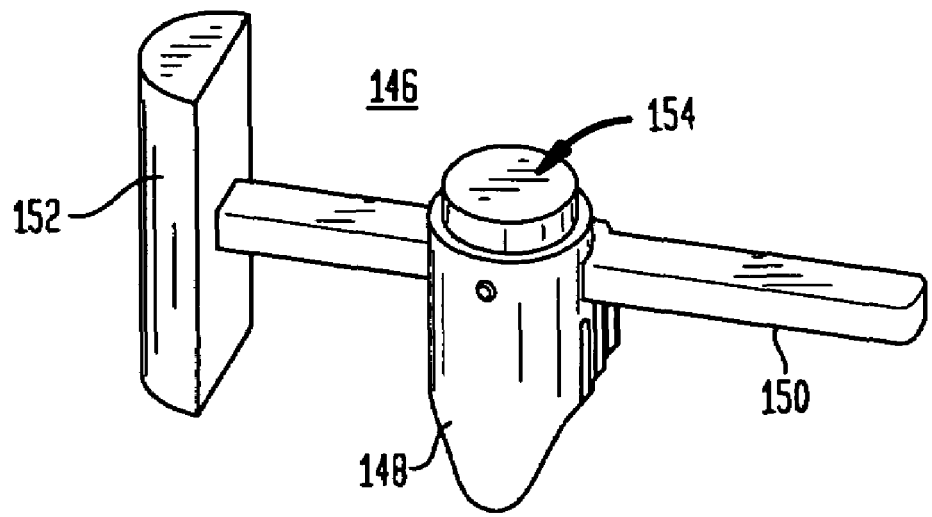
FIG. 4 shows a sagittal resection alignment guide, in accordance with certain preferred embodiments of the present invention.

FIG. 4 shows a sagittal resection alignment guide 146 that is securable to the tibial resection block 112 shown in FIGS. 2 and 3A-3D. The sagittal resection alignment guide 146 preferably includes a main body 148, an elongated rod 150 that slides through an opening in the main body and an alignment block 152 secured to an end of the elongated rod 150. The alignment guide 146 also includes a depressible button 154 that may be depressed for allowing the rod 150 to move relative to the main body 148. The sagittal resection alignment guide 146 may include projections, such as posts or hooks (not shown), that engage one or more of the openings in the tibial resection block shown above in FIG. 2.

Referring to FIGS. 5A-5E, in certain preferred embodiments of the present invention, a modular handle 156 for inserting a combination bur guide and spacer block includes a handle portion 158 having an upper end secured to an alignment element 160 having a leading end 162 and a trailing end 164. The leading end 162 of the alignment element 160 preferably includes a male projection 166 on one lateral side thereof and a pin 168 on an opposite side thereof. Modular handle 156 also includes a male end connector 169 projecting from the second end 164 of the alignment element 160. The modular handle 156 also includes a depressible button 170 and a spring 172 coupled therewith. The depressible button 170 may be depressed for interacting with the pin 168. In one button position, the pin 168 is free to move inwardly in pin opening 174. When the button 170 is not depressed, however, the pin is locked outwardly and may not retract within the opening 174.

Figure 6A:
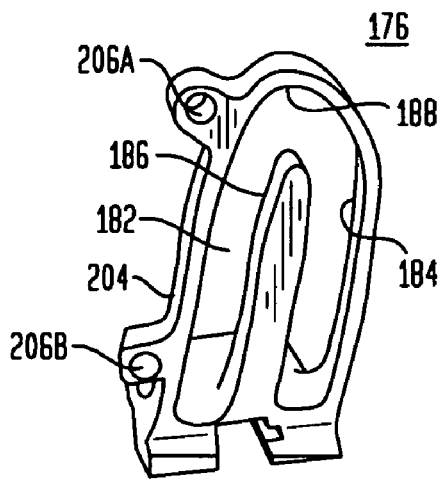
FIGS. 6A-6H show a combination bur template and spacer block, in accordance with certain preferred embodiments of the present invention.
Figure 6B:
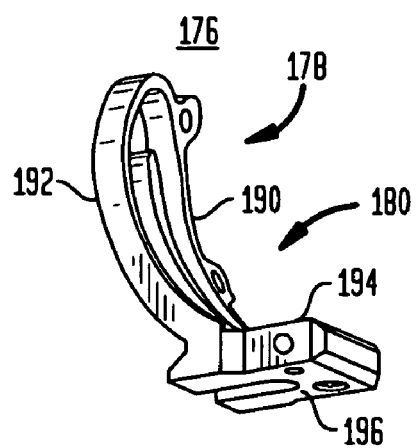
Figure 6C:
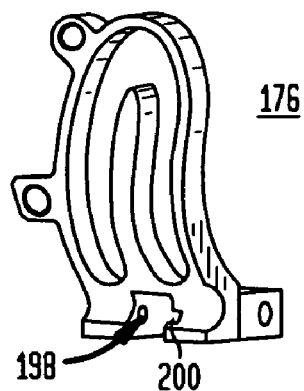
Figure 6F:
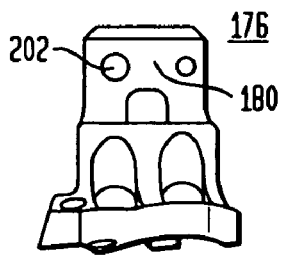
Figure 6G:
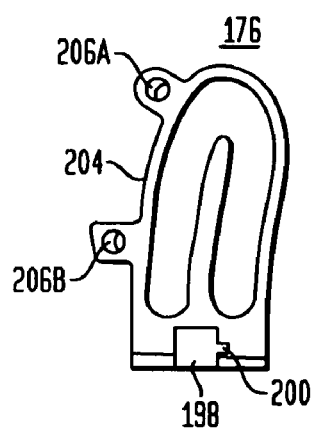
Figure 6D:
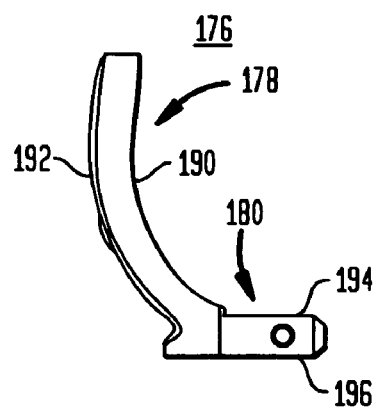
Figure 6E:
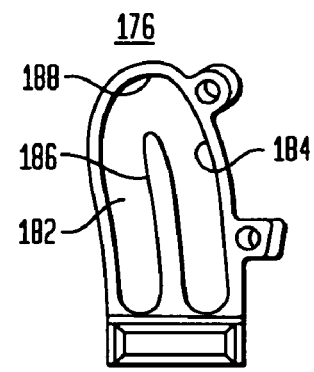
Figure 6H:
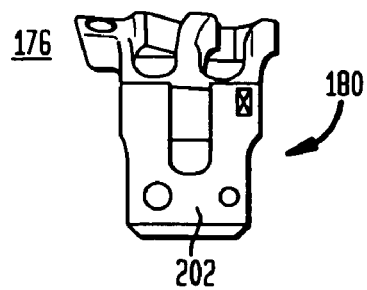
Figure 7A:
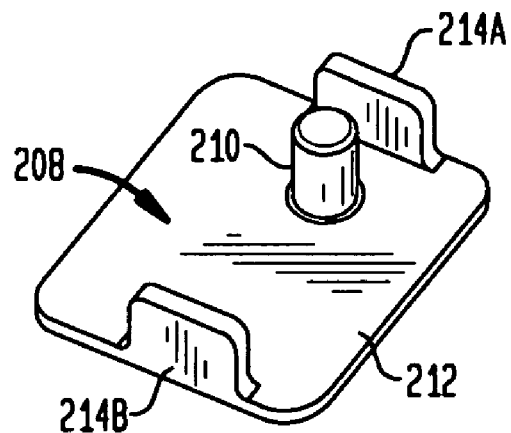
FIGS. 7A-7D show a shim engageable with the combination bur template and spacer block shown in FIGS. 6A-6H, in accordance with certain preferred embodiments of the present invention.
Figure 7B:
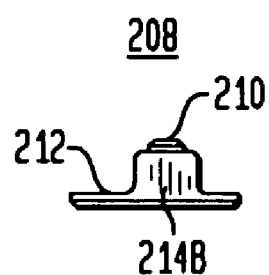
Figure 7C:
Figure 7D:
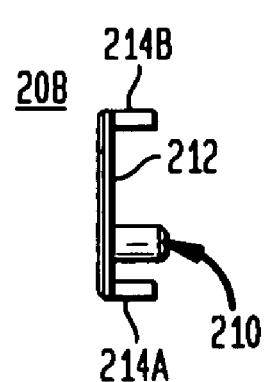

Referring to FIGS. 6A-6H, in accordance with certain preferred embodiments of the present invention, a bur template/spacer block 176 includes a bur template portion 178 for guiding burring of femoral bone and a spacer block portion 180 insertible into a knee joint. Referring to FIGS. 6A and 6E, the bur template/spacer block 178 includes a slot 182 that defines an outer surface 184, an inner surface 186 and an apex 188. The bur portion 178 includes an inner surface 190 and an outer surface 192. The inner and outer surfaces 190, 192 are preferably curved to conform to the condyle at a distal end of a femur. The spacer portion 180 includes a top surface 194 and a bottom surface 196 remote therefrom. Depending upon the gap between the femur and the tibia, a plurality of spacer blocks may be provided having varying thicknesses. In certain preferred embodiments, spacer blocks are available having thicknesses of between 4-14 mm and more preferably 6-12 mm. Referring to FIGS. 6C and 6G, the spacer block portion 176 has an opening 198 extending from a trailing end of the spacer block toward a leading end of the spacer block. The opening 198 preferably has an elongated alignment groove 200 extending along one side thereof. Referring to FIGS. 6F and 6H, the spacer block portion 180 has at least one post opening 202 extending between the top and bottom surfaces 194, 196. Referring to FIGS. 6A and 6G, the outer rail 204 of the bur template portion 178 includes pin fixation flanges 206A, 206B. The pin fixation flanges include openings extending therethrough that are adapted to receive securing elements such as pins so that the bur template may be anchored to bone.

Referring to FIGS. 7A-7D, in accordance with certain preferred embodiments of the present invention, the system includes a shim 208 having a posts 210 projecting from a first surface 212 thereof. The shim 208 includes opposing sidewalls 214A, 214B. As will be described in more detail below, the shim may be assembled over either the top surface or the bottom surface of the spacer block portion of the bur template/spacer block shown in FIGS. 6A-6H for adjusting the position of the bur template/spacer block. The shim may also be used for adjusting the thickness of the spacer block. In certain preferred embodiments, more than one shim may be connected with the spacer block.

Referring to FIGS. 8A-8E, in accordance with certain preferred embodiments of the present invention, the system includes an alignment tower 216 that may be coupled with the modular handle shown in FIGS. 5A-5E for inserting and aligning the bur template/spacer block in a knee joint. Referring to FIGS. 8A, 8B and 8E, the alignment tower 216 preferably includes a shaft 218 having an upper end 220 and a lower end 222. Referring to FIGS. 8A-8E, the alignment tower includes an alignment flag 224 secured to the upper end 220 of the shaft 218 and a connection member 226 secured to the lower end of the shaft 218. Referring to FIGS. 8A and 8B, the alignment flag 224 includes a number of holes 228 extending therethrough that are used for approximating the center of a knee. In certain preferred embodiments, an alignment rod can be passed through one or more of the holes 228 in the flag 224 for locating or approximating the center of the knee. Referring to FIGS. 8A, 8B and 8D, the connection member 226 at the lower end includes a C-shaped opening 230 having a centrally located well 232 and an elongated groove 234 extending from opposite sides of the well 232. The central well 232 is adapted to fit over the male end connector 169 of the modular handle 158 FIGS. 5A-5E).

Figure 9A:
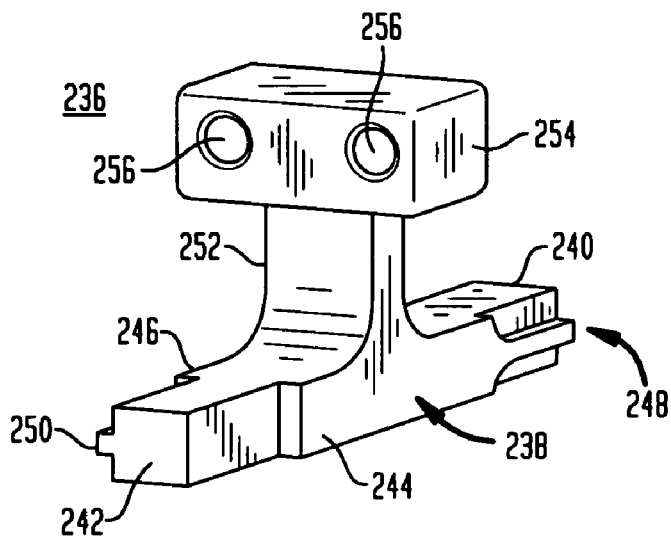
FIGS. 9A-9E show a posterior resection guide locator, in accordance with certain preferred embodiments of the present invention.
Figure 9B:
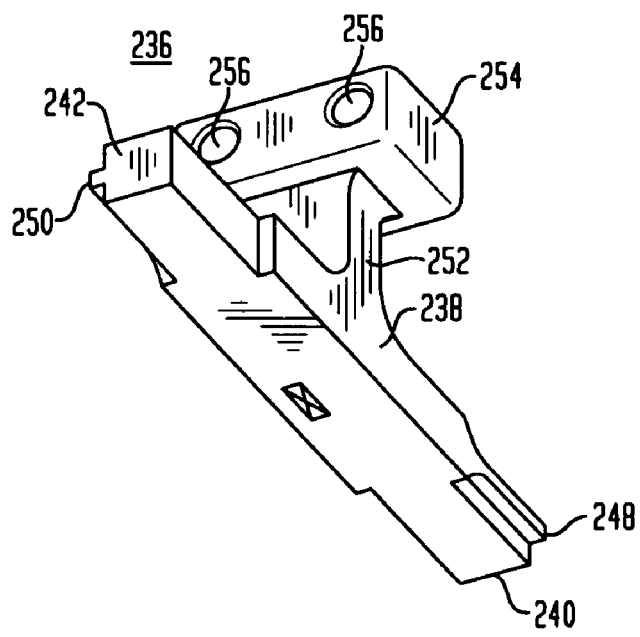
Figure 9C:
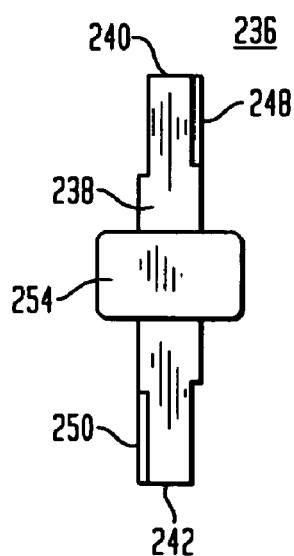
Figure 9E:
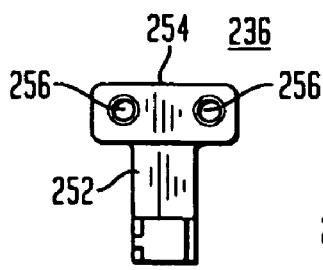
Figure 9D:
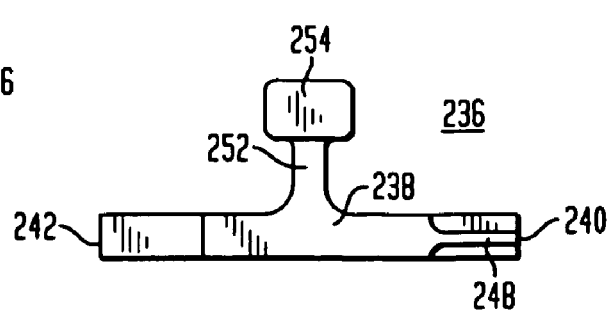
Figure 10A:
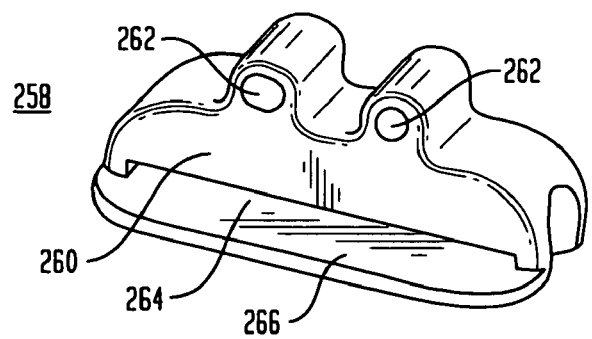
FIGS. 10A-10D show a posterior resection guide, in accordance with certain preferred embodiments of the present invention.
Figure 10B:
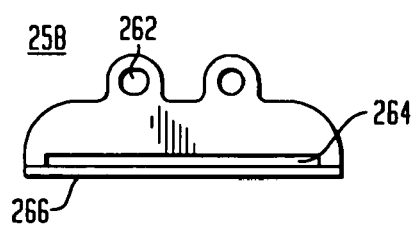
Figure 10C:
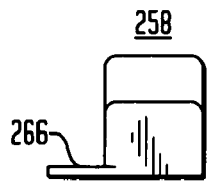
Figure 10D:
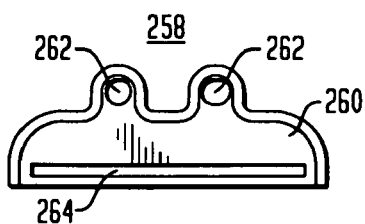

Referring to FIGS. 9A-9E, in accordance with certain preferred embodiments of the present invention, the system includes a posterior resection guide locator 236. Referring to FIGS. 9A, 9B and 9D, the posterior resection guide locator includes an alignment rail 238 having a first end 240 and a second end 242. The alignment rail 238 also desirably includes a first lateral surface 244 and a second lateral surface 246 extending on opposite sides of the alignment rail 238 between the first and second ends 240, 242 thereof. The alignment rail 238 includes a first male projection 248 provided adjacent the first end 240 and a second male projection 250 provided adjacent the second end 242. The male projections 248, 250 are sized to fit into the elongated alignment groove 200 (FIG. 6G) provided at the trailing end of the spacer block. The particular first end 240 or second end 242 of the rail 238 that is inserted into the alignment groove 200 may depend upon the type of operation being conducted. For example, the first end 240 may be inserted in the groove 200 for a LM/RL procedure and the second end 242 may be inserted in the groove 200 for a RM/LL procedure.

Referring to FIGS. 9A-9E, the posterior resection guide locator 236 includes a support element 252 and a pin guide 254 mounted atop the support element 252. The pin guide 254 preferably includes one or more pin holes 256 extending therethrough. As will be described in more detail below, after the posterior resection guide locator is coupled with the elongated alignment groove in the bur template/spacer block shown in FIGS. 6A-6H, the pin holes 256 are aligned with the opening in the bur template portion and alignment pins are inserted into bone through the pinholes 256. The alignment pins are preferably used to align a posterior resection guide for conducting a posterior resection of the femur, as will be described in more detail below.

Referring to FIGS. 10A-10D, in accordance with certain preferred embodiments to the present invention, the assembly includes a standard posterior resection guide 258 including a main body 260 having an upper end with pin holes 262 and a lower end with a slot 264 extending therethrough. The slot 264 is preferably a captured slot that is bounded on left and right sides thereof by the main body 260. As a result, a cutting instrument such as a saw placed into the slot cannot extend beyond the left and right boundaries of the main body. The posterior resection guide also includes a ledge 266 that projects from one side of the slot 264. The combination of the ledge 266 and the captured slot 264 control movement of a cutting blade so as to accurately control the cut through a posterior region of the femoral condyle. In certain preferred embodiments of the present invention, the standard posterior resection guide 258 is sized and configured to remove 6 mm of bone from the posterior region of the femoral condyle, which matches the 6 mm thickness of the femoral component of the implant. The size and configuration of the standard posterior resection guide may be varied so that the amount of bone to be removed matches the thickness of the femoral component.

Figure 11A:
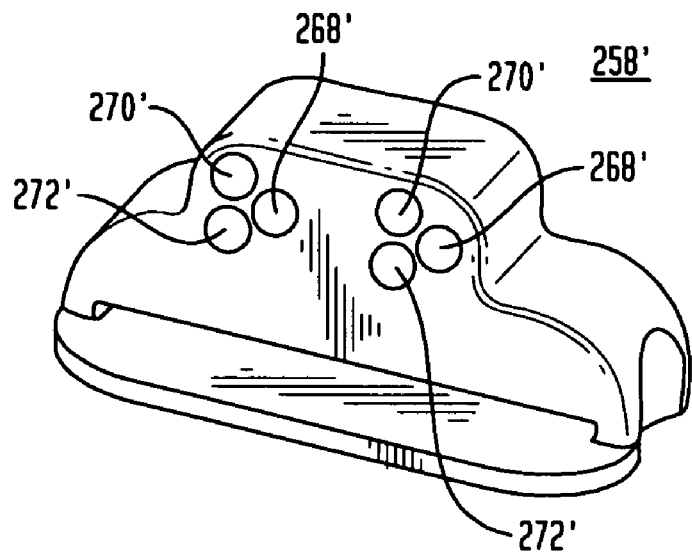
FIGS. 11A-11C show a posterior resection guide, in accordance with other preferred embodiments of the present invention.
Figure 11B:
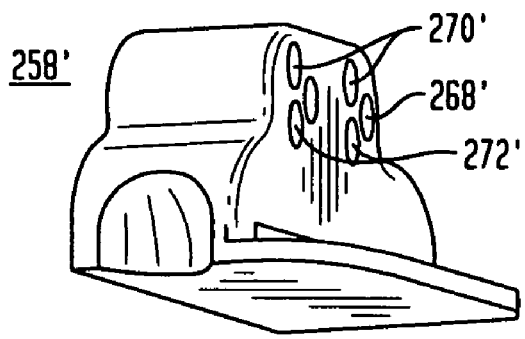
Figure 11C:
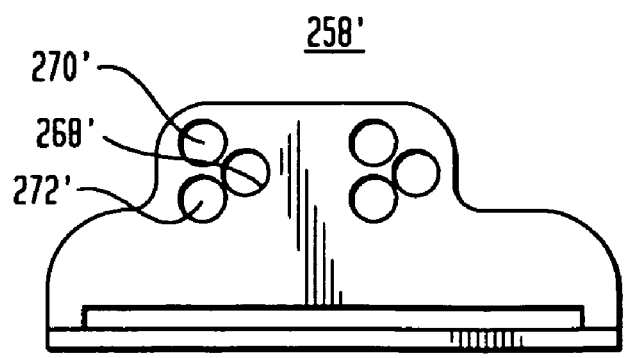

FIGS. 11A-11C show a posterior resection guide 258', in accordance with another preferred embodiment of the present invention. The posterior resection guide 258' is generally similar to the standard posterior resection guide shown in FIGS. 10A-10D, however, it includes three different sets of pin holes. The first set of pin holes 268' is used for performing a standard posterior resection, which in certain preferred embodiments is 6 mm. A second set of pin holes 270' is used when the resection guide must be lowered when performing a posterior resection for reducing the amount of bone removed from the posterior region of the femur. A third set of pin holes 272' is used when the resection guide must be raised when performing a posterior resection for increasing the amount of bone removed from the posterior region of the femur. As will be described in more detail below, it may be necessary to raise or lower the posterior resection guide 258' from a standard resection (e.g. removing 6 mm of bone from the posterior region of the femoral condyle) in order to balance the gap of a knee joint when in an extended position and a flexed position. The posterior resection guide may be raised or lowered so that the gap in extension is equal to the gap in flexion and vice versa. As is well known to those skilled in the art, uneven gaps may result in flexion instability or extension instability.

Referring to FIGS. 12A-12F, in certain preferred embodiments of the present invention, the system includes a femoral trial cutting guide 274 for preparing the distal end of the femur to receive the femoral component of the implant. The femoral trial cutting guide 274 desirably includes a set of anchoring pins 276 projecting from an inner face 278 thereof. The cutting guide 274 also desirably includes a central opening 280 extending therethrough and an elongated slot 282 that intersects the central opening 280. The elongated slot preferably extends between upper and lower ends of the cutting guide 274. After the condyle at the distal end of a femur has been burred using the bur template portion of the bur template/spacer block shown above, the inner face 278 of the cutting guide 274 is abutted against the burred surface of the femur. The pins 276 are preferably inserted into bone for holding the cutting guide in place. An impactor may be used to advance the anchor pins 276 into the bone. A drill may be inserted through the central opening 280 to form a post opening for an implant peg. In addition, a cutting instrument, such as a saw or cutting blade, may be inserted through the elongated slot 282 to form a keel opening for an implant.

Referring to FIG. 12B, the cutting guide 274 preferably has an outer surface that is curved. The curved outer surface of the cutting guide may be used to perform a range of motion test. After the post and keel openings have been formed, and a range of motion test is completed, the cutting guide 274 may be removed from its attachment to the femoral bone.

Figure 13A:
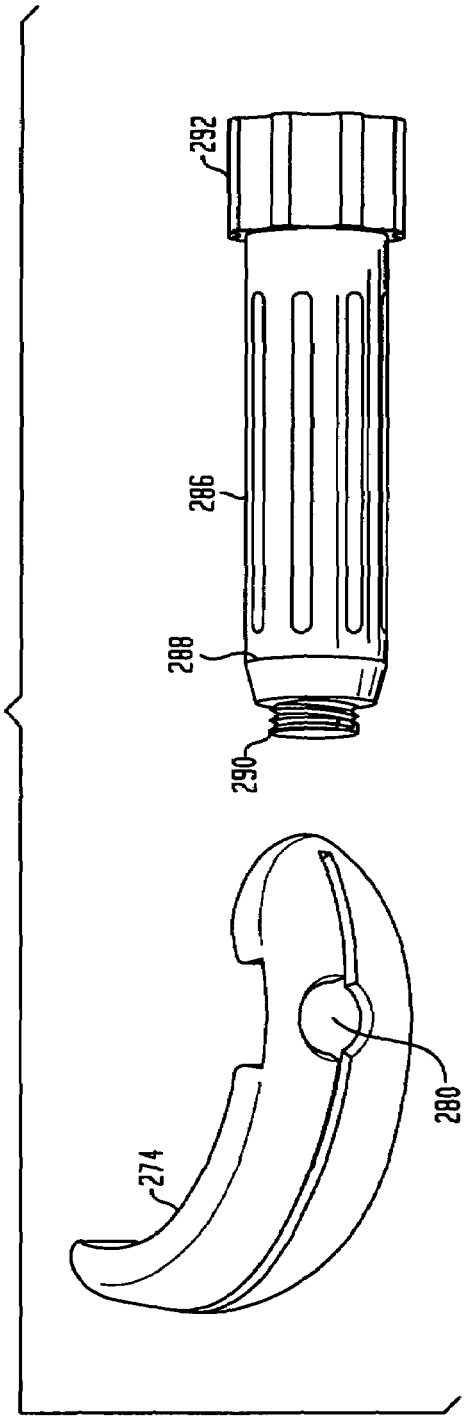
FIG. 13A shows a handle attachable to the femoral trial cutting guide of FIGS. 12A-12F, in accordance with certain preferred embodiments of the present invention.
Figure 13B:
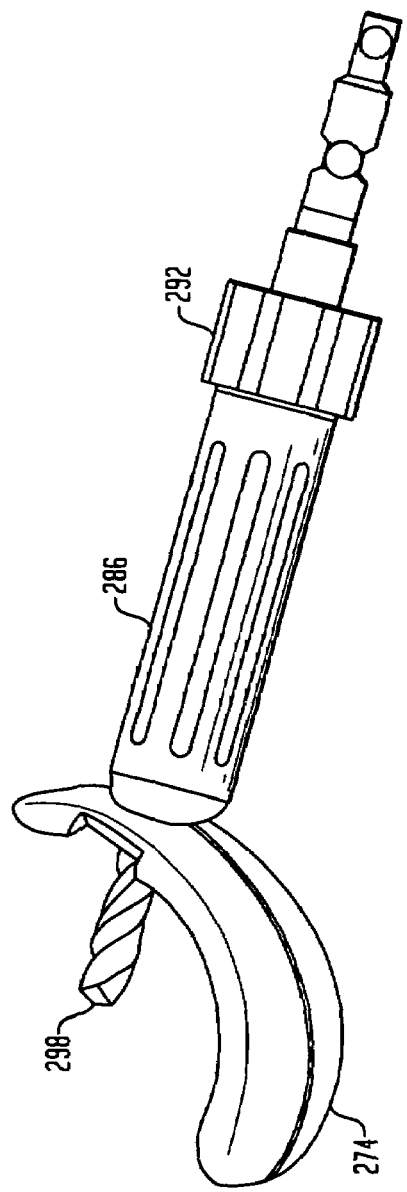
FIG. 13B shows a drill passable through an opening in the femoral trial cutting guide of FIGS. 12A-12F and the handle of FIG. 13A.

Referring to FIG. 13A, in certain preferred embodiments, the system includes a drill guide 286 having a first end 288 with a threaded projection 290 and a second end 292 including a handle. Referring to FIGS. 14A-14E, the drill guide 286 has a central opening 294 extending between the first end 288 and the second end 292. The opening 294 includes a reduced diameter area or shelf 296 that limits forward movement of a drill. Referring to FIGS. 13A-13B and 14C, after the threaded projection 290 of the drill guide 286 is threaded into central opening 280 of the cutting guide 274, a drill bit 298 may be passed through the opening 294 of the drill guide 286 until a portion of the drill abuts against the shelf 296 for limiting further advancement of the drill bit 298. The drill may be operated for forming a post opening in the femoral bone. The post opening, as will be described in more detail below, is adapted to receive a post of a permanent femoral component of an implant. After the post hole has been formed, the drill bit 298 may be removed from the drill guide 286. The handle 292 of the drill guide may be grasped to remove the cutting guide 274 from its attachment to the femoral bone. In certain preferred embodiments, the drill guide 286 may be used as an impaction/extraction handle for a trial such as a femoral trial.

Figure 15A:
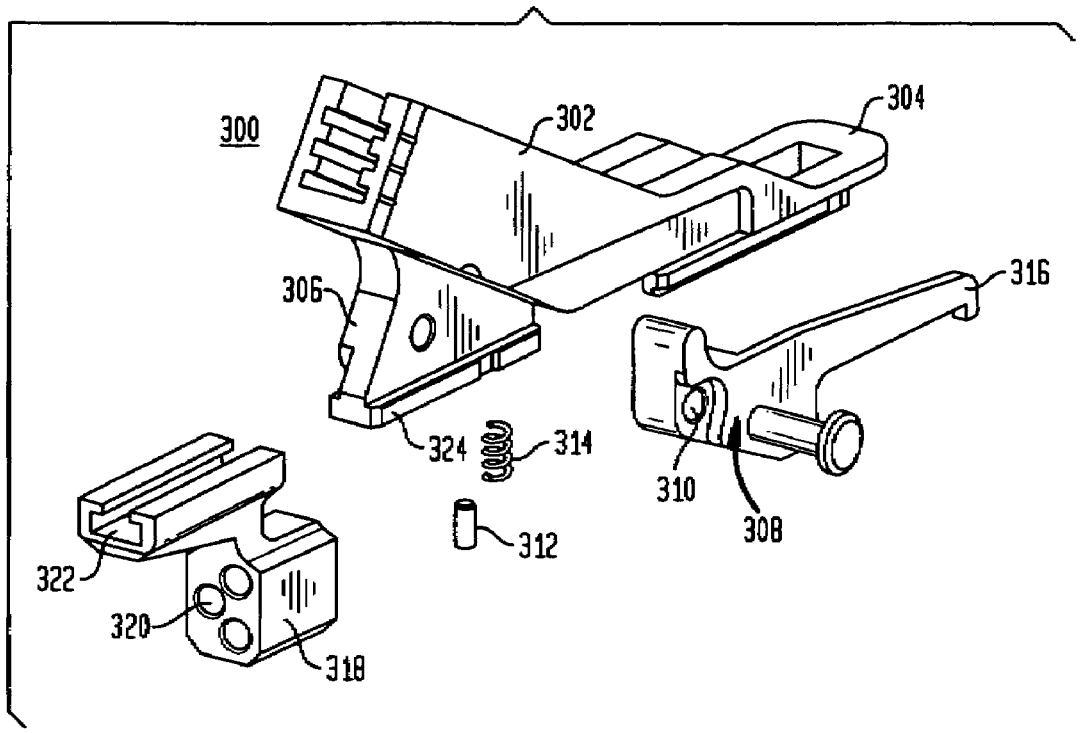
FIGS. 15A-15D show a punch tower for forming keel openings in tibial bone, in accordance with certain preferred embodiments of the present invention.
Figure 15D:
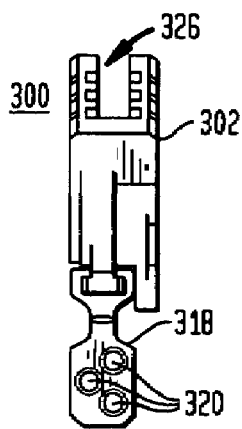

Referring to FIGS. 15A-15D, in accordance with certain preferred embodiments of the present invention, the system includes a punch tower 300 for forming keel openings in tibial bone. Referring to FIG. 15A, the punch tower 300 includes a main body 302 having a leading end 304 and a trailing end 306. The punch tower 300 includes a latch paw 308 securable to the main body 302. The latch paw includes an opening 310 extending therethrough that is adapted to receive a pivot pin 312 so that the latch paw may be coupled with the main body 302 and pivot relative thereto. The latch paw also includes a spring 314 that normally urges the latch paw to move downwardly at its hooked front end 316. The punch tower also preferably includes an alignment flange 318 that may be coupled with a trailing end 306 of the main body 302. The alignment flange includes one or more openings 320 extending therethrough that are adapted to receive pins for anchoring the punch tower to bone. The alignment flange 318 desirably includes a C-shaped opening 322 at an upper end thereof that is adapted to slide over a rail 324 at the trailing end 306 of the main body 302. A pin 312 is disposed in engagement with the alignment flange 318 to secure the alignment flange with the main body 302.

The main body 302 preferably includes a series of slots 326 extending therethrough. The series of slots 326 are adapted for forming different sized keel openings in tibial bone. Referring to FIG. 15A, a first slot 326A is used for forming a small keel opening, a second slot 326B is used for forming a medium keel opening and a third slot 326C used for forming a large keel opening. In other preferred embodiments, more than three slots may be provided.

Figure 15B:
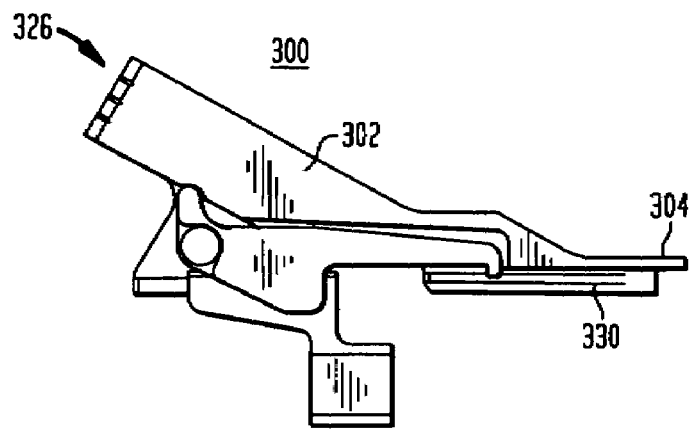
Figure 15C:
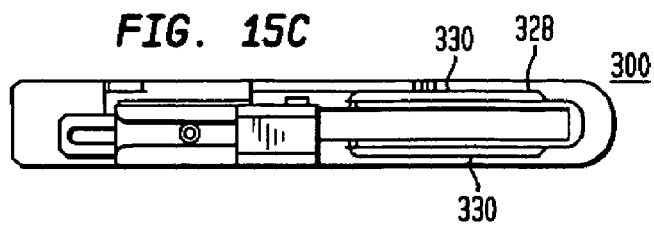

Referring to FIGS. 15B and 15C, an underside of the main body 302 includes an alignment guide 328 at the leading end 304 thereof. The alignment guide 328 includes male projections 330 extending along opposite sides of the main body.

Figure 16A:
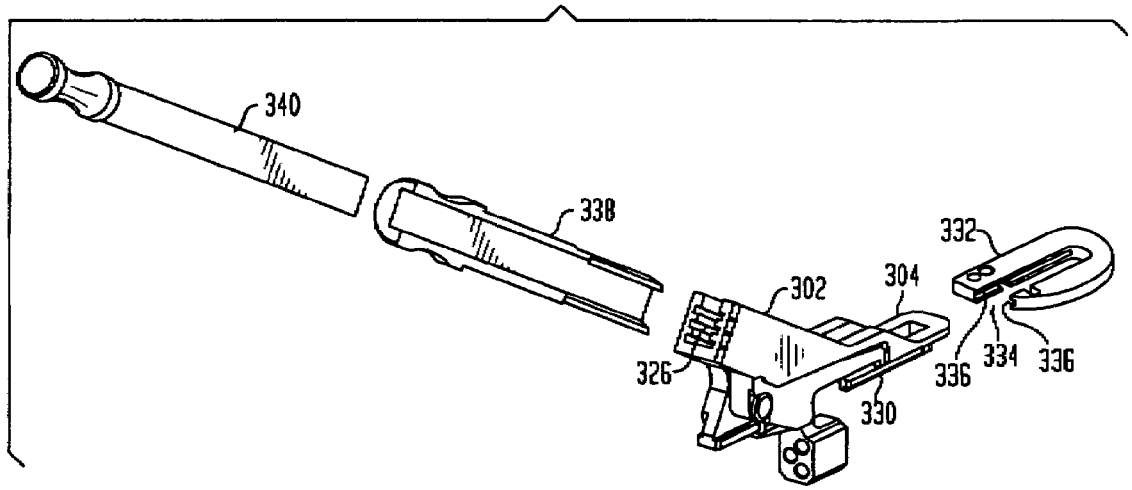
FIGS. 16A-16C show the punch tower shown in FIGS. 15A-15D.

Referring to FIG. 16A, the leading end 304 of the main body 302 is adapted to be coupled with a tibial template 332 having an elongated opening 334. The elongated opening 334 includes female grooves 336 extending along a longitudinal axis of the tibial template 332. The male projections 330 provided at the underside of the main body 332 are adapted to slide into the female grooves 336 in the tibial template 332.

Figure 16B:
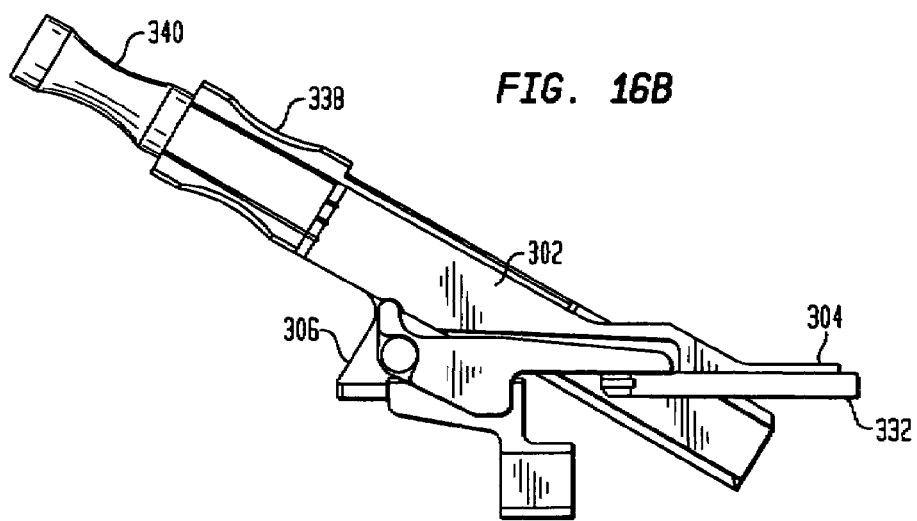
Figure 16C:
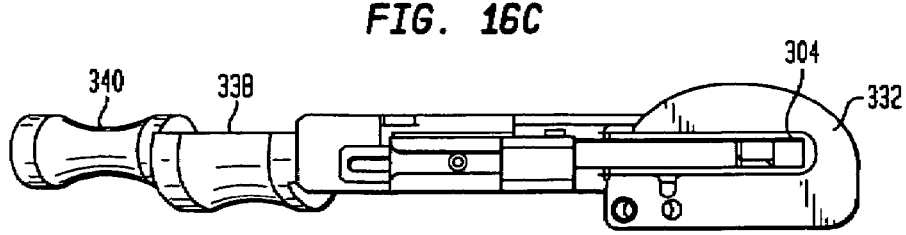

Referring to FIGS. 16A-16C, the assembly includes a chisel 338 that is insertible into one of the slots 326 in the punch tower. The assembly also includes a tamp 340 that slides within the chisel 338, as will be described in more detail below. FIGS. 16B and 16C show the leading end 304 of the punch tower coupled with the tibial template 332. As shown in FIG. 16B, the chisel 338 and tamp 340 are guided along an axis that intersects an axis extending between the leading 304 and trailing 306 ends of the main body 302.

As shown in FIGS. 16A and 16C, the design of the template 332 is universal so that the same template can be used as part of a knee implant procedure, such as a unicondylar procedure, to prepare any one of the four compartments on the two knees. These compartments include but are not limited to left lateral, left medial, right lateral and right medial. Although the present invention is not limited by any particular theory of operation, it is believed that using a universal template will reduce the number of parts required for preparing a knee for receiving an implant. This will reduce the cost and complexity of a procedure. In certain preferred embodiments, when the template 332 is in the position shown in FIG. 16A, it can be used for preparing the left lateral compartment or right medial compartment of the knee during a unicondylar procedure. In other preferred embodiments, when the template is in the position shown in FIG. 16C, it can be used for preparing the left medial compartment or right lateral compartment of the knee during a unicondylar procedure. Thus, the template is designed to be flipped over so that it can be used for preparing different compartments of the knee (at the proximal end of the tibia) during a knee implant procedure such as a unicondylar procedure. The ability to use the same part for preparing different compartment of the knee will minimize the number of parts needed and reduce costs.

Referring to FIGS. 17A-17D, the chisel 338 preferable includes a leading end 342 and a trailing end 344. The leading end preferably includes a sharpened surface 346 that cuts into bone. The trailing end 344 desirably includes a striking surface 348 so that the chisel 338 may be hit with a hammer or mallet. The second end 344 includes a handle 350 having a shoulder 352 that limits advancement of the chisel 338 into the slot of the punch tower. The exact positioning of the shoulder 352 may be varied in response to the depth of the bone cut required to be formed in the tibial bone.

Referring to FIGS. 17C-17D, the chisel includes a C-shaped opening 354 extending along the length thereof. The C-shaped opening provides a space for bone to move when the keel opening is being formed. The C-shaped opening 354 also provides a space for a tamp, as will be described in more detail below.

Referring to FIGS. 18A-18D, in accordance with certain preferred embodiments of the present invention, the system includes a tamp 340 having a leading end 356 and a trailing end 358 including a handle 360. Referring to FIG. 18C, the handle 360 includes a shoulder 362 that preferably abuts against the striking surface 348 of the chisel 338 (FIG. 17A) for limiting advancement of the tamp 340. After the chisel has been advanced into bone for forming an outline of the keel opening, the tamp is advanced through the chisel to impact the bone and complete the formation of the keel opening.

Figure 19:
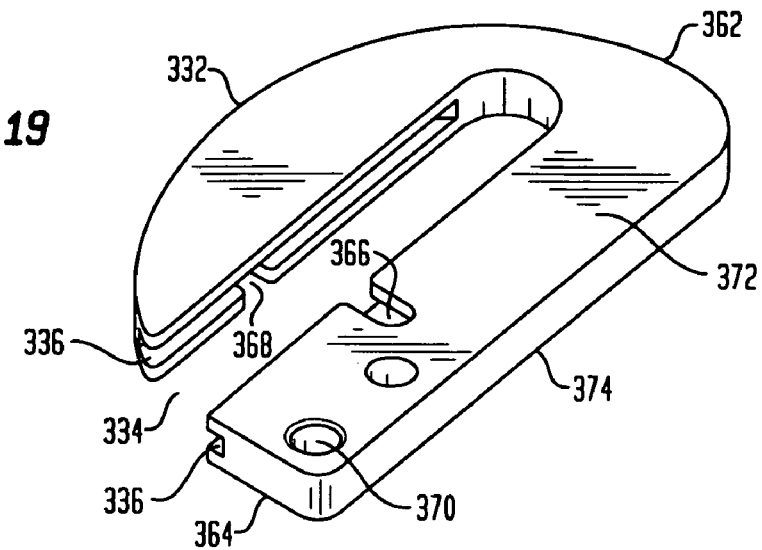
FIG. 19 shows a tibial template, in accordance with certain preferred embodiments in the present invention.
Figure 21A:
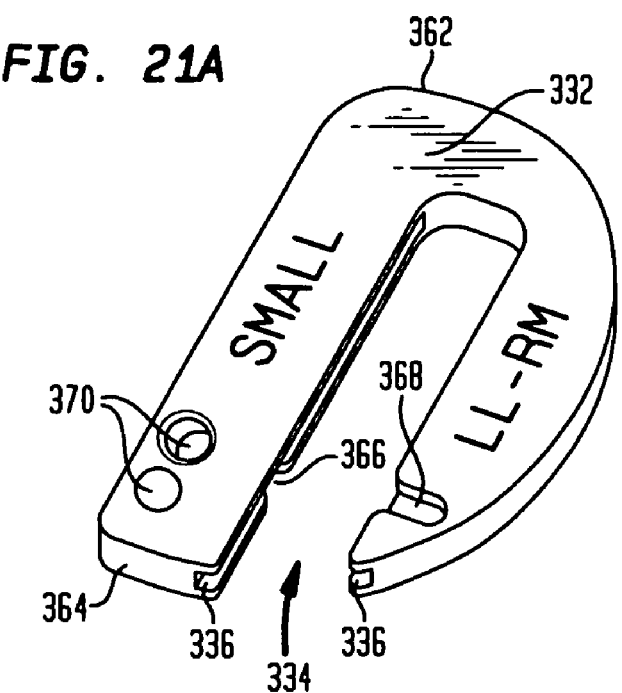
FIGS. 21A-21E show the tibial template of FIG. 19.
Figure 21B:
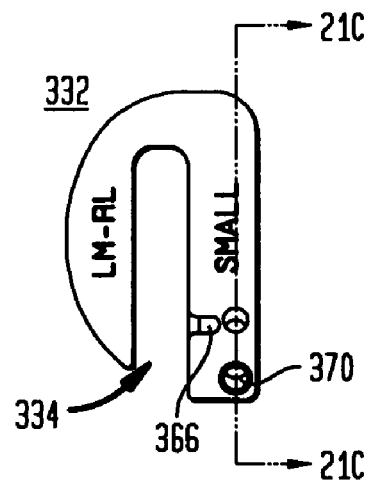
Figure 21C:
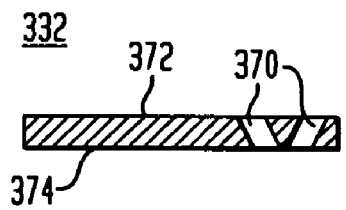
Figure 21D:
Figure 21E:
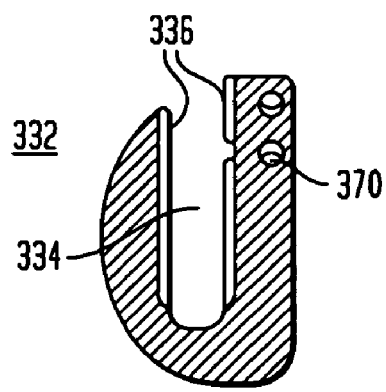
Figure 22A:
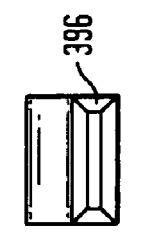
FIGS. 22A-22D show a spacer for evaluating flexion and extension gaps, in accordance with certain preferred embodiments of the present invention.
Figure 22B:
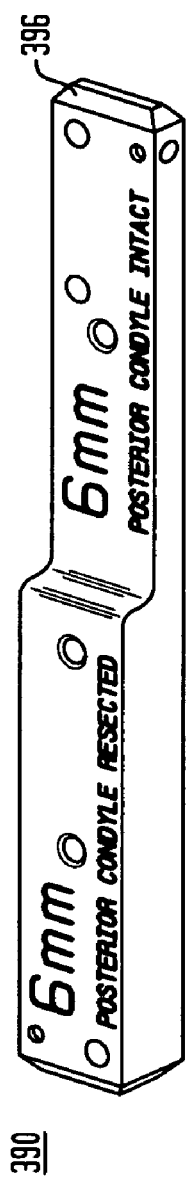
Figure 22C:
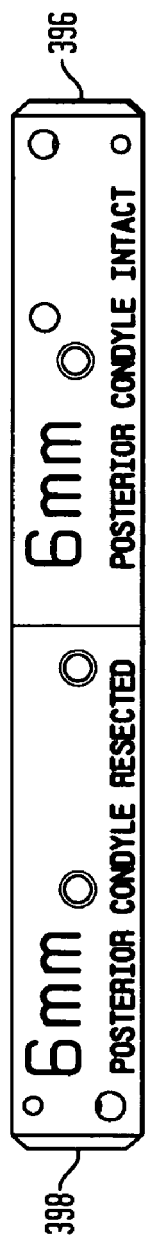
Figure 22D:
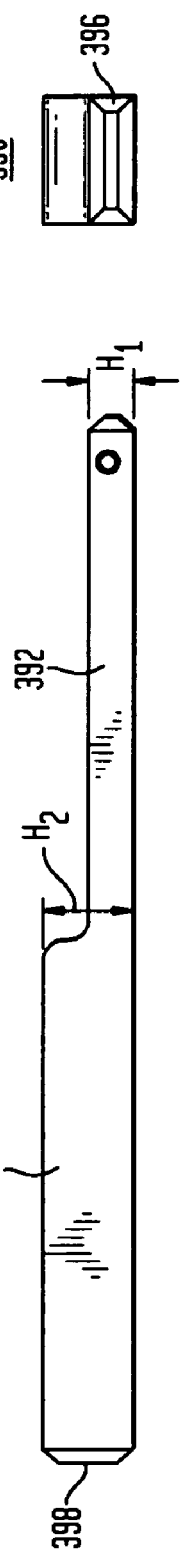

Referring to FIGS. 19 and 21A, the tibial template 332 preferably includes a central opening 334 having opposing female slots 336 extending between a leading end 362 and a trailing end 364 thereof. The tibial template includes a first slot 366 for receiving a hooked end of a latch paw when the template is used on one side of a knee and a second slot 368 that is also designed to receive the hooked end of a latch paw when the template is flipped over. The tibial template 332 also desirably includes one or more openings 370 extending between top and bottom surfaces 372, 374 thereof, which are adapted to receive anchor pins for anchoring the tibial template to the proximal end of the tibia.

Figure 20:
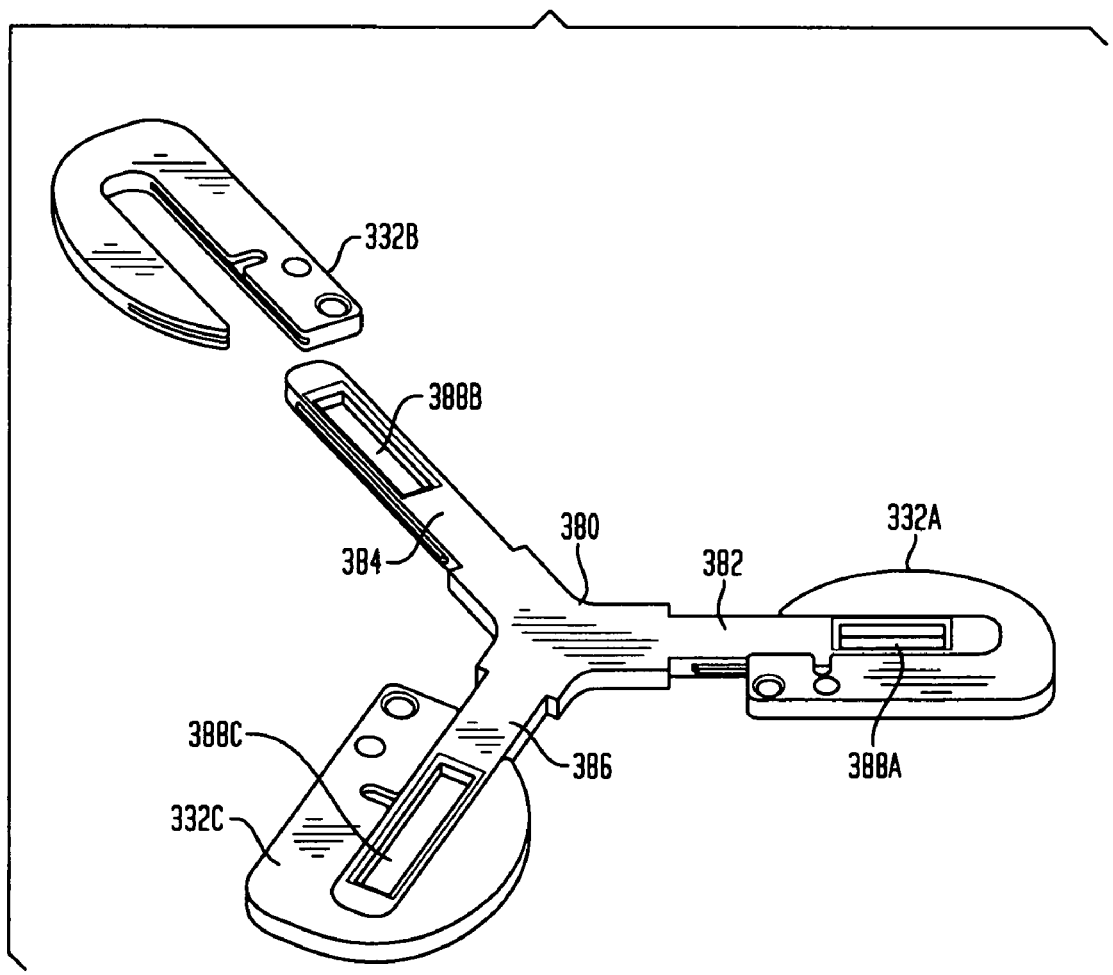
FIG. 20 shows a holder for tibial templates having different sizes, in accordance with certain preferred embodiments of the present invention.

FIG. 20 shows a holder 380 for holding different sized tibial templates. The holder preferably includes a first arm 382 for holding an extra small or small sized tibial template 332A, a second arm 384 for holding a medium or large sized tibial template 332B and a third arm 386 for holding an extra large sized tibial template 332C. Each arm of the holder 380 has an outer end including an opening 388 that is the size of a keel opening for the particular implant part to be implanted into bone. Thus, the opening 388A in the first arm 382 is smaller than the opening 388B in the second arm 384 and so on.

FIGS. 22A-22D show a spacer bar 390, in accordance with certain preferred embodiments of the present invention. The spacer bar 390 includes a first section 392 defining a height $H_1$ and a second section 394 defining a height $H_2$ that is greater than $H_1$. In certain preferred embodiments, the difference between $H_1$ and $H_2$ is preferably the thickness of the implant that is positioned between the posterior condyle and the tibia. The spacer bar includes a first end 396 that is tapered and a second end 398 that is also tapered. As will be described in more detail below, the spacer bar is placed between the distal end of a femur and a proximal end of a tibia to determine spacing between the femur and tibia during extension and flexion of the knee joint. The spacer bar may be used to align a cutting instrument for cutting the posterior region of the femur. As described herein, it is preferable that the gap between the femur and the tibia is the same for both flexion and extension. Thus, the present invention seeks to prepare bone sites and attached implant components to the respective bone sites so that the gap between the femur and tibia is the same in both flexion and extension so as to reduce joint instability and provide for smooth movement between flexion and extension.

Figure 23:
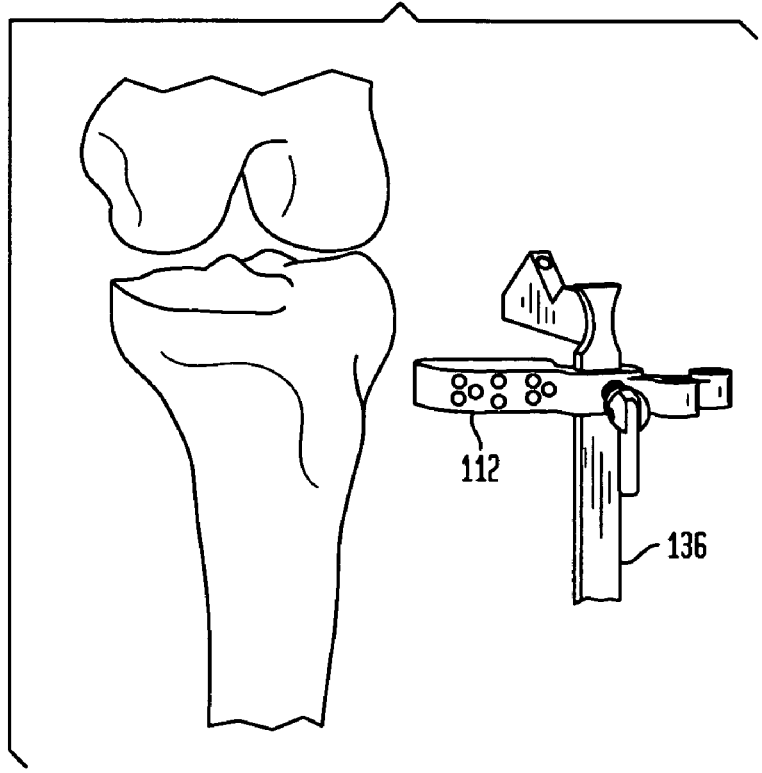
FIGS. 23-32 show a method of resecting a proximal end of a tibia, in accordance with certain preferred embodiments of the present invention.
Figure 24:
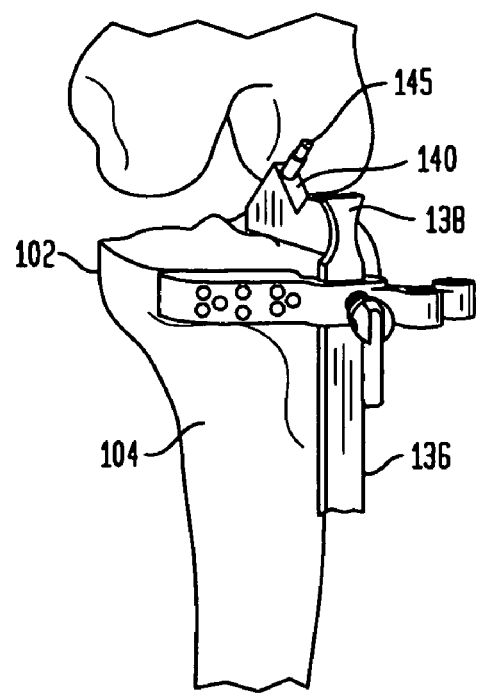

FIGS. 23-32 show a preferred method of preparing a seating surface at a proximal end of a tibia. Referring to FIG. 23, a tibial resection block 112 is coupled with an elongated rod 136. Referring to FIG. 24, the attachment flange 140 at the proximal end 138 of the rod 136 is secured to the proximal end 102 of the tibia 104 using a fastener 145 such as a pin. A lower end (not shown) of the rod 136 is preferably secured to the tibia 104 such as by using an ankle clamp.

Figure 25:
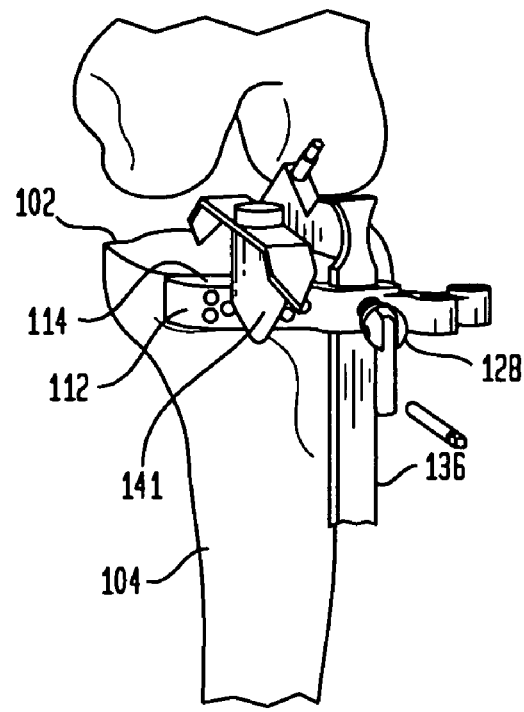

Referring to FIG. 25, the tibial resection block 112 has a top surface 114 that defines a cutting plane for the proximal end 102 of the tibia 104. A stylus 141 is preferably coupled with the tibial resection block so as to determine a depth of cut into the proximal end 102 of the tibia 104. The tibial resection block 112 may slide along the rod 136 until the desired position of the top surface 114 of the block 112 is determined. At that point, the tightening screw 128 is tightened for securing the position of the tibial resection block 112 along the rod 136. In other preferred embodiments, the tibial resection block may be coupled with a navigation tracker for aligning the top surface 114 of the block 112 at the appropriate depth for the resection.

Figure 26:
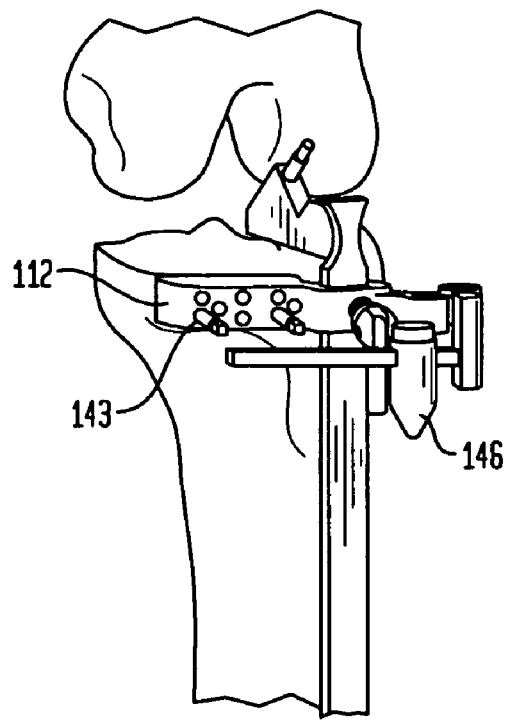

Referring to FIG. 26, anchoring pins 143 may be passed through openings in the tibial resection block 112 to further stabilize the tibia resection block relative to the tibia. Referring to FIG. 26, a sagittal resection guide 146 may be moved into abutment against the tibial resection block 112.

Figure 27:
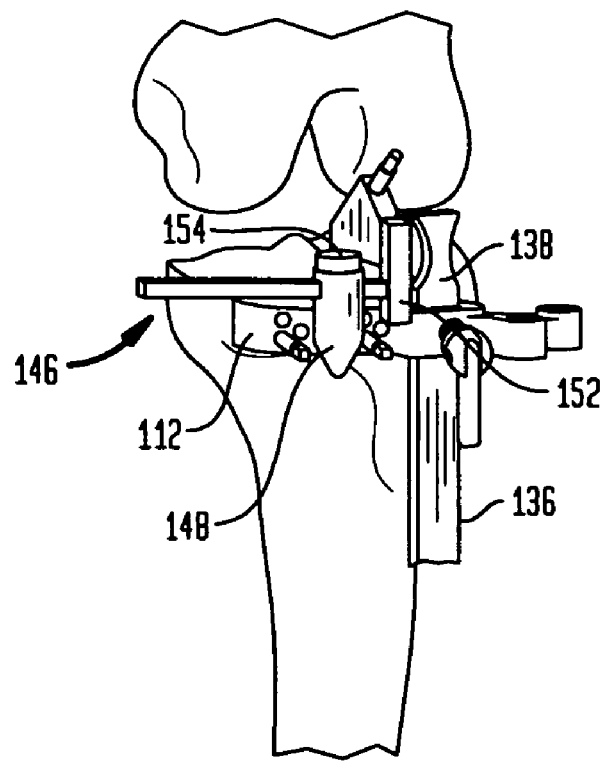

Referring to FIG. 27, the sagittal resection guide 146 has a main body 148 that is abutted against the tibial resection block 112. The depressible button 154 of the sagittal resection guide 146 may be depressed to allow movement of the alignment block 152 for defining a sagittal cutting plane between the alignment block 152 and the proximal end 138 of the rod 136. The outer surface of the alignment block 152 may be rounded to provide for a perpendicular cut of the bone.

Figure 28:
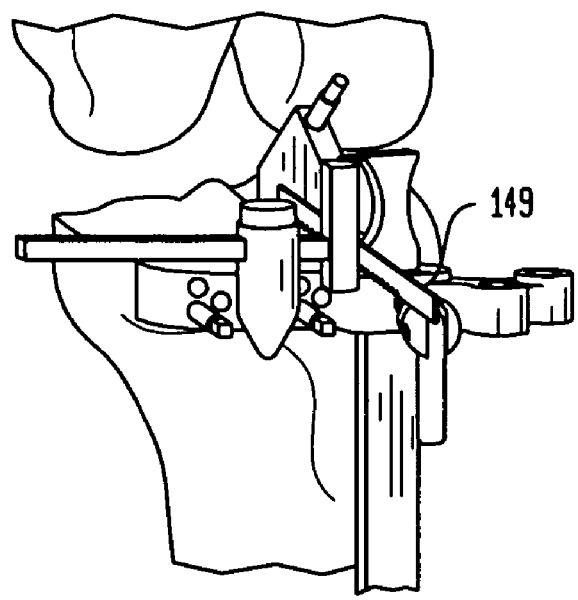
Figure 29:
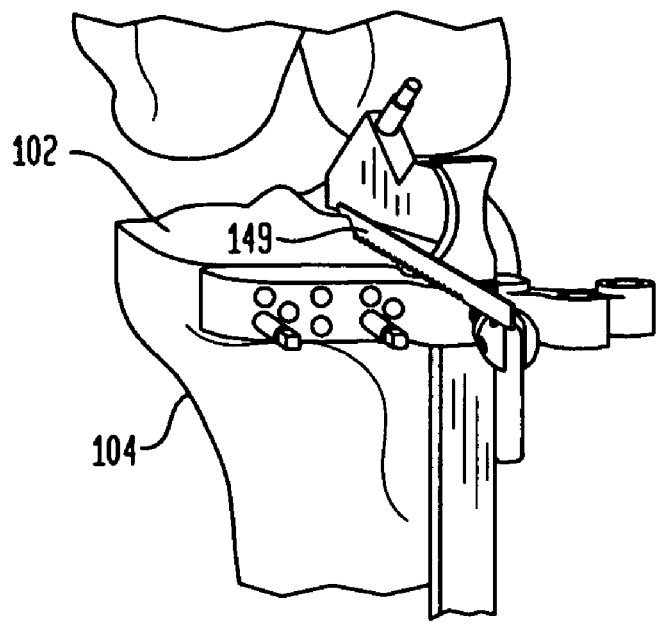
Figure 30:
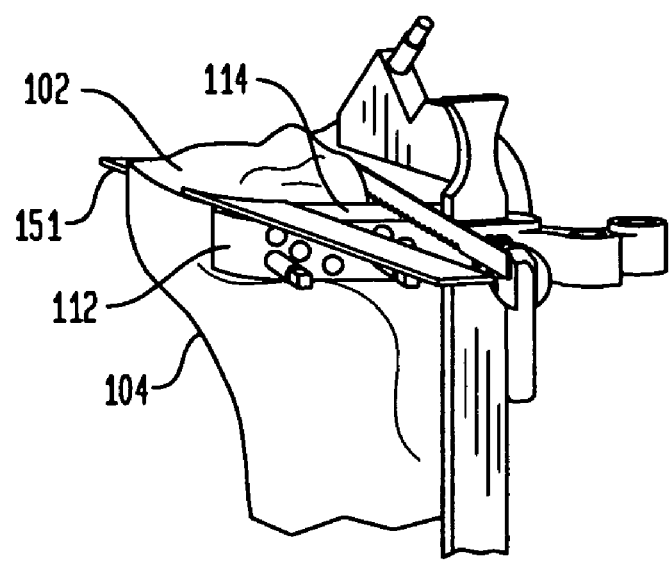
Figure 31:
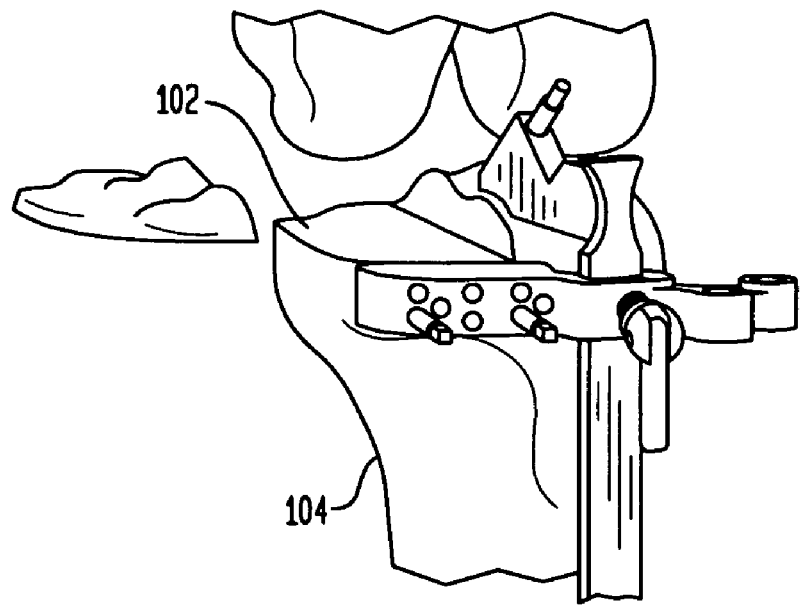
Figure 32:
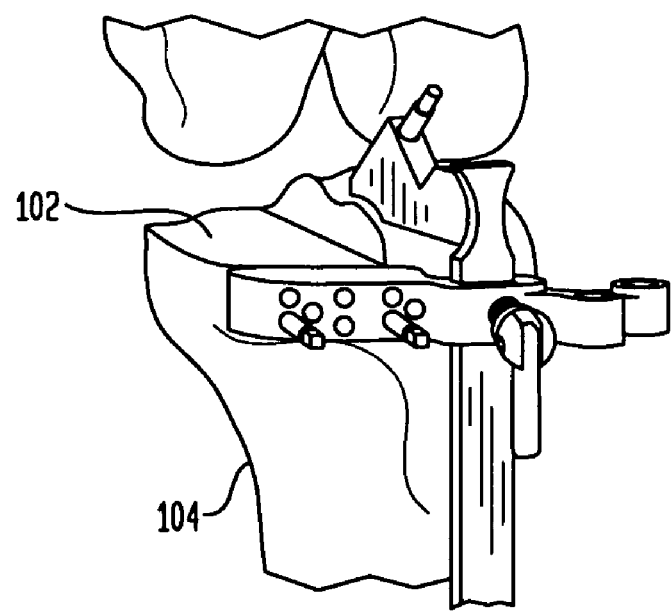
Figure 33:
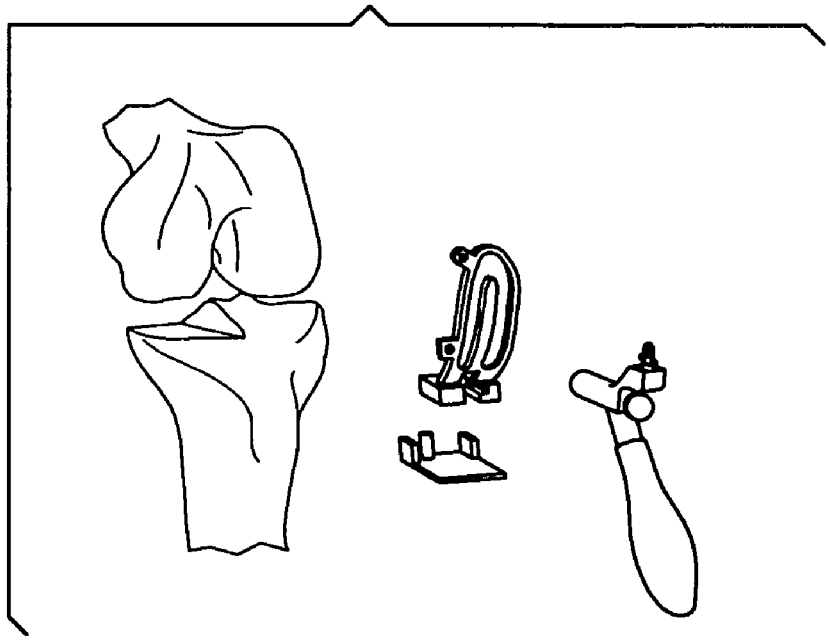
FIGS. 33-37 show a method of aligning the combination bur template and spacer block of FIGS. 6A-6H in a knee joint, in accordance with certain preferred embodiments of the present invention.

Referring to FIGS. 28 and 29, a saw 149 or other cutting instrument may be used to make a sagittal resection of the proximal end 102 of the tibia 104. Referring to FIG. 30, a second cutting instrument or saw 151 may be used to cut the proximal end 102 of the tibia 104 in a plane defined by the top surface 114 of the tibial resection block 112. FIGS. 31 and 32 show the proximal end 102 of the tibia 104 after the tibial resection if complete. The tibial resection block may then be disengaged from the tibia.

Figure 5A:
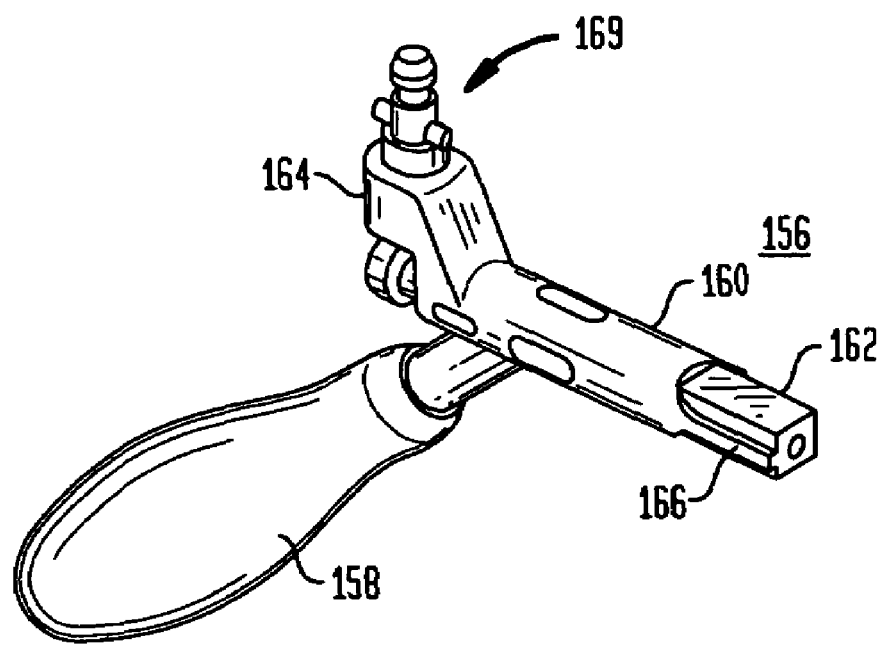
FIGS. 5A-5E show a modular handle, in accordance with certain preferred embodiments of the present invention.
Figure 5B:
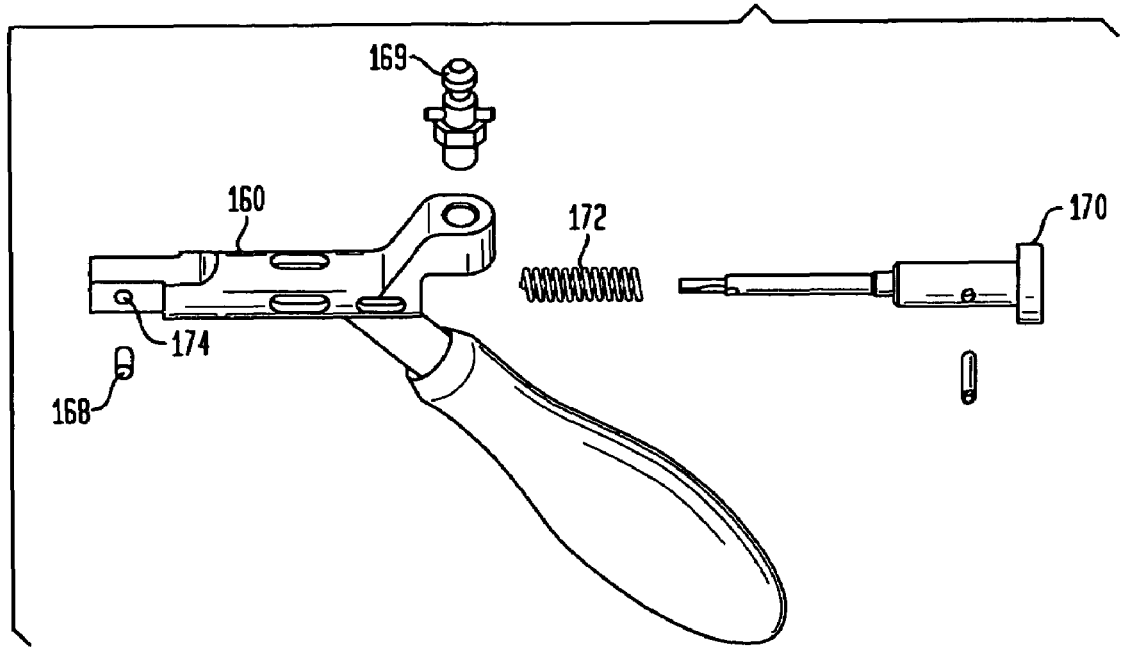
Figure 5D:
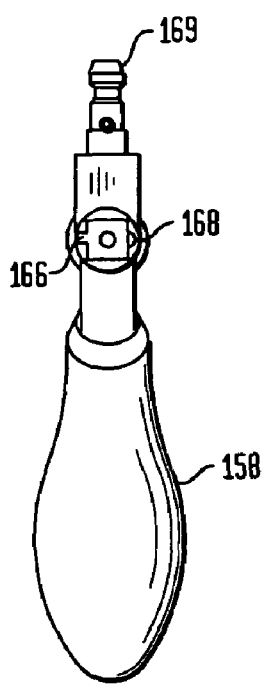
Figure 5C:
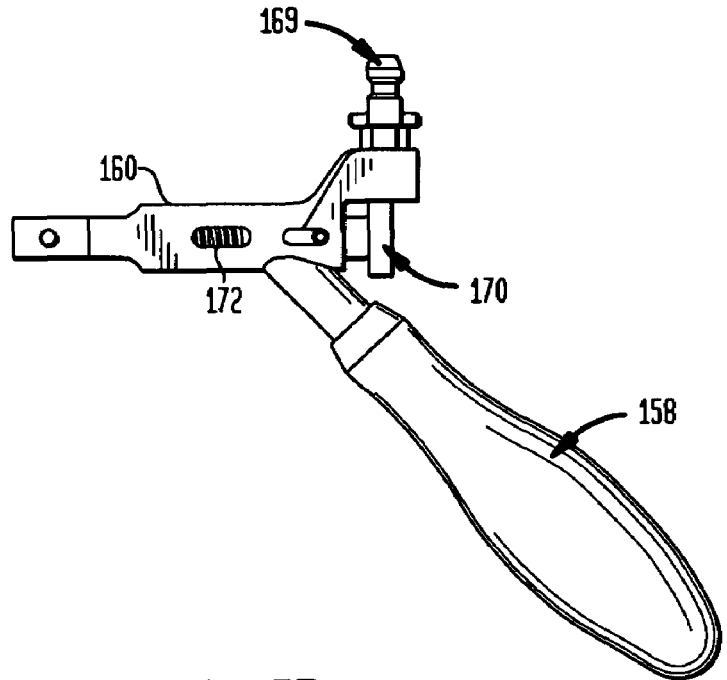
Figure 5E:
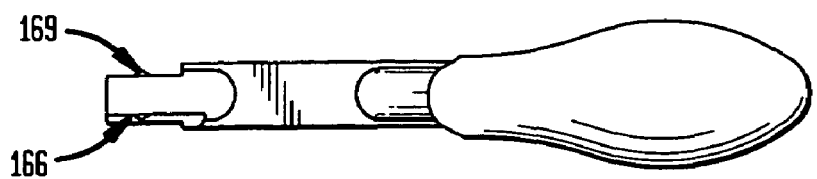

FIGS. 33-37 show femoral alignment of the bur template/spacer block within the knee joint. The leading end 162 of the modular handle 158 shown in FIGS. 5A and 6G is coupled with the female opening 198 of the bur template/spacer block. The male projection 166 at the leading end 162 of the modular handle 158 is preferably inserted into the elongated alignment groove 200 in the opening 198 at the trailing end of the spacer block portion 176. A shim may be coupled with the spacer block for adjusting for the gap distance in the knee.

Figure 34:
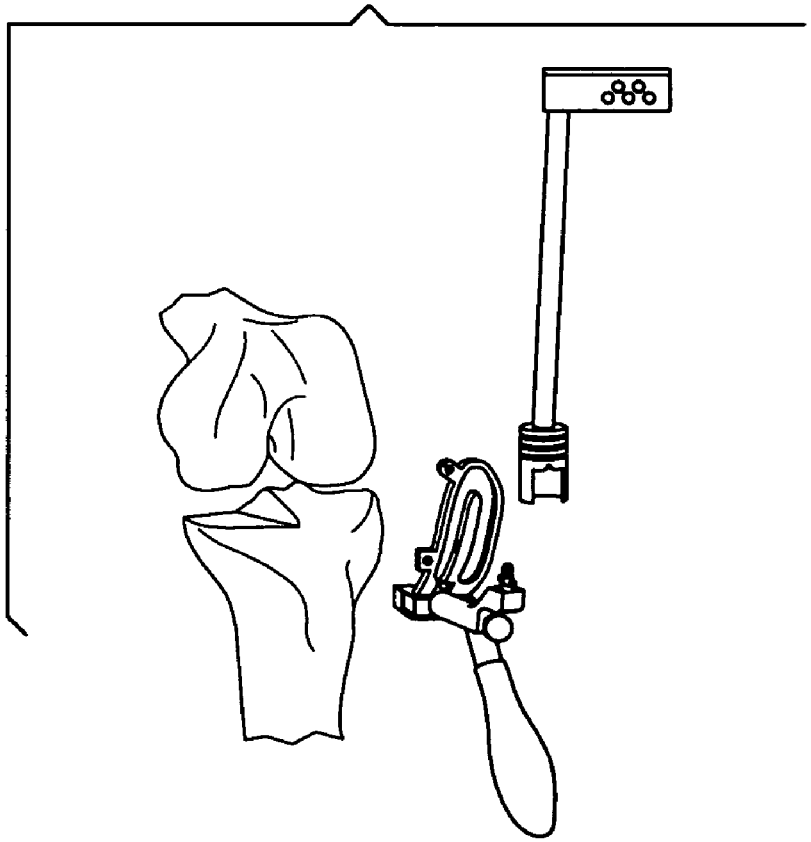
Figure 35:
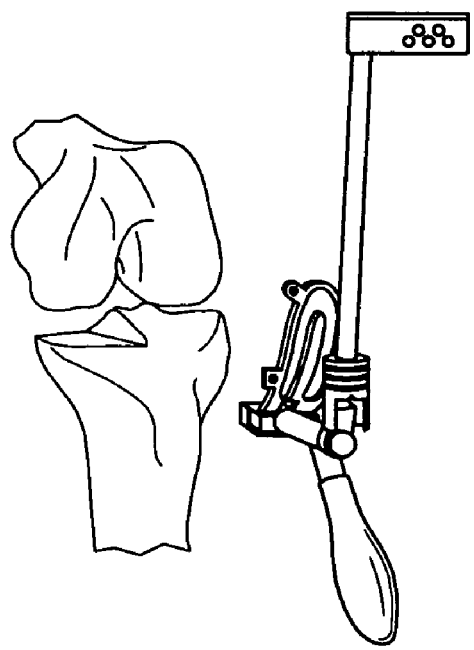
Figure 36:
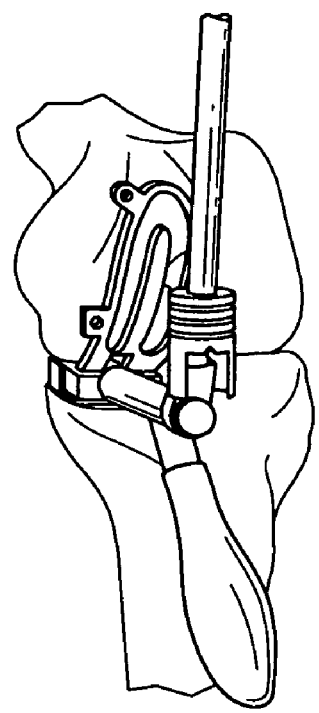
Figure 37:
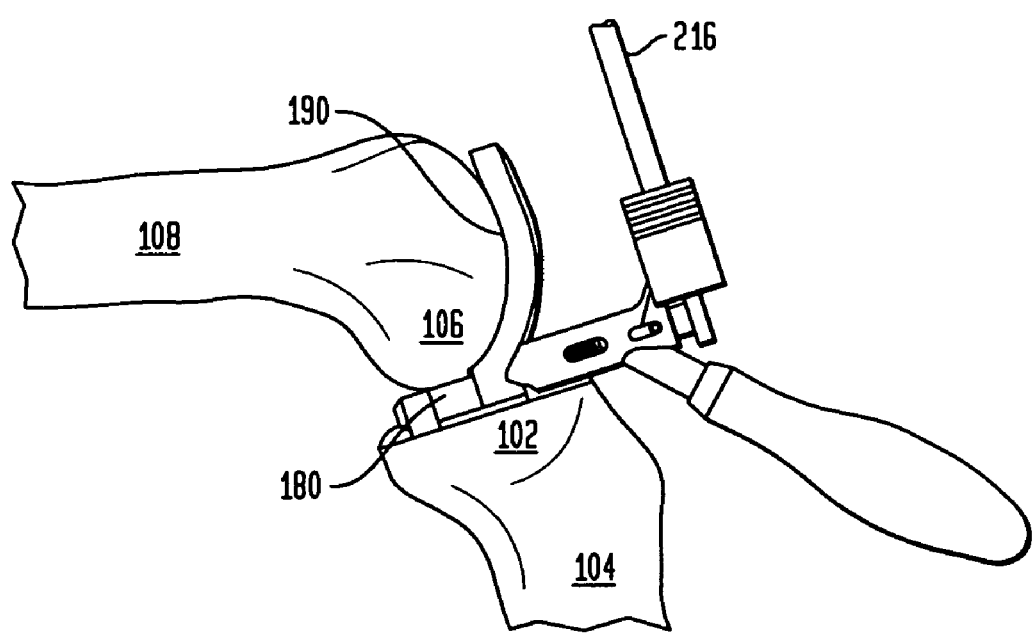

Referring to FIG. 34, the alignment tower 216 shown in FIG. 8A is coupled with the male projection 169 of the modular handle 158 (FIG. 5A). The male projection 169 of the modular handle is preferably coupled with the well 232 at the bottom of the alignment post 216. Referring to FIGS. 35-37, the spacer block portion 180 of the bur template/spacer block is inserted into the joint between the distal end 106 of femur 108 and the proximal end 102 of tibia 104. An alignment rod is desirably placed in the appropriate hole in the alignment tower 216 which is preferably centered on the knee or on the femur using openings 228 in the alignment flag 224 (FIG. 8A). Referring to FIG. 37, once the spacer block 180 is in place, the tibia is extended until the curved inner surface 190 of the bur template engages the femoral condyle. Once the entire length of the curved inner surface of the bur template engages the femoral condyle, extension of the knee joint may be stopped. At that stage, the bur template is preferably secured from further movement relative to the femur using fasteners such as anchoring pins.

Figure 38:
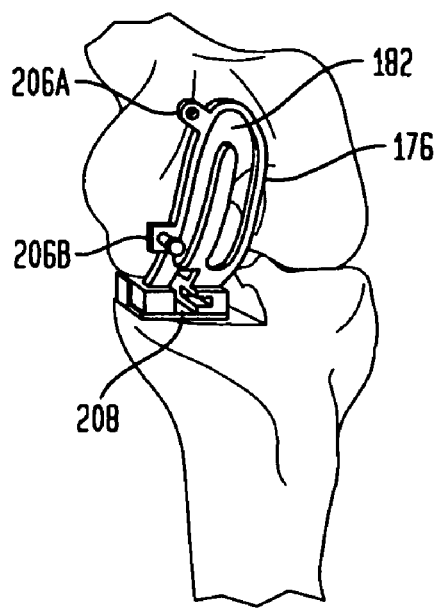
FIG. 38 shows the bur template/spacer block of FIGS. 6A-6H secured between a tibia and a femur, in accordance with certain preferred embodiments of the present invention.

Referring to FIG. 38, the one or more pins for anchoring the bur template from further movement relative to the femur may be inserted through securing flanges 206A, 206B. In the particular preferred embodiment shown in FIG. 38, a shim 208 is coupled with an underside of the spacer block for adjusting the tension of the bur template/space block in the joint. As will be described in more detail herein, the shim may be used for balancing the gap between the femur and the tibia when the knee joint moves between flexion and extension. A bur (not shown) may be inserted into the slot 182 of the bur template/spacer block to prepare the condyle at the distal end of the femur for receiving a femoral component of the implant.

Figure 39:
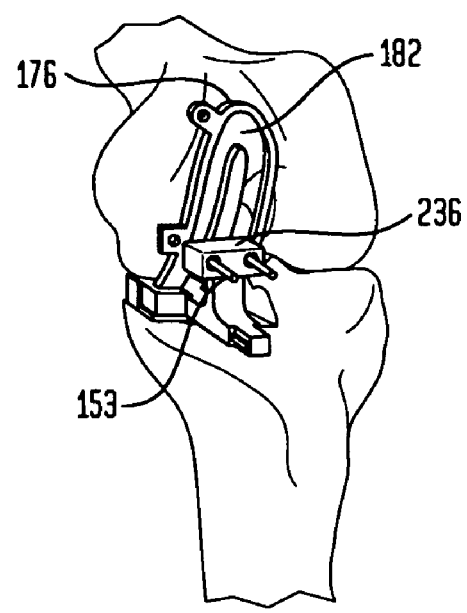
FIGS. 39-43 show a method of resecting a posterior region of a femoral condyle, in accordance with certain preferred embodiments of the present invention.
Figure 40:
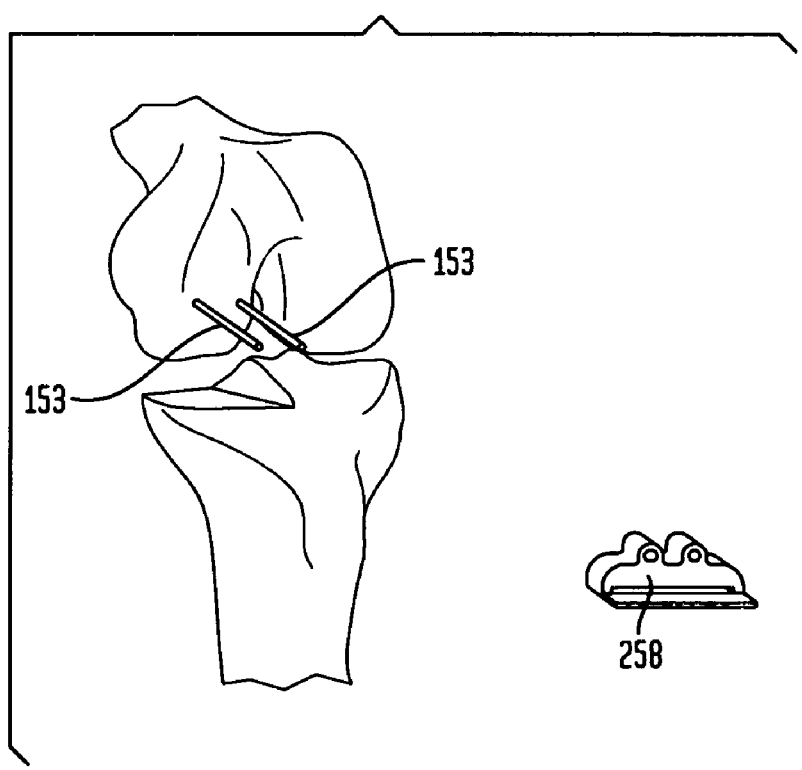

Referring to FIGS. 9A and 39, the alignment rail 238 of the posterior resection guide locator 236 is preferably inserted into the opening at the trailing end of the bur template/spacer guide 176. The projection 248 on the alignment rail 238 is preferably inserted into the elongated, alignment groove 200 (FIG. 6G) in the spacer block. Referring to FIG. 39, once the alignment rail is inserted into the opening in the spacer block, the pin openings 256 of the posterior resection guide locator 236 are preferably in alignment with the slot 182 of the bur template/spacer block 176. Referring to FIGS. 39 and 40, a pair of alignment pins 153 are desirably inserted through the pin openings in the posterior resection guide locator 236 and advanced into the bone at the distal end of the femur. In certain preferred embodiments of the present invention, the guide locator 236 is preferably sized and shaped so that the alignment pins 153 are attached to the femur at a location that will eventually result in 6 mm of bone being resected from the posterior region of the femur.

Figure 41:
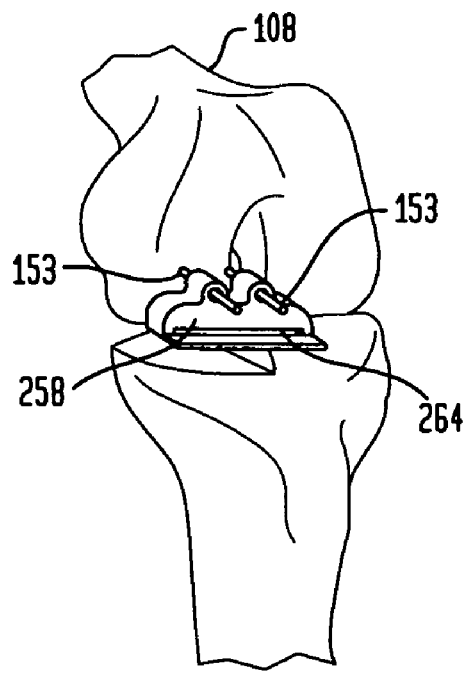
Figure 42:
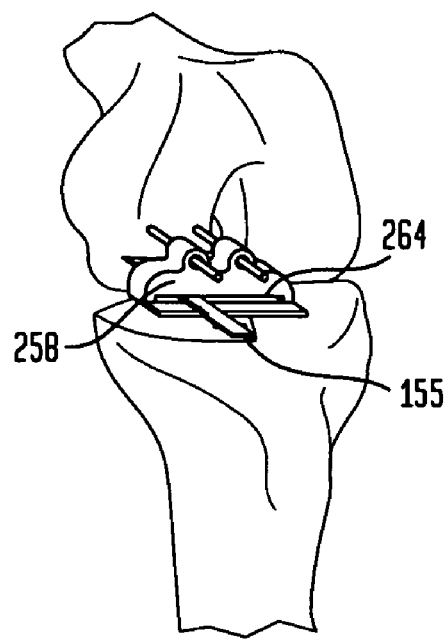
Figure 43:
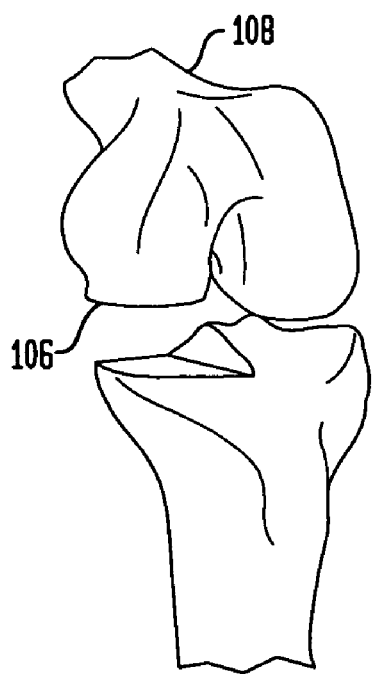

Referring FIGS. 40 and 41, a posterior resection guide 258 is aligned with the femur 108 using the previously anchored alignment pins 153. Referring to FIGS. 41 and 42, a posterior resection of the femur is desirably performed by passing a cutting instrument such as a saw 155 through the slot 264 in the posterior resection guide 258. The posterior resection guide is sized and shaped so that it slides over the alignment pins that were previously anchored in the bone using the posterior resection guide locator. The posterior resection guide is preferably sized and shaped so that once it is slid over the alignment pins 153, the slot is located so that a predetermined section of bone from the posterior region of the femur is removed. In certain preferred embodiments, the posterior resection guide is sized and shaped so that 6 mm of bone is removed from the posterior region of the femur. As shown in FIG. 43, after the posterior resection of the femur 108 is complete, the posterior resection guide and the alignment pins are removed.

Figure 44:
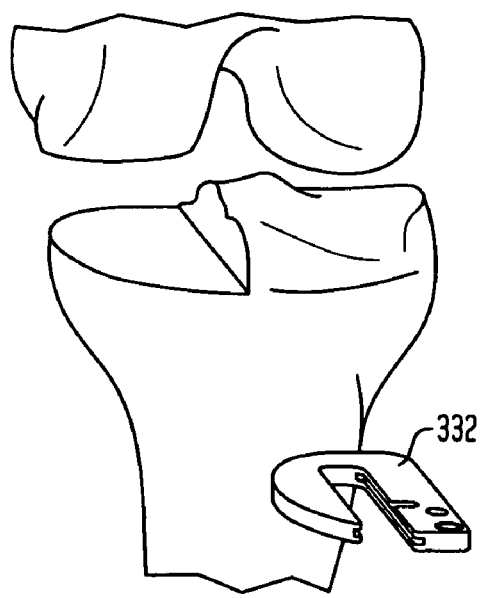
FIGS. 44-56 show a method of forming a keel opening at the proximal end of a tibia, in accordance with certain preferred embodiments of the present invention.
Figure 45:
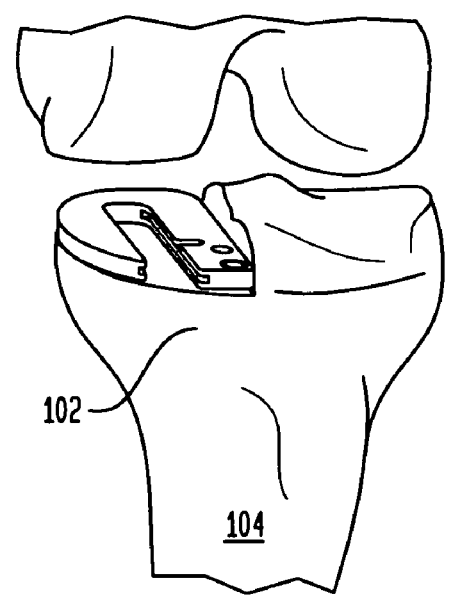

Referring to FIGS. 44 and 45, a tibial template 332 may be positioned over the prepared site at the proximal end 102 of the tibia 104. The surgeon desirably makes a determination of the proper sized tibial template that should be used, which is based upon the area of the prepared site at the proximal end of the tibia. The tibial template is preferably used to prepare the site for receiving a tibial component of an implant.

Figure 46:
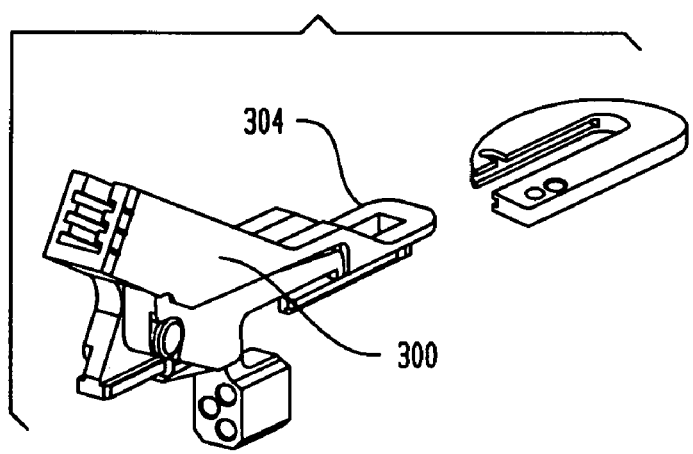
Figure 47:
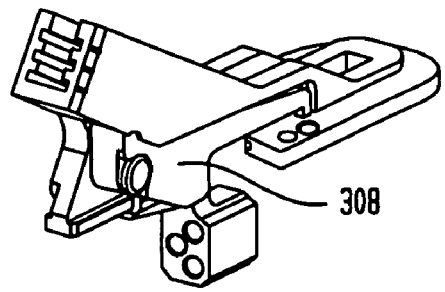

Referring to FIGS. 46 and 47, after the proper tibial template has been selected, the leading end 304 of the punch tower 300 is coupled with the opening in the tibial template. As described above, the male projections at the leading end 304 of the punch tower 300 slide into the female openings in the elongated opening of the tibial template. The latch paw 308 desirably engages a latch paw groove formed in the top surface of the tibial template for securing the tibial template and the punch tower together.

Figure 48:
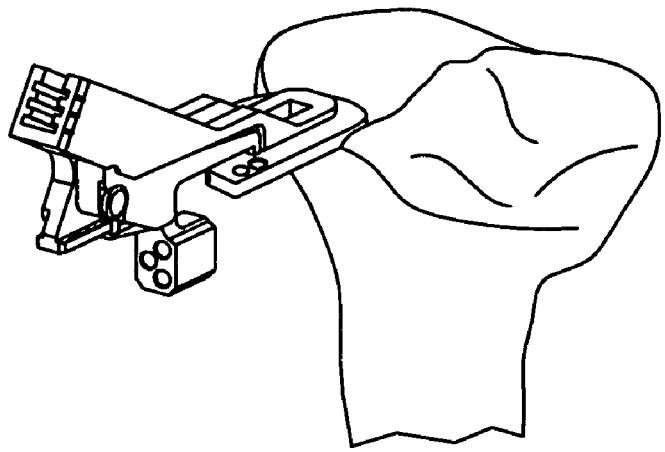
Figure 49:
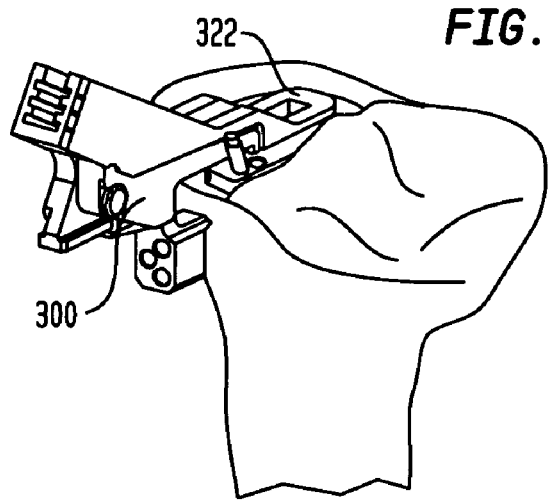

Referring to FIGS. 48 and 49, the coupled together tibial template and punch tower are preferably moved into place over the prepared site at the proximal end of the tibia. Referring to FIG. 49, a pin may be used to anchor the tibial template and/or the punch tower to the bone.

Figure 50:
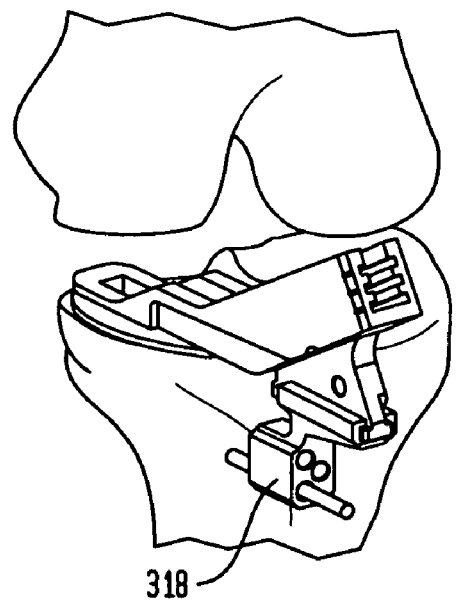

Referring to FIG. 50, addition pins may be passed through the attachment flange 318 of the punch tower to further anchor the punch tower to bone.

Figure 51:
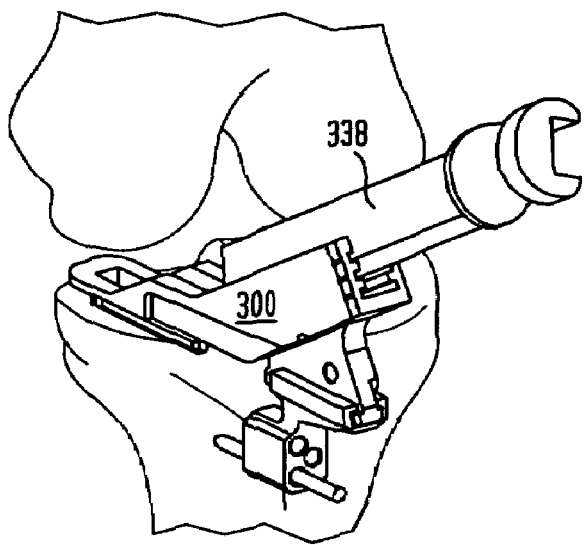
Figure 52:
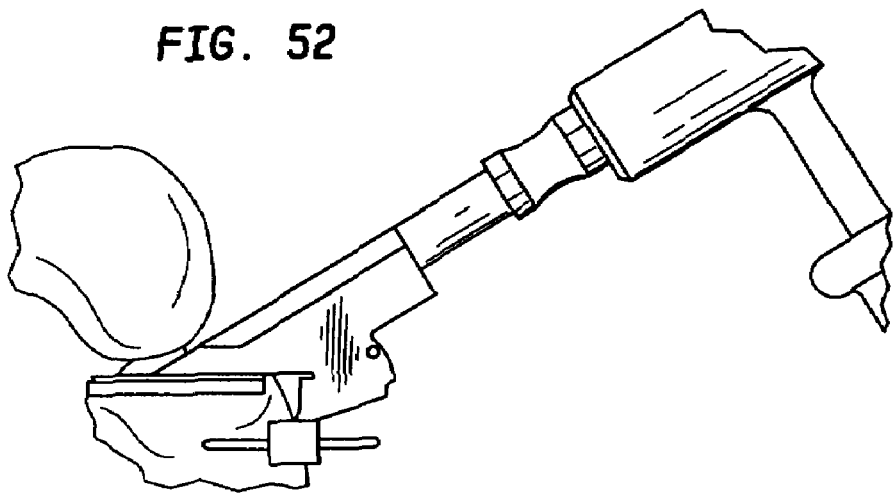
Figure 53:
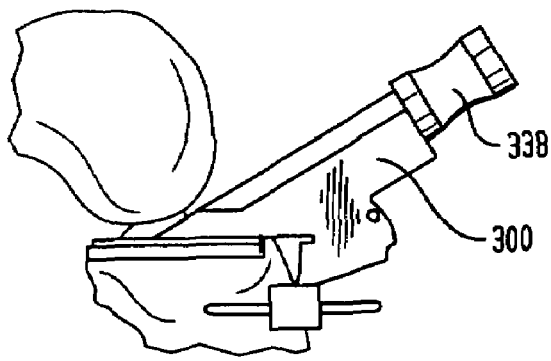

Referring to FIGS. 51-53, after the punch tower and tibial template have been anchored to the tibia, the chisel 338 is desirably passed through an appropriate slot in the punch tower and hammered in place using a hammer or mallet. As shown in FIG. 51, the punch tower 300 has at least three slots for receiving the chisel 338. As noted above, each of the three slots will result in the formation of keel openings having a particular size. FIG. 53 shows the chisel 338 after it has been fully advanced in the punch tower 300.

Figure 54:
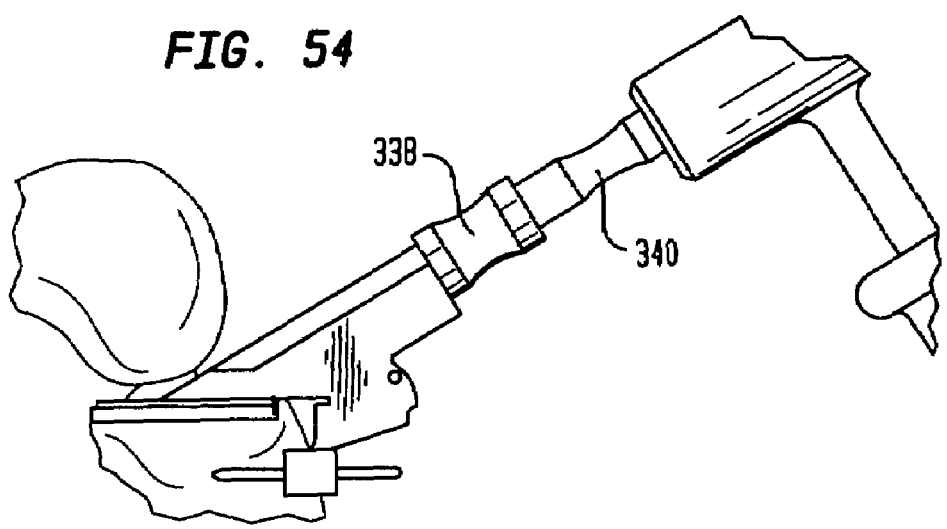
Figure 55:
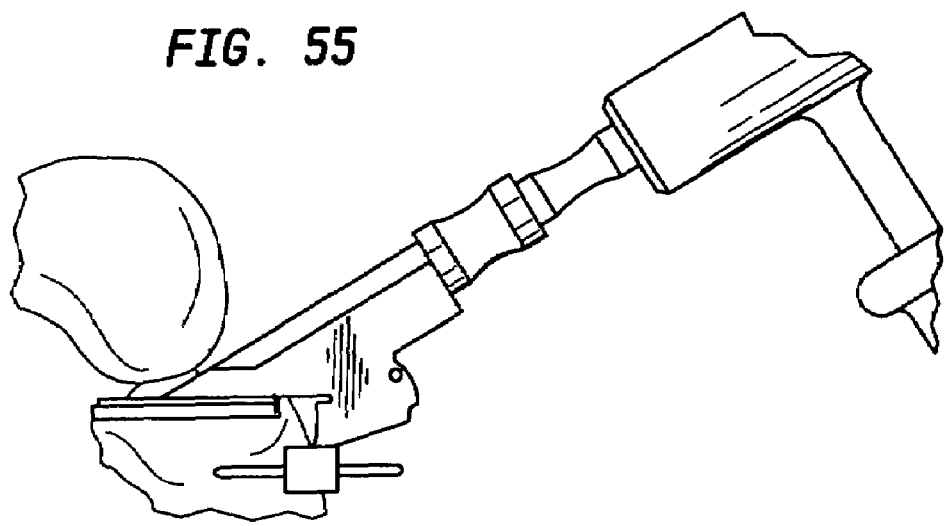
Figure 56:
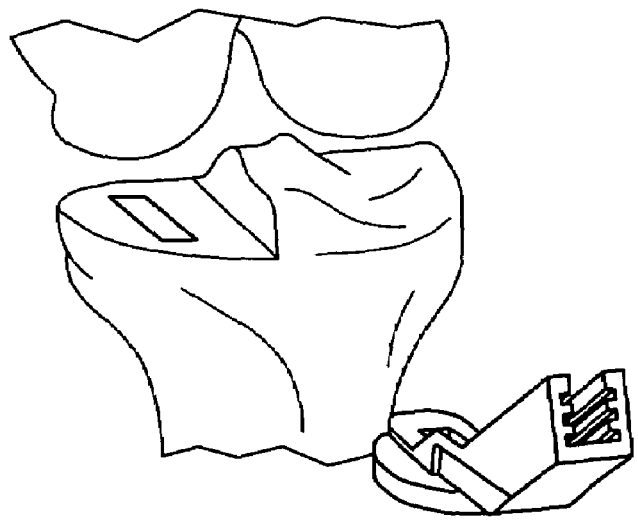

Referring to FIGS. 54 and 55, the tamp 340 is then hammered in place through the chisel 338 to complete formation of the keel opening. Referring to FIG. 56, the punch tower is then removed. A keel opening has been formed at the prepared site at the proximal end of the tibia.

Figure 57:
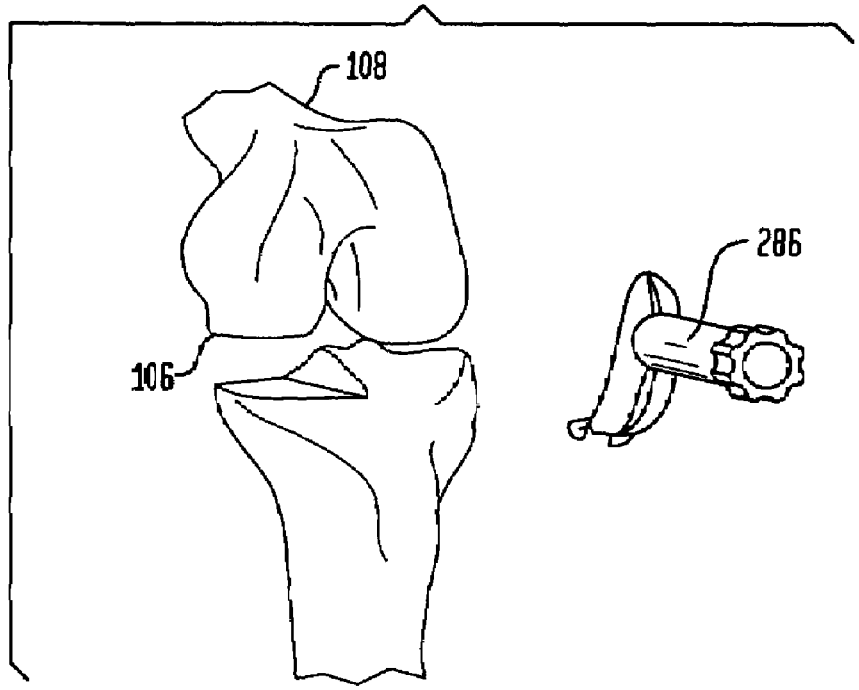
FIGS. 57-59 show a method of making openings for a post and a fin of a femoral component, in accordance with certain preferred embodiments of the present invention.
Figure 58:
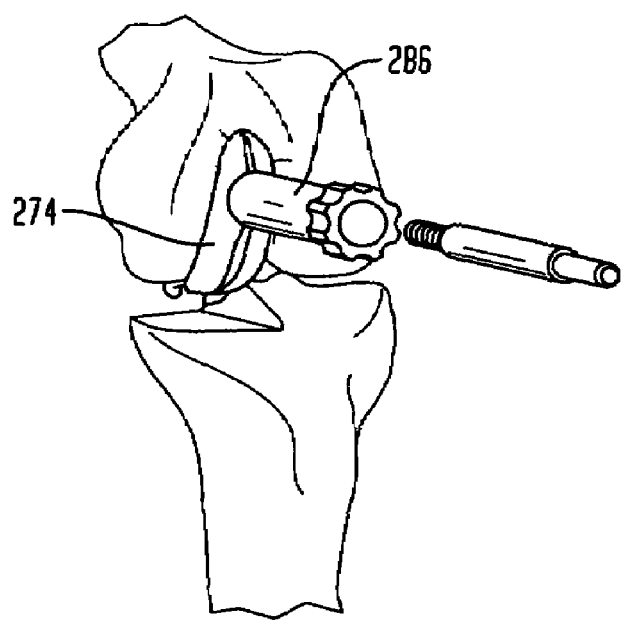

FIG. 57 shows a prepared site at the distal end 106 of the femur 108, which has been prepared by passing a bur through the slot in the bur template/spacer block shown and described above in FIGS. 6A-6H. Referring to FIG. 58, in order to prepare the distal end of the femur for receiving a femoral component of the implant, a femoral trial cutting guide, such as that shown and described above in FIGS. 12A-12F and 13A, is abutted against the prepared site. The outer perimeter of the femoral trial cutting guide 274 desirably matches the perimeter of the prepared site previously burred on the femur. The cutting guide is preferably handled by attaching the drill guide 286 to the cutting guide.

Figure 59:
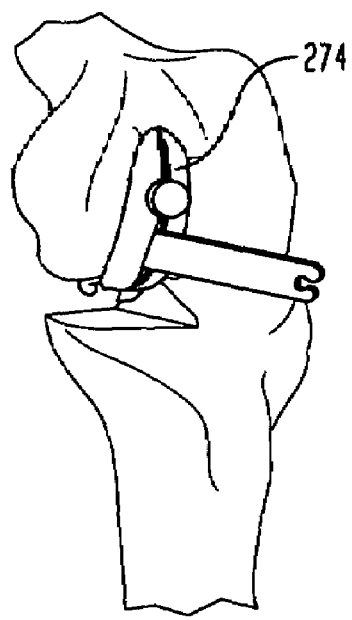

Referring to FIG. 58, after the cutting guide is in place, a drill bit may be passed through an elongated opening in the drill guide 286 to form a post opening for the implant. Referring to FIG. 59, a cutting instrument, such as a saw, may be passed through the elongated slot formed in the cutting guide 274 so as to form an elongated opening for a keel on an implant.

Figure 60:
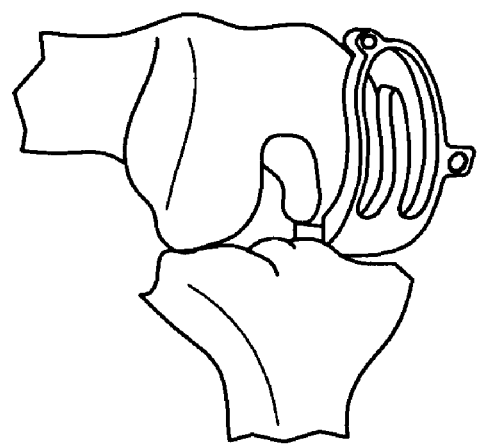
FIGS. 60-62 show a prior art bur template.
Figure 61:
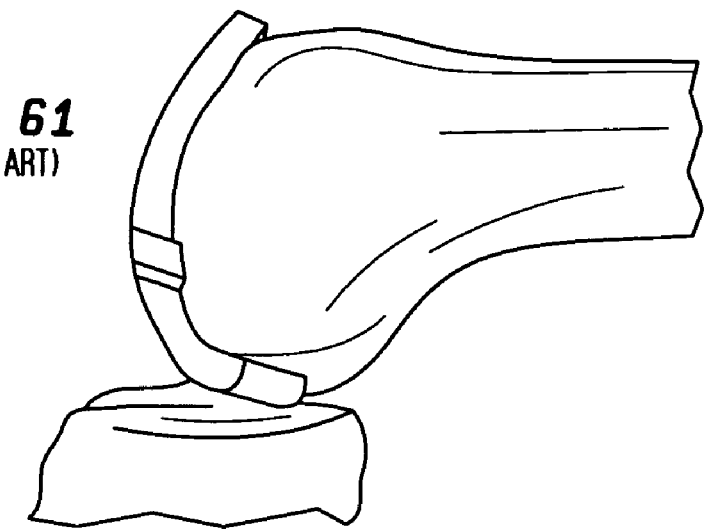
Figure 62:
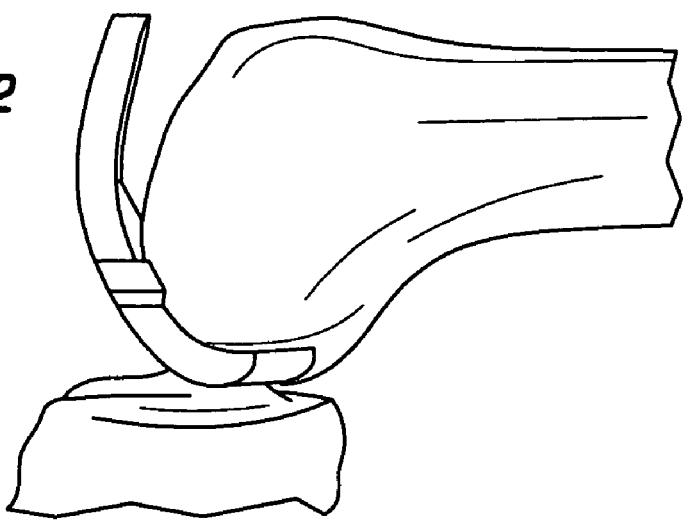

FIGS. 60-62 show a prior art bur template used to prepare the distal end of a femur for receiving an implant. As is well known to those skilled in the art, the template generally conforms to the shape of an actual implant. Thus, it is important that the template conform to the shape of the distal end of the femur as closely as possible. Referring to FIG. 61, after the posterior region of the femoral condyle has been resected, and while the leg remains flexed, the upper part of the bur template is abutted against the condyle at the distal end of the femur. As shown in FIG. 61, a gap forms between the prepared site at the posterior region of the femur and the template. This may result in a number of problems including a poor fit between the implant and the distal end of the femur, joint instability or the removal of excessive bone from the distal end of the femur in order to fit the implant to the femur bone. Conversely, referring to FIG. 62, if the lower end of the bur template is placed in contact with the prepared site at the posterior region of the femur, the upper part of the bur template is spaced from the condyle of the femur. This may cause a number of problems including a poor fit between the implant and the femur bone, joint instability and/or the removal of excessive bone from the femur in order to fit the implant to the femur bone. In certain preferred embodiments, the present invention seeks to avoid these problems by preparing the site at the distal end of the femur before removing bone from the posterior region of the femur. In other preferred embodiments, the present invention seeks to minimize the amount of bone removed from the posterior region of the femur when balancing the gaps between the femur and the tibia when the joint moves between an extended position and a flexed position.

Figure 63A:
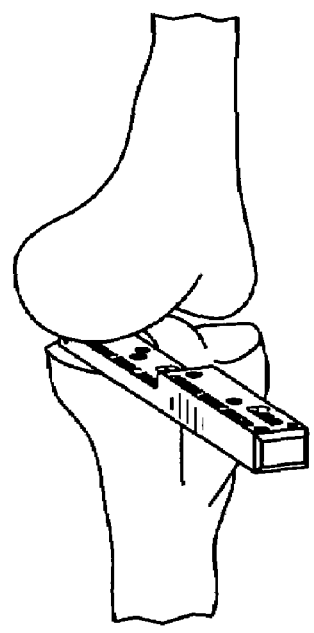
FIGS. 63A-63B show the spacer of FIGS. 22A-22D positioned between an extended knee joint.
Figure 64A:
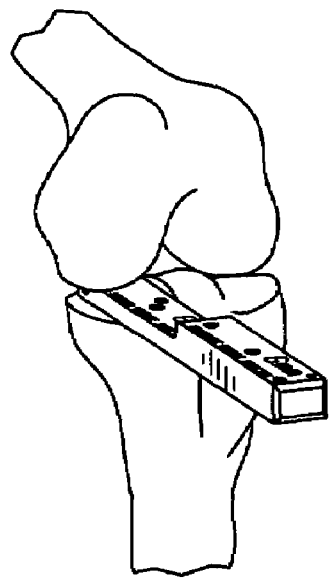
FIGS. 64A-64B show the spacer of FIGS. 22A-22D positioned between a flexed knee joint.
Figure 63B:
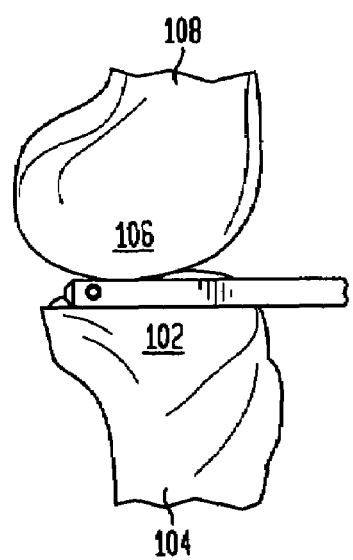
Figure 64B:
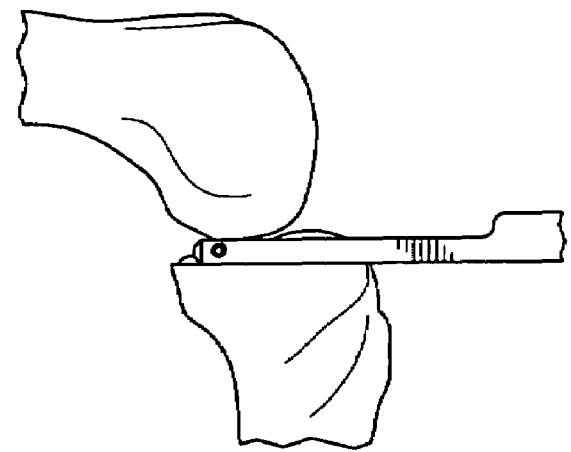

FIGS. 63A and 63B show a knee joint in an extended position, after the tibia has been resected but before the femur is resected. A spacer bar, similar to that shown in FIGS. 22A-22D, is placed in the gap between the distal end 106 of the femur 108 and the proximal end 102 of the tibia 104. The spacer bar is used to measure the distance or gap between the distal end of the femur and the prepared site at the proximal end of the tibia. Referring to FIGS. 64A and 64B, the knee joint is then flexed and the gap between the posterior region of the femur and the prepared site at the proximal end of the tibia is measured. Ideally, the gap between the femur and tibia is the same when the joint is in the extended and flexed positions. For example, in certain instances, the gap when the joint is flexed is 6 mm and the gap when the joint is extended is 6 mm. Often, however, the gap distances change as the joint moves between extended and flexed positions. For example, the flexion gap may be 8 mm and the extension gap may be 6 mm. Thus, certain preferred embodiments of the present invention seek to balance the gap between the femur and the tibia so that the gap in extension is equal to the gap when the knee is flexed. Unlike prior art methods, certain preferred embodiments of the present invention seek to balance the gaps by taking more or less bone from the posterior region of the femur, rather than by taking additional bone from the distal end of the femur. Moreover, in certain preferred embodiments, the posterior resection of the femur takes place only after the site at the distal end of the femur has been completely prepared. In still other preferred embodiments, although some bone may be removed from the posterior region before the distal end of the bone is burred, the final posterior resection region is not completed until the site at the distal end of the femur is finalized.

Referring to FIGS. 63A and 63B, the extension gap between the distal end of the femur and the prepared site at the proximal end of the tibia is about 6 millimeters. Referring to FIGS. 64A and 64B, the flexion gap between the posterior region of the femur and the prepared site at the proximal end of the tibia is about 8 millimeters. Thus, the gap is 2 mm larger in flexion than in extension. The present invention seeks to balance the gaps so that the gap in flexion is equal to the gap in extension. In certain preferred embodiments, the present invention balances the gap by decreasing the flexion gap by 2 millimeters, rather than increasing the extension gap by 2 millimeters. As a result, less bone is removed from the femur.

FIG. 65 shows a gap balancing table that may be used for calculating the amount of bone that is removed from the posterior condyle of the femur. The table may be used by a surgeon for balancing the flexion and extension gaps of a knee joint. As noted above, use of the table preferably minimizes the amount of bone that is removed from the femur. Use of the table also preferably results in proper positioning of the implant parts on the femur and the tibia and smooth movement of the knee joint when moving between the extended and flexed positions. For purposes of clarity, the table uses 6 mm as the preferred gap for a knee joint in both flexion and extension. This chart also assumes that the thickness of the femoral component of the implant is 6 mm. In other preferred embodiments, other thicknesses may be used, e.g. 4 mm, 8 mm, etc. If the initial gap distance is more or less than 6 mm, then more or less bone is removed from the posterior region of the femoral condyle so that the final gap distance in extension is the same as the final gap distance in extension.

Referring to the table, the gap distance associated with a tight fit is 4 mm; the gap distance associated with a good fit is 6 mm and the gap distance associated with a loose fit is 8 mm. The table includes a first row that compares a tight extension gap (4 mm) with a tight (4 mm), good (6 mm) and loose (8 mm) flexion gap. If the extension gap and the flexion gap are both tight, then the gap is considered to be in balance and the standard 6 mm of bone is removed from the posterior condyle. If the extension gap is tight (4 mm) and the flexion gap is good (6 mm), then the gaps are not in balance. In order to balance the gaps, 2 mm less bone material is removed from the posterior region of the femoral condyle for a total of 4 mm (6 mm−2 mm=4 mm) of bone being removed. If the extension gap is tight (4 mm) and the flexion gap is loose (8 mm), then the gaps are not in balance and 4 mm less bone material is removed from the posterior region of the femoral condyle for a total of 2 mm (6 mm–4 mm=2 mm) of bone being removed.

The second row of the gap balancing table is used when the extension gap is good (e.g. 6 mm). If the extension gap is good (6 mm) and the flexion gap is tight (4 mm), then the gaps are not in balance. In order to balance the gaps, 2 mm of additional bone is removed from the posterior region of the femoral condyle for a total of 8 mm (6 mm+2 mm=8 mm) of bone being removed. If the extension gap and the flexion gap are both good, then the gap is considered to be in balance and the standard 6 mm of bone is removed from the posterior region of the femoral condyle. If the extension gap is good (6 mm) and the flexion gap is loose (8 mm), then the gaps are not in balance and 2 mm less bone is removed from the posterior region of the femoral condyle for a total of 4 mm (6 mm–2 mm=4 mm) of bone being removed.

The third row of the gap balancing table is used when the extension gap is loose (e.g. 8 mm). If the extension gap is loose (8 mm) and the flexion gap is tight (4 mm), then 4 mm of additional bone is removed from the posterior region of the femoral condyle for a total of 10 mm (6 mm+4 mm=8 mm) of bone being removed. If the extension gap is loose (8 mm) and the flexion gap is good (6 mm), then 2 mm of additional bone is removed from the posterior region of the femoral condyle for a total of 8 mm (6 mm+2 mm=8 mm) of bone being removed. If the extension gap is loose (8 mm) and the flexion gap is loose (8 mm), then the gap is balanced and the standard 6 mm (6 mm+0 mm=6 mm) of bone is removed from the posterior region of the femoral condyle and the 8 mm tibial component is preferably used.

Figure 66:
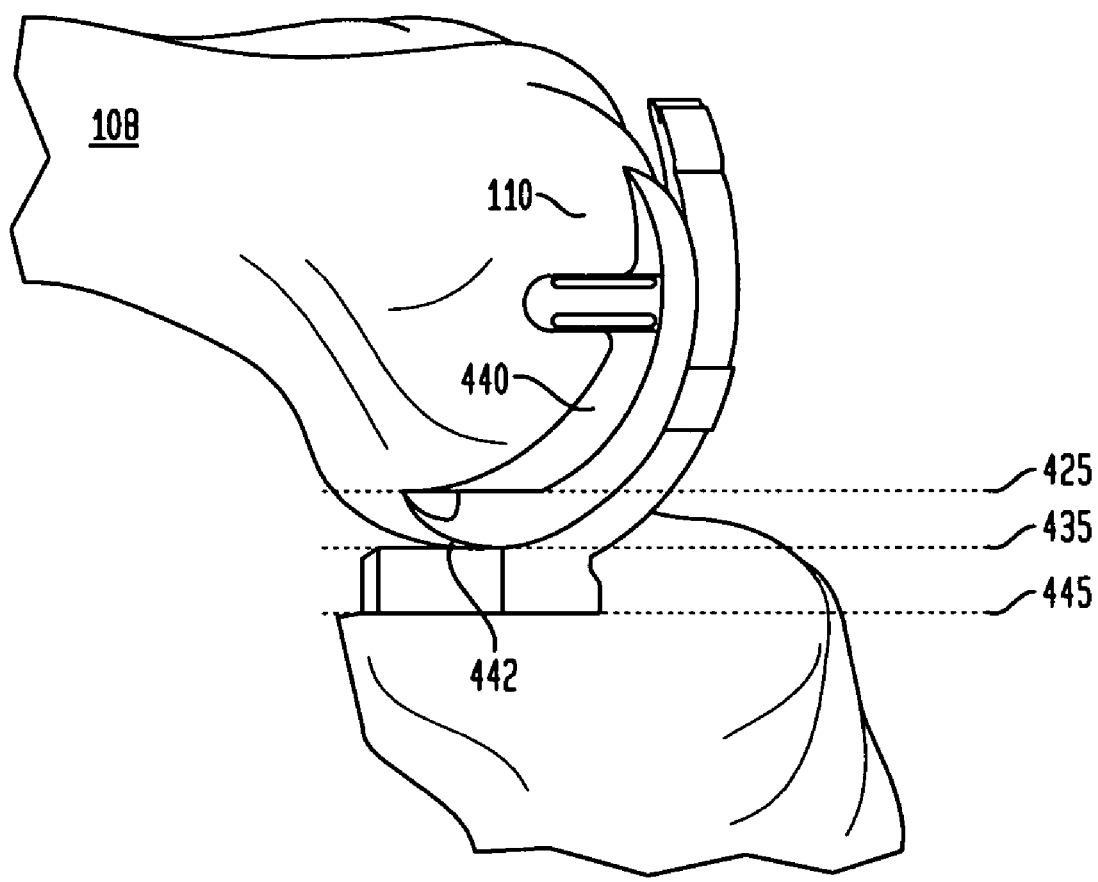
FIG. 66 shows a sagittal view of a flexed knee joint with a combination bur template and spacer block inserted into the knee joint.

In FIG. 66, the flexion gap is 8 mm and the extension gap is 6 mm so that the flexion gap is 2 mm greater than the extension gap. Thus, a standard 6 mm posterior resection will result in a flexion instability of 2 mm. This is shown in FIG. 66 where reference line 425 designates the cut line for a standard 6 mm posterior resection and line 435 is 6 mm away from line 425 (the thickness of the femoral component of the implant). When the femoral component 440 is attached to the bone, the outer surface 442 is present at line 435. However, an 8 mm flexion gap still remains between the proximal end of the tibia (designated by line 445) and the outer surface of the implant (designated by line 435). Thus, in order to balance the flexion gap with the extension gap, the posterior resection must be lowered by 2 mm so that the outer surface of the implant is lowered by 2 mm. Lowering the femoral component by 2 mm will result in a 6 mm flexion gap and a 6 mm extension gap. As a result, when the femoral component 440 shown in FIG. 66 is attached to the distal end of the femur 108, the outer surface 442 of the implant 440 will form a flexion gap of 6 mm.

Figure 67:
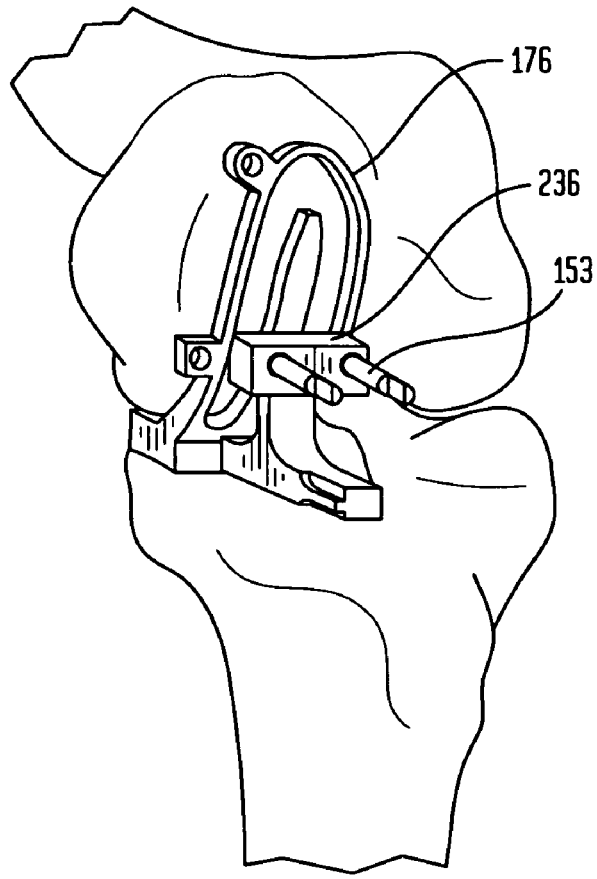
FIG. 67 shows a posterior resection guide locator coupled with a combination bur template and spacer block, in accordance with certain preferred embodiments of the present invention.
Figure 68:
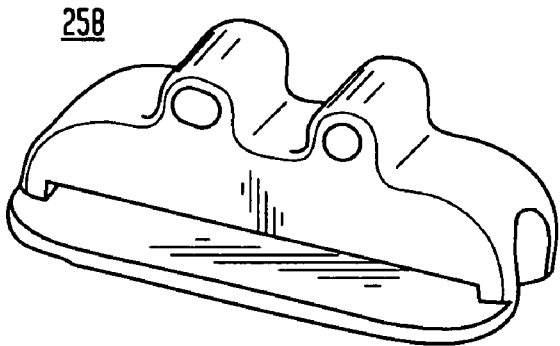
FIG. 68 shows the posterior resection guide shown in FIGS. 10A-10D.
Figure 69:
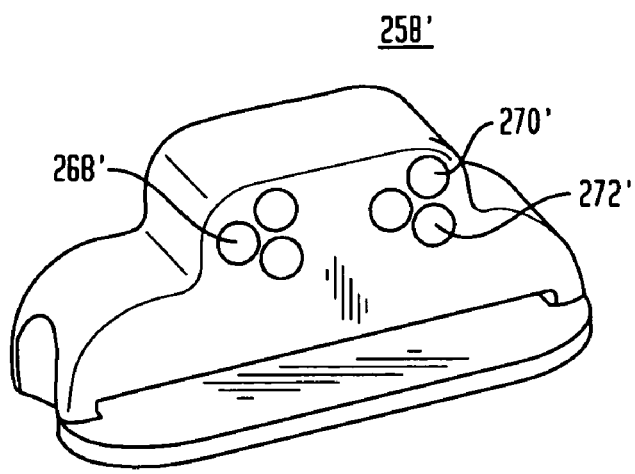
FIG. 69 shows the posterior resection guide shown in FIGS. 11A-11C.

Adjusting the posterior resection is shown in conjunction with FIGS. 67-69. Referring to FIG. 67, after the bur template/spacer block has been positioned between the knee joint and pinned to the femur, the alignment rail of the posterior resection guide locator 236 is inserted into the alignment opening of the bur template/spacer block 176. Pins 153 are then passed through the pin openings of the posterior resection guide locator and into the distal end of the femur bone. As shown in FIGS. 39-40, the posterior resection guide locator 236 is then removed so that only the pins 153 remain attached to the bone. Referring to FIGS. 40-43 and 68, if the flexion gap matches the extension gap, then the standard posterior resection guide 258 may be used to provide a 6 mm posterior resection. The prepared site with the 6 mm posterior resection is shown in FIG. 43.

If the flexion gap does not match the extension gap, then the posterior resection must be adjusted from the standard 6 mm cut as discussed above with reference to the gap balancing table of FIG. 65. This may be accomplished by using a second posterior resection guide 258', shown in FIG. 69, having three sets of pin openings. Although three sets of pin openings are shown, it is contemplated that other preferred embodiments may have four or more sets of pin openings for further modification of the amount of bone removed during a posterior resection. The middle set of openings 268' provides for a standard posterior resection of 6 mm of bone. The upper set of openings 270' lowers the posterior resection guide 258' by 2 millimeters so that the posterior resection removes 4 mm of bone. In certain preferred embodiments, the upper set of openings 270' is used when the flexion gap is greater than the extension gap. The posterior resection guide 258' also includes a lower set of openings 272' that is used when the posterior resection must be raised by 2 mm. The third set of openings 272' may be used when the flexion gap is less than the extension gap. In other preferred embodiments, the sets of openings may be 1 mm apart, or another desired distance.

Figure 70A:
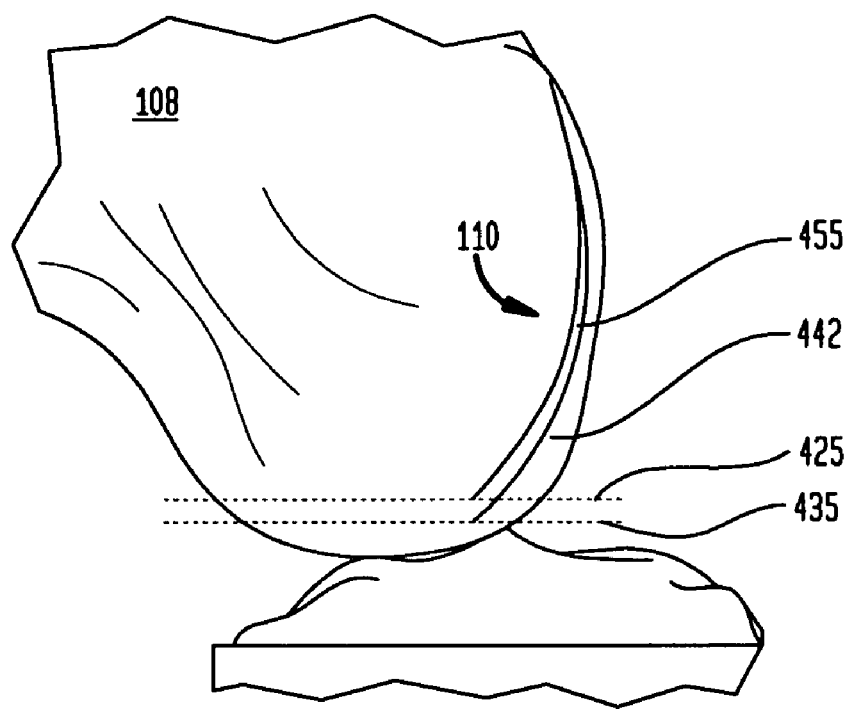
FIGS. 70A and 70B show a method of aligning a knee implant, in accordance with certain preferred embodiments of the present invention.
Figure 70B:
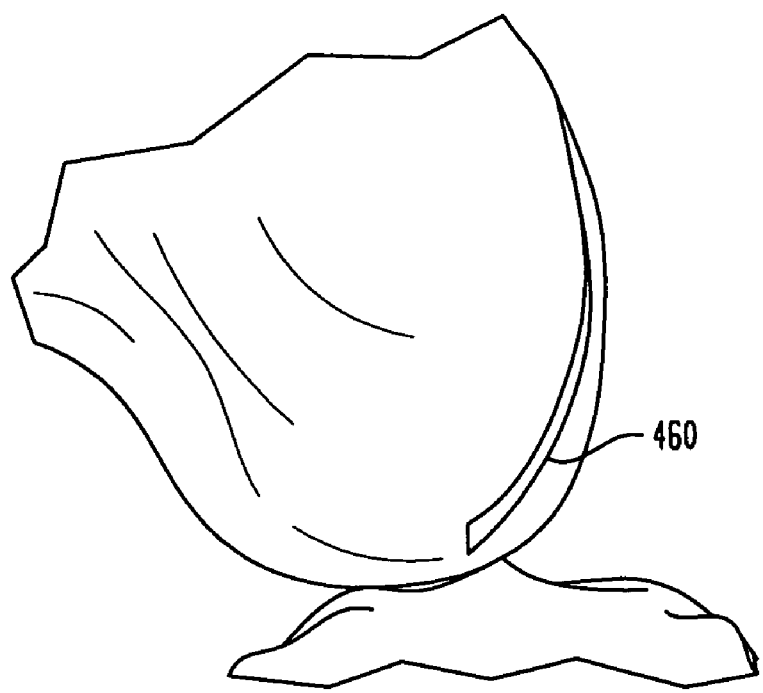

Referring to FIG. 70A, line 425 shows the standard posterior resection of 6 mm of bone. Line 435 shows a posterior resection that has been lowered 2 mm so that only 4 mm of bone is removed. Line 455 shows the burred surface 455 formed at the femoral condyle 110 at the distal end of the femur 108, with the inner surface of the femoral component of the implant being shown at line 442. Due to downward shifting of the femoral component by about 2 mm (preferably after the distal burring is accomplished), a gap may form between the burred surface 455 and the inner surface 442 of the femoral component. Referring to FIG. 70B, bone cement 460 may be used for filling the gap resulting from the downward shifting of the femoral component.

Figure 71:
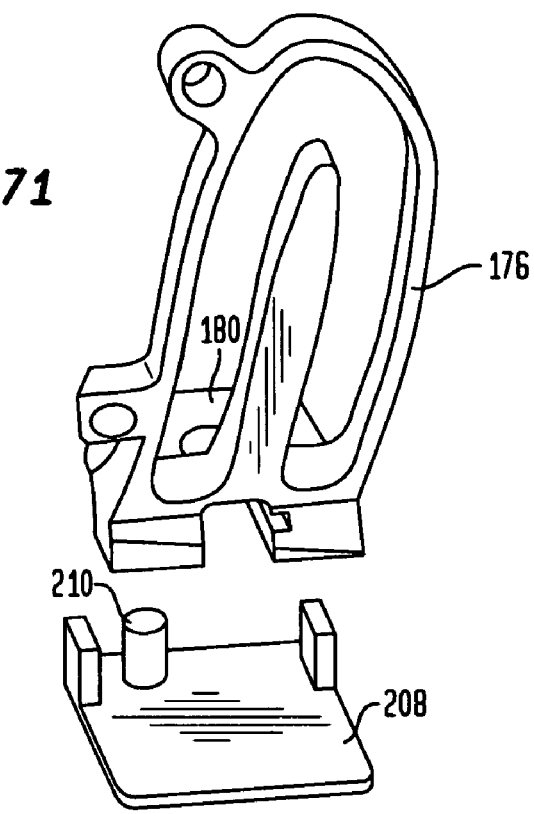
FIG. 71 shows a perspective view of a bur template/spacer block and shim engageable therewith, in accordance with certain preferred embodiments of the present invention.
Figure 72:
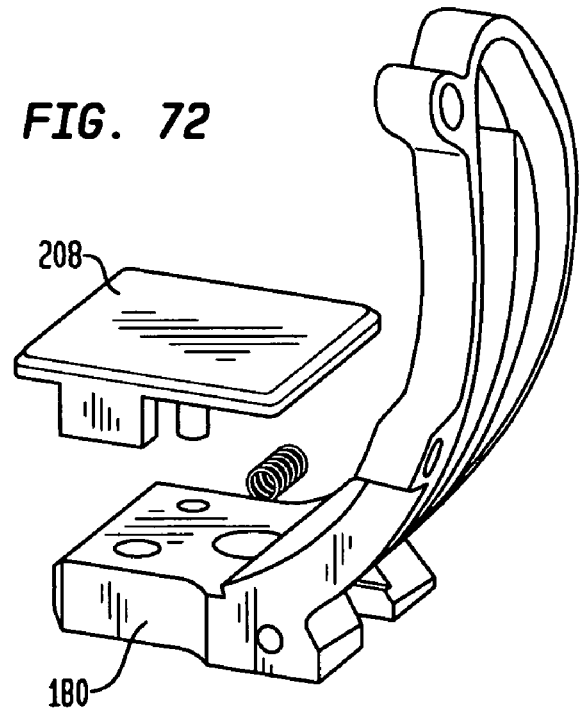
FIG. 72 shows a perspective view of a bur template/spacer block and shim engageable therewith, in accordance with another preferred embodiment of the present invention.

In other preferred embodiments of the present invention, the amount of bone removed during the posterior resection may be controlled by coupling a shim with the spacer block portion of the bur template/spacer block. The shim may be coupled with either the top surface of the spacer block or the bottom surface of the spacer block. FIG. 71 shows the bur template/spacer block 176 of FIG. 6A aligned for assembly with shim 208 of FIG. 7A. Shim 208 includes a post 210 that is insertible in an opening extending through spacer block 180. In FIG. 71, the shim is oriented for assembly with a bottom surface of the spacer block. In FIG. 72, the shim 208 is oriented for assembly with a top surface of the spacer block 180.

Figure 73:
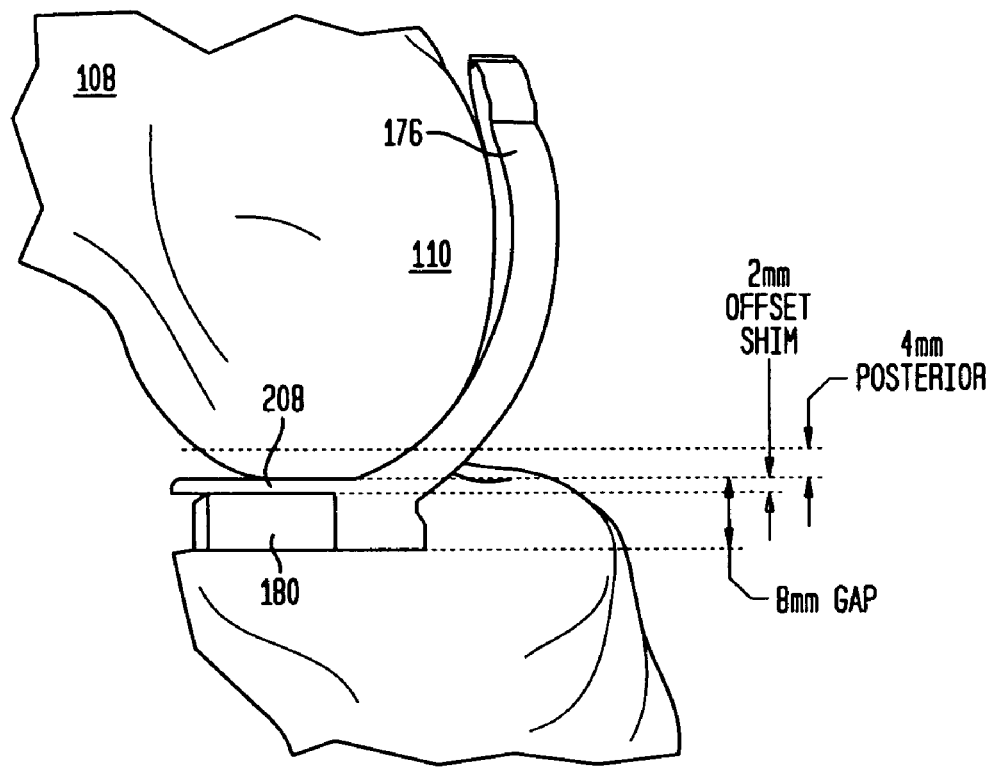
FIGS. 73-76 show a method of inserting a femoral component of a knee implant, in accordance with another preferred embodiment of the present invention.

Referring to FIG. 73, the shim 208 having a thickness of 2 mm is assembled with the top surface of the spacer block 180. The addition of the 2 mm shim on top of the spacer block lowers the posterior resection by 2 mm. As a result, when the standard posterior resection guide 258 of FIG. 68 is slid over the pins shown in FIG. 40 and the resection conducted, only 4 mm of bone is removed from the posterior region, rather than the standard 6 mm.

Figure 74:
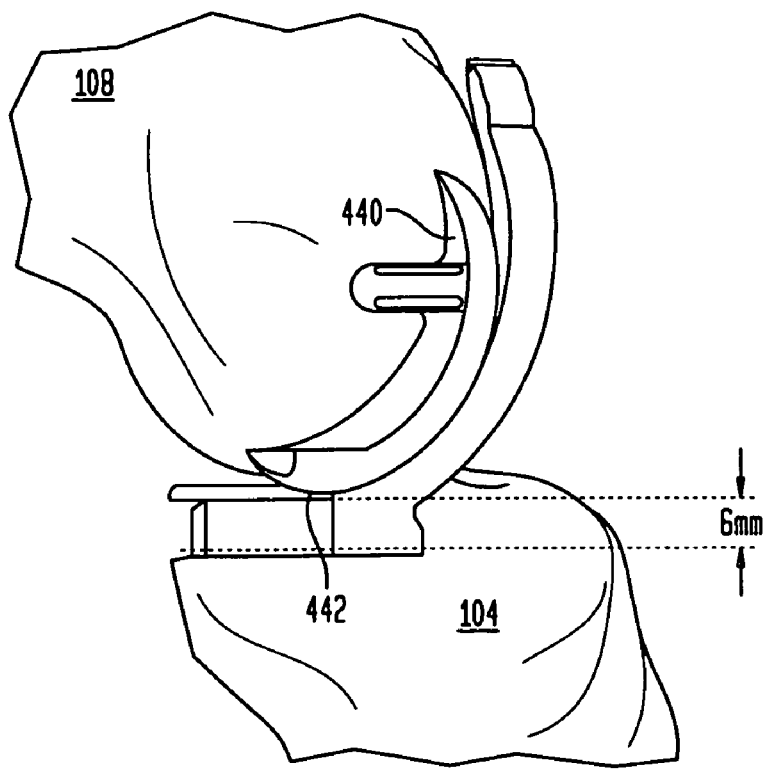

Referring to FIG. 74, when the implant 440 is attached to the prepared site on the femur 108, the gap between the outer surface 442 of the implant 440 and the upper prepared surface of the tibia 104 is 6 millimeters. This 6 millimeter gap in flexion is the same distance as the 6 mm extension gap.

Figure 75:
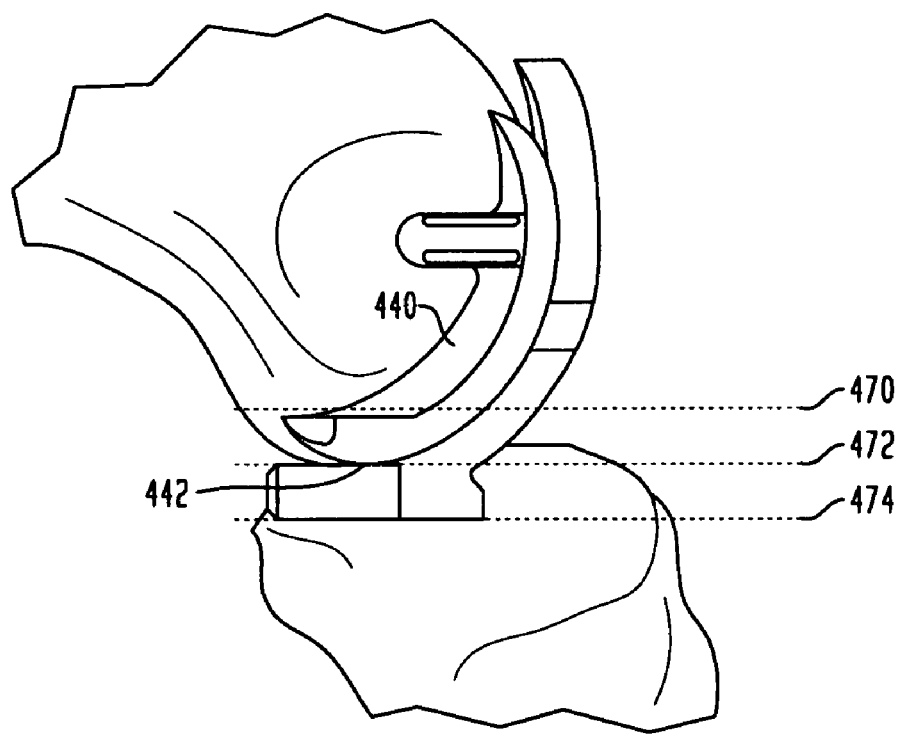
Figure 76:
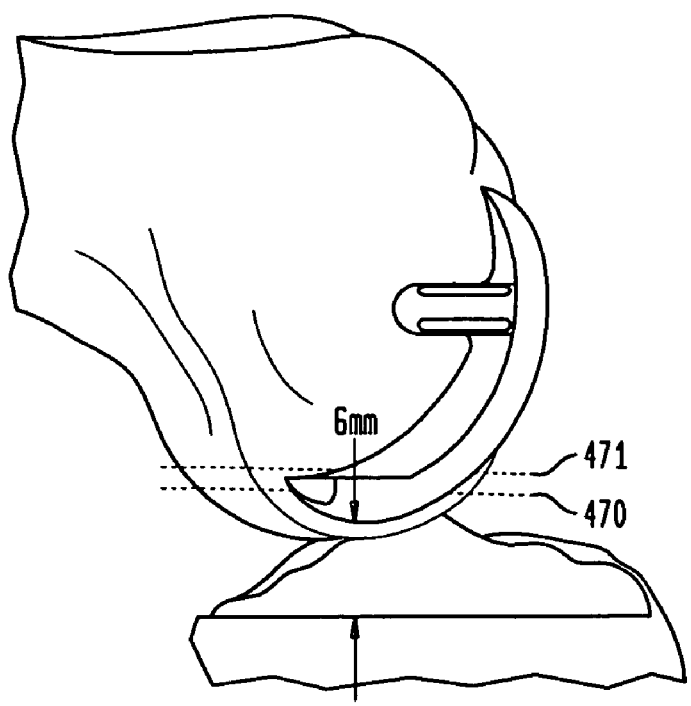

FIGS. 75 and 76 show a knee joint having a flexion gap that is less than the extension gap. In order to balance the gaps, the posterior resection must be raised by a particular distance. FIG. 75 shows a standard 6 millimeter posterior resection line 470 that may be formed using the standard posterior resection guide 258 shown in FIG. 68. When the implant 440 is attached to the distal end of the femur, the outer surface 442 of the implant defines a tangent line 472 that is 4 mm from line 474. In this case, a 2 mm extension instability exists. Correcting this situation requires the posterior resection to be raised 2 mm so that the flexion gap matches the extension gap.

Referring to FIG. 76, in order to raise the outer surface of the implant 2 mm, the posterior resection line is first raised 2 mm to line 471. As a result, when the implant 440 is attached to bone, the flexion gap between the outer surface 442 of the implant part 440 and the prepared surface of the tibia is 6 millimeters, which matches the 6 millimeter extension gap.

Figure 77A:
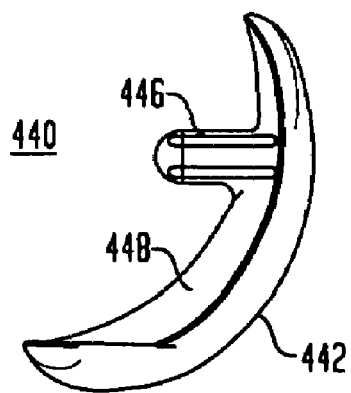
FIGS. 77A-77B show a femoral component of a knee implant, in accordance with certain preferred embodiments of the present invention.
Figure 77B:
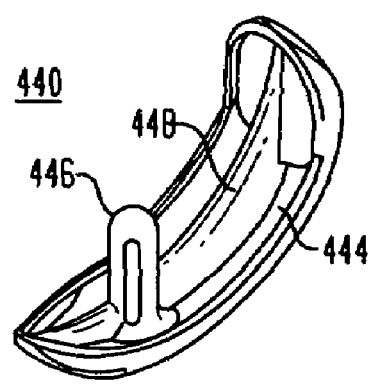

After the sites have been prepared at the distal end of the femur and the proximal end of the tibia, a femoral component of the implant is connected with the distal end of the femur and a tibial component of the implant is connected to the proximal end of the tibia. Referring to FIGS. 77A and 77B, the femoral component 440 has an outer surface 442 that is preferably curved and an inner surface 444. The femoral component 440 also preferably includes a post 446 projecting from the inner surface 444 and a keel 448 projecting from the inner surface 444 thereof. The femoral component 440 is assembled with the distal end of the femur by abutting the inner surface 444 against the femoral bone. The post 446 and the keel 448 are preferably pressed into openings previously formed in the bone as described above with respect to the femoral trial cutting guide shown in FIGS. 57-59.

Figure 78A:
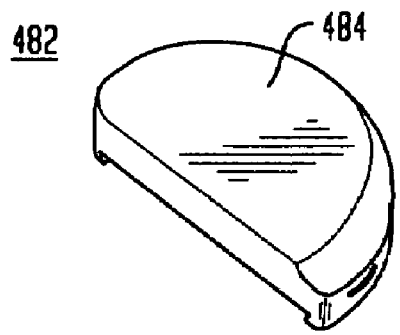
FIGS. 78A-78B show a tibial component of a knee implant, in accordance with certain preferred embodiments of the present invention.
Figure 78B:
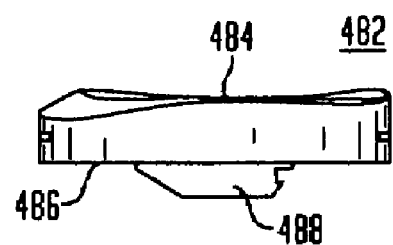

Referring to FIGS. 78A and 78B, the implant includes a tibial component 482 having a top surface 484 adapted to abut against the outer surface 442 of the femoral component 440 (FIG. 77A). The tibial component 482 includes an underside 486 having a keel 488 projecting therefrom. The keel is adapted to be inserted into a keel opening, such as the keel opening shown in FIG. 56.

Figure 79:
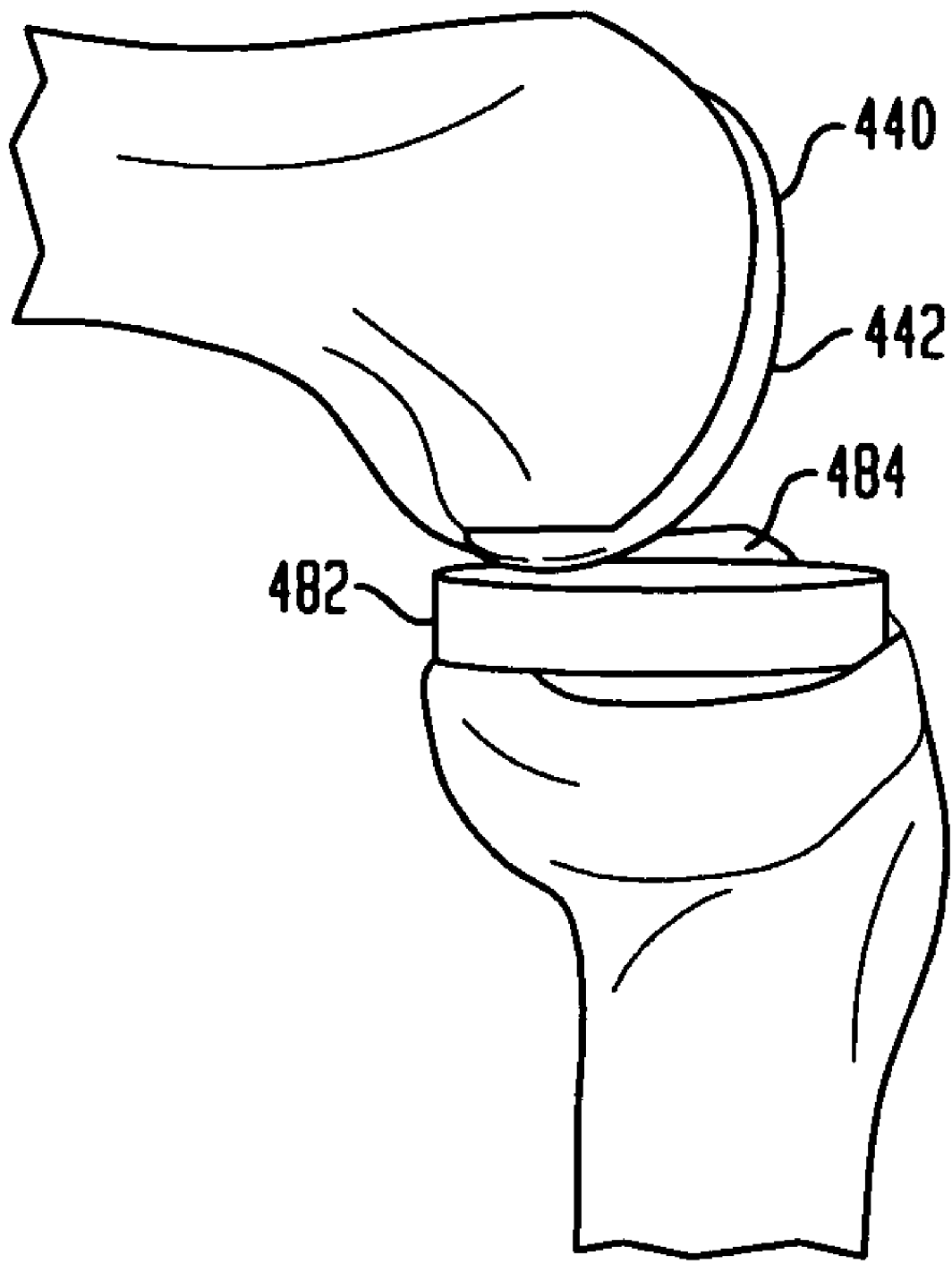
FIG. 79 shows the femoral component of FIGS. 77A-77B and the tibial component of FIGS. 78A-78B implanted in a knee joint.

Referring to FIG. 79, after final insertion of the implant, the outer surface 442 of femoral component 440 engages the top surface 484 of tibial component 482. The opposing outer surfaces of the two implant parts engage one another as the knee joint moves between a flexed position and an extended position. In certain preferred embodiments, the femoral and tibial components 440, 482 may be secured using cement. In particular preferred embodiments, the cement is applied over the post 446 and keel 448 of the femoral component 440 shown in FIG. 77A. Cement may also be applied over the bottom surface 486 and the keel 488 of the tibial component 482 shown in FIG. 78B. The first and second implant parts may be impacted into place just by using a striking instrument such as a hammer, an impactor or a mallet. Any excessive cement present around the implant parts 440, 482 is preferably removed.

Disclosed herein are unicondylar knee implants, surgical instruments and procedures in accordance with certain preferred embodiments of the present invention. It is contemplated, however, that the implants, instruments and procedures may be slightly modified, and/or used in whole or in part and with or without other instruments or procedures, and still fall within the scope of the present invention. Although the present invention may discuss a series of steps in a procedure, the steps can be accomplished in a different order, or be used individually, or in subgroupings of any order, or in conjunction with other methods, without deviating from the scope of the invention.

While there has been described and illustrated herein embodiments of unicondylar knee implants and insertion methods therefor, it will be apparent to those skilled in the art that variations and modifications are possible without deviating from the broad spirit and principle of the present invention. The present invention shall, therefore, not be limited solely to the specific embodiments disclosed herein and other arrangements may be devised without departing from the spirit and scope of the present invention as defined by the appended claims.

The invention claimed is:

1. A system for forming a tibial keel opening comprising:
at least one template having a top surface, a bottom surface, a trailing end and a leading end, a channel extending from the trailing end toward the leading end along a first axis and a central opening extending between the top and bottom surfaces along a second axis, the channel being bounded by at least one interior edge of said at least one template, the at least one interior edge having a groove formed therein that extends between the trailing and leading ends of said at least one template, wherein the bottom surface of said at least one template is positionable atop bone;
a bone cutting instrument advanceable through the central opening in said at least one template; and
a guide having a base portion including lateral projections and a leading end that is alignable and slidable with the channel such that the leading end of the guide is received in said at least one template along the first axis thereof and the lateral projections are received in the groove of the channel forming a tongue in groove coupling between said at least one template and said guide, the guide having a body portion including at least one slot having an axis, the axis of the slot being angled relative to the first and second axes of said at least one template when said tongue is in said groove such that the leading end of said guide is aligned with the channel in said at least one template,
wherein said at least one slot guides advancement of said cutting instrument toward the leading end of said guide and through the central opening in said at least one template.

2. The system as claimed in claim 1, wherein said at least one template comprises a plurality of templates having different sizes, each said template being used for forming keel openings having different sizes.

3. The system as claimed in claim 2, further comprising a template holder having a plurality of arms, each said arm having an end being adapted to hold one of said plurality of templates.

4. The system as claimed in claim 2, wherein said at least one slot comprises a plurality of slots, and wherein each of said slots is associated for use with one of said differently sized templates.

5. The system as claimed in claim 4, wherein said plurality of slots extend from a trailing end of said guide toward the leading end of said guide.

6. The system as claimed in claim 5, wherein said plurality of slots extend along respective axes that are substantially parallel to one another.

7. The system as claimed in claim 1, wherein said at least one template has at least one anchor pin opening extending from the top surface to the bottom surface thereof.

8. The system as claimed in claim 1, wherein said template has opposing sides that extend between the trailing and leading ends of said template, wherein one of said sides has a straight edge and the other one of said sides has a curved edge.

9. The system as claimed in claim 1, wherein the guide includes at least one anchor pin opening extending therethrough for anchoring said guide to bone.

10. A system for forming a tibial keel opening in bone comprising:
a plurality of templates having different sizes, each said template having a top surface, a bottom surface, a trailing end and a leading end, a channel extending from the trailing end toward the leading end along a first axis and a central opening extending between the top and bottom surfaces along a second axis, the channel being bounded by at least one interior edge of said plurality of templates, the at least one interior edge having a groove formed therein that extends between the trailing and leading ends of said plurality of templates;

a bone cutting instrument; and a guide having a trailing end, and a base portion including lateral projections and a leading end that is alignable and slidable with the channel such that the leading end of the guide is received in said templates along the first axis thereof and the lateral projections are received in the groove of the channel forming a tongue in groove coupling between said plurality of templates and the guide, the guide having a body portion including a plurality of slots extending between the trailing end and the leading end of said guide for guiding advancement of said bone cutting instrument, said plurality of slots of said guide having an axis, wherein said axis of said plurality of slots of said guide is angled relative to the first and second axes of said templates when said tongue is in said groove such that the leading end of said guide is aligned with the central openings in said templates.

11. The system as claimed in claim 10, wherein said bone cutting instrument is inserted into a first one of said slots when said guide is coupled with a first one of said templates and said bone cutting instrument is inserted into a second one of said slots when said guide is coupled with a second one of said templates.

12. The system as claimed in claim 11, wherein the second one of said templates is larger than the first one of said template.

13. The system as claimed in claim 11, wherein said bone cutting instrument is inserted into a third one of said slots when said guide is coupled with a third one of said templates.

14. The system as claimed in claim 10, wherein said plurality of slots extend along axes that are substantially parallel to one another.

15. The system as claimed in claim 10, wherein said slots extend along axes that cross the top surfaces of said templates when said templates are coupled with said guide.

16. The system as claimed in claim 10, wherein only one of said templates is connectable with the leading end of said guide at any one time.

17. The system as claimed in claim 10, wherein said bone cutting instrument comprises:

a first cutting instrument having a leading end, a trailing end and an elongated opening extending between the leading end and the trailing end; and a second cutting instrument insertible into the elongated opening of said first cutting instrument.

18. The system as claimed in claim 17, wherein said first cutting instrument is inserted into one of said slots and fully advanced toward the leading end of said guide before said second cutting instrument is inserted into the elongated opening of said first cutting instrument.

19. The system as claimed in claim 10, further comprising a hook provided at the leading end of said guide and a hook opening provided in at least one of the top and bottom surfaces of said templates for securing said guide to said templates.

20. A system for forming keel openings in tibial bone comprising:

a plurality of templates having different sizes, each said template having a top surface, a bottom surface, a trailing end and a leading end, a channel extending from the trailing end toward the leading end along a first axis and a central opening extending between the top and bottom surfaces along a second axis, the channel being bounded by at least one interior edge of said plurality of templates, the at least one interior edge having a groove formed therein that extends between the trailing and leading ends of said plurality of templates;

a bone cutting instrument for forming the keel openings; and a guide including a base portion having lateral projections and a leading end that is alignable and slidable with the channel such that the leading end of the guide is received in said plurality of templates along the first axis of said plurality of templates and the lateral projections are received in the groove of the channel forming a tongue in groove coupling between said plurality of templates and said guide, said guide including a plurality of slots extending toward the leading end thereof for guiding advancement of said bone cutting instrument through the central openings in said templates, said plurality of slots of said guide having an axis, wherein said axis of said plurality of slots of said guide is angled relative to the first and second axes of said templates when said tongue is in said groove such that the leading end of said guide is aligned with the channel along the first axis of said templates.

* * * * *